(12) United States Patent
Warner et al.

(10) Patent No.: US 10,357,488 B2
(45) Date of Patent: *Jul. 23, 2019

(54) PREDICTING RESPONSE TO ALVOCIDIB BY MITOCHONDRIAL PROFILING

(71) Applicant: Tolero Pharmaceuticals, Inc., Lehi, UT (US)

(72) Inventors: Steven L. Warner, Sandy, UT (US); David J. Bearss, Alpine, UT (US)

(73) Assignee: Tolero Pharmaceuticals, Inc., Lehi, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/132,270

(22) Filed: Sep. 14, 2018

(65) Prior Publication Data

US 2019/0030017 A1 Jan. 31, 2019

Related U.S. Application Data

(63) Continuation of application No. 15/874,755, filed on Jan. 18, 2018, now abandoned, which is a continuation of application No. 15/134,051, filed on Apr. 20, 2016, now Pat. No. 9,901,574.

(60) Provisional application No. 62/150,138, filed on Apr. 20, 2015.

(51) Int. Cl.
| | | |
|---|---|---|
| A61K 31/453 | (2006.01) | |
| G01N 33/574 | (2006.01) | |
| C12Q 1/6886 | (2018.01) | |
| G01N 33/50 | (2006.01) | |
| A61K 31/136 | (2006.01) | |
| A61K 31/7068 | (2006.01) | |

(52) U.S. Cl.
CPC .......... *A61K 31/453* (2013.01); *A61K 31/136* (2013.01); *A61K 31/7068* (2013.01); *C12Q 1/6886* (2013.01); *G01N 33/5011* (2013.01); *G01N 33/5079* (2013.01); *G01N 33/5748* (2013.01); *G01N 33/57426* (2013.01); *C12Q 2600/106* (2013.01); *C12Q 2600/158* (2013.01); *G01N 2333/82* (2013.01); *G01N 2800/52* (2013.01)

(58) Field of Classification Search
CPC ................ A61K 31/453; A61K 31/136; A61K 31/7068; C12Q 1/6886; G01N 33/5011; G01N 33/5079; G01N 33/5748
See application file for complete search history.

(56) References Cited

U.S. PATENT DOCUMENTS

| | | |
|---|---|---|
| 4,522,811 A | 6/1985 | Eppstein et al. |
| 4,676,980 A | 6/1987 | Segal et al. |
| 4,816,567 A | 3/1989 | Cabilly et al. |
| 4,900,727 A | 2/1990 | Kattige et al. |
| 4,946,778 A | 8/1990 | Ladner et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,674,980 A | 10/1997 | Frankel et al. |
| 5,804,604 A | 9/1998 | Frankel et al. |
| 5,916,771 A | 6/1999 | Hori et al. |
| 5,939,598 A | 8/1999 | Kucherlapati et al. |
| 5,965,703 A | 10/1999 | Horne et al. |
| 6,087,366 A | 7/2000 | Park et al. |
| 6,136,981 A | 10/2000 | Brion et al. |
| 6,225,473 B1 | 5/2001 | Breipohl et al. |
| 6,258,540 B1 | 7/2001 | Lo et al. |
| 6,406,912 B1 | 6/2002 | Holla |
| 6,576,647 B2 | 6/2003 | Bafus et al. |
| 6,821,990 B2 | 11/2004 | Kesseler |
| 7,064,193 B1 | 6/2006 | Cory et al. |
| 7,714,005 B2 | 5/2010 | Chen et al. |
| 7,829,662 B2 | 11/2010 | Korsmeyer et al. |
| 7,868,133 B2 | 1/2011 | Korsemeyer et al. |
| 8,168,755 B2 | 5/2012 | Cardone et al. |
| 8,221,966 B2 | 7/2012 | Letai |
| 9,360,473 B2 | 6/2016 | Cardone |
| 9,540,674 B2 | 1/2017 | Letai |
| 9,758,539 B2 | 9/2017 | Siddiqui-Jain et al. |
| 9,856,303 B2 | 1/2018 | Korsmeyer et al. |
| 9,901,574 B2 | 2/2018 | Warner et al. |
| 9,902,759 B2 | 2/2018 | Korsmeyer et al. |
| 2002/0115613 A1 | 8/2002 | Kumar |
| 2003/0073661 A1 | 4/2003 | Matsuyama et al. |
| 2004/0171809 A1 | 9/2004 | Korsmeyer et al. |
| 2005/0153991 A1 | 7/2005 | Gianella-Borradori et al. |
| 2008/0027105 A1 | 1/2008 | Suarez et al. |

(Continued)

FOREIGN PATENT DOCUMENTS

| | | |
|---|---|---|
| CN | 1583776 A | 2/2005 |
| WO | 91/00360 A1 | 1/1991 |

(Continued)

OTHER PUBLICATIONS

Adams et al., "The Bcl-2 Protein Family: Arbiters of Cell Survival," *Science* 281:1322-1326, 1998.
Adlard et al., "Prediction of the response of colorectal cancer to systemic therapy," *Lancet Oncol.* 3:75-82, 2002.
Aït-Ikhlef et al., "The motoneuron degeneration in the wobbler mouse is independent of the overexpression of a Bcl2 transgene in neurons," *Neuroscience Letters* 199:163-166, 1995.
Almarzooqi et al., "Comparison of Peripheral Blood versus Bone Marrow Blasts Immunophenotype in Pediatric Acute Leukemias," *Ibnosina Journal of Medicine and Biomedical Sciences*, pp. 195-204, 2011. (10 pages).

(Continued)

*Primary Examiner* — Brian Whiteman
(74) *Attorney, Agent, or Firm* — Oblon, McClelland, Maier & Neustadt, L.L.P.

(57) ABSTRACT

The present disclosure provides diagnostic methods useful for predicting a patient's response to alvocidib and guiding a physician decision to administer alvocidib to the patient.

8 Claims, 22 Drawing Sheets

(56) References Cited

U.S. PATENT DOCUMENTS

| | | |
|---|---|---|
| 2008/0199890 A1 | 9/2008 | Letai |
| 2008/0234201 A1 | 9/2008 | Korsmeyer et al. |
| 2009/0030005 A1 | 1/2009 | Kamb et al. |
| 2010/0286057 A1 | 11/2010 | Walensky et al. |
| 2011/0008371 A1 | 1/2011 | Michelson |
| 2011/0130309 A1 | 6/2011 | Cardone |
| 2011/0154522 A1 | 6/2011 | Korsmeyer et al. |
| 2011/0251240 A1 | 10/2011 | Suarez et al. |
| 2012/0225851 A1 | 9/2012 | Cardone et al. |
| 2013/0079424 A1 | 3/2013 | Gerber et al. |
| 2013/0122492 A1 | 5/2013 | Khosravi et al. |
| 2013/0149718 A1 | 6/2013 | Letai |
| 2014/0080838 A1 | 3/2014 | Wendel et al. |
| 2014/0303167 A1 | 10/2014 | Choidas et al. |
| 2015/0051249 A1 | 2/2015 | Walensky |
| 2015/0150869 A1 | 6/2015 | Cardone et al. |
| 2015/0301053 A1 | 10/2015 | Pierceall et al. |
| 2015/0352097 A1 | 12/2015 | Cardone et al. |
| 2015/0362479 A1 | 12/2015 | Letai et al. |
| 2016/0178612 A1 | 6/2016 | Cardone |
| 2016/0200786 A1 | 7/2016 | Korsmeyer et al. |
| 2016/0231314 A1 | 8/2016 | Ryan et al. |
| 2016/0258933 A1 | 9/2016 | Letai |
| 2016/0273020 A1 | 9/2016 | Pierceall et al. |
| 2016/0303101 A1 | 10/2016 | Warner et al. |
| 2016/0340376 A1 | 11/2016 | Siddiqui-Jain et al. |
| 2017/0184567 A1 | 6/2017 | Letai |
| 2017/0260268 A1 | 9/2017 | Beatty et al. |
| 2017/0334938 A1 | 11/2017 | Siddiqui-Jain et al. |
| 2018/0172673 A1 | 6/2018 | Bearss et al. |

FOREIGN PATENT DOCUMENTS

| | | |
|---|---|---|
| WO | 92/20373 A1 | 11/1992 |
| WO | 93/08829 A1 | 5/1993 |
| WO | 94/02602 A1 | 2/1994 |
| WO | 94/11026 A2 | 5/1994 |
| WO | 96/15263 A1 | 5/1996 |
| WO | 96/27011 A1 | 9/1996 |
| WO | 96/33735 A1 | 10/1996 |
| WO | 96/34096 A1 | 10/1996 |
| WO | 97/05265 A1 | 2/1997 |
| WO | 99/16787 A1 | 4/1999 |
| WO | 99/53049 A1 | 10/1999 |
| WO | 00/59526 A1 | 10/2000 |
| WO | 01/12661 A2 | 2/2001 |
| WO | 02/20568 A2 | 3/2002 |
| WO | 03/028001 A1 | 4/2003 |
| WO | 03/040168 A2 | 5/2003 |
| WO | 2004/022580 A2 | 3/2004 |
| WO | 2004/058804 A1 | 7/2004 |
| WO | 2005/044839 A2 | 5/2005 |
| WO | 2006/099667 A1 | 9/2006 |
| WO | 2006/101846 A1 | 9/2006 |
| WO | 2007/123791 A2 | 11/2007 |
| WO | 2010/093742 A1 | 8/2010 |
| WO | 2010/147961 A1 | 12/2010 |
| WO | 2011/088137 A2 | 7/2011 |
| WO | 2012/122370 A2 | 9/2012 |
| WO | 2013/082660 A1 | 6/2013 |
| WO | 2013/138702 A2 | 9/2013 |
| WO | 2013/170176 A2 | 11/2013 |
| WO | 2013/188355 A1 | 12/2013 |
| WO | 2013/188978 A1 | 12/2013 |
| WO | 2014/047342 A1 | 3/2014 |
| WO | 2014/066848 A1 | 5/2014 |
| WO | 2015/010094 A1 | 1/2015 |
| WO | 2015/017788 A1 | 2/2015 |
| WO | 2015/042249 A1 | 3/2015 |
| WO | 2015/066305 A1 | 5/2015 |
| WO | 2015/070020 A2 | 5/2015 |
| WO | 2016/061144 A1 | 4/2016 |
| WO | 2016/073913 A1 | 5/2016 |
| WO | 2016/115105 A1 | 7/2016 |
| WO | 2016/149613 S1 | 9/2016 |
| WO | 2016/154380 A1 | 9/2016 |
| WO | 2016/176288 A1 | 11/2016 |
| WO | 2016/176299 A1 | 11/2016 |
| WO | 2017/075349 A1 | 5/2017 |

OTHER PUBLICATIONS

Altschul et al., "Gapped BLAST and PSI-BLAST: a new generation of protein database search programs," *Nucleic Acids Research* 25(17):3389-3402, 1997.

De Azevedo Jr. et al., "Structural basis for inhibition of cyclin-dependent kinase 9 by flavopiridol," *Biochemical and Biophysical Research Communications* 293:566-571, 2002.

Bae et al., "Underphosphorylated BAD interacts with diverse antiapoptotic Bcl-2 family proteins to regulate apoptosis," *Apoptosis* 6:319-330, 2001.

Barretina et al., "The Cancer Cell Line Encyclopedia enables predictive modelling of anticancer drug sensitivity," *Nature* 483:603-607, 2012; Addendum in: *Nature* 492:290, 2012.

Bearss, "NOXA Priming—Predictive Biomarker for Patients With Acute Myeloid Leukemia to Improve Treatment Outcomes," 2016, retrieved from https://openforum.hbs.org/challenge/precision-medicine/submit-ideas/noxa-priming-predic . . . , 7 pages.

Blachly et al., "Emerging Drug Profile: Cyclin-Dependent Kinase Inhibitors," *Leuk Lymphoma* 54:2133-2143, 2013. (22 pages).

Bodet et al., "BH3-only protein Bik is involved in both apoptosis induction and sensitivity to oxidative stress in multiple myeloma," *British Journal of Cancer* 103:1808-1814, 2010.

Bose et al., "Mcl-1 as a therapeutic target in acute myelogenous leukemia (AML)," *Leukemia Research Reports* 2:12-14, 2013.

Bouillet et al., "Proapoptotic Bcl-2 Relative Bim Required for Certain Apoptotic Responses, Leukocyte Homeostasis, and to Preclude Autoimmunity," *Science* 286:1735-1738, 1999.

Boyd et al., "Bik, a novel death-inducing protein shares a distinct sequence motif with Bcl-2 family proteins and interacts with viral and cellular survival-promoting proteins," *Oncogene* 11:1921-1928, 1995.

Brady et al., "Reflections on a peptide," *Nature* 368:692-693, 1994.

Brennan et al., "Preparation of Bispecific Antibodies by Chemical Recombination of Monoclonal Immunoglobulin $G_1$ Fragments," *Science* 229:81-83, 1985.

Brunelle et al., "MCL-1-dependent leukemia cells are more sensitive to chemotherapy than BCL-2-dependent counterparts," *J. Cell. Biol.* 187(3):429-442, 2009.

Brunetto et al., "First-in-human, Pharmacokinetic and Pharmacodynamic Phase I Study of Resminostat, an Oral Histone Deacetylase Inhibitor, in Patients with Advanced Solid Tumors," *Clin Cancer Res* 19(19):5494-5504, 2013.

Buggy et al., "CRA-024781: a novel synthetic inhibitor of histone deacetylase enzymes with antitumor activity in vitro and in vivo," *Mol Cancer Ther* 5(5):1309-1317, 2006.

Buron et al., "Use of Human Cancer Cell Lines Mitochondria to Explore the Mechanisms of BH3 Peptides and ABT-737-Induced Mitochondrial Membrane Permeabilization," *PLoS One* 5(3):e9924, 2010. (13 pages).

Byrd et al., "Flavopiridol Induces Apoptosis in Chronic Lymphocytic Leukemia Cells Via Activation of Caspase-3 Without Evidence of bcl-2 Modulation or Dependence on Functional p53," *Blood* 92:3804-3816, 1998.

Byrd et al., "Sequential Phase II Studies of Flavopiridol by 72-Hour Continuous Infusion and 1-Hour Intravenous Bolus for the Treatment of Relapsed B-Cell Chronic Lymphocytic Leukemia: Results from CALGB Study 19805," *Blood* 104:3485, 2004. (2 pages).

Byrd et al., "Flavopiridol Administered as a Pharmacologically-Derived Schedule Demonstrates Marked Clinical Activity in Refractory, Genetically High Risk, Chronic Lymphocytic Leukemia (CLL)," *Blood* 104:341, 2004. (2 pages).

Byrd et al., "Chronic Lymphocytic Leukemia," *Hematology*, pp. 163-183, 2004. (21 pages).

Byrd et al., "Treatment of Relapsed Chronic Lymphocytic Leukemia by 72-Hour Continuous Infusion or 1-Hour Bolus Infusion of

(56) References Cited

OTHER PUBLICATIONS

Flavopiridol: Results from Cancer and Leukemia Group B Study 19805," *Clin Cancer Res* 11:4176-4181, 2005.
Byrd et al., "Flavopiridol administered using a pharmacologically derived schedule is associated with marked clinical efficacy in refractory, genetically high-risk chronic lymphocytic leukemia," *Blood* 109:399-404, 2007.
Calin et al., "A MicroRNA Signature Associated with Prognosis and Progression in Chronic Lymphocytic Leukemia," *The New England Journal of Medicine* 353:1793-1801, 2005.
Carlson et al., "Flavopiridol Induces $G_1$ Arrest with Inhibition of Cyclin-dependent Kinase (CDK) 2 and CDK4 in Human Breast Carcinoma Cells," *Cancer Research* 56:2973-2978, 1996.
Caron et al., "Engineered Humanized Dimeric Forms of IgG Are More Effective Antibodies," *J. Exp. Med.* 176:1191-1195, 1992.
Cartron et al., "The First α Helix of Bax Plays a Necessary Role in Its Ligand-Induced Activation by the BH3-Only Proteins Bid and PUMA," *Molecular Cell* 16:807-818, 2004.
Certo et al., "Mitochondria primed by death signals determine cellular addiction to antiapoptotic BCL-2 family members," *Cancer Cell* 9:351-365, 2006.
Chao et al., "Flavopiridol Inhibits P-TEFb and Blocks HIV-1 Replication," *The Journal of Biological Chemistry* 275:28345-28348, 2000.
Chao et al., "Flavopiridol Inactivates P-TEFb and Blocks Most RNA Polymerase II Transcription in Vivo," *The Journal of Biological Chemistry* 276:31793-31799, 2001.
Chen et al., "Caspase cleavage of $Bim_{EL}$ triggers a positive feedback amplification of apoptotic signaling," *PNAS* 101(5):1235-1240, 2004.
Chen et al., "Mcl-1 Down-regulation Potentiates ABT-737 Lethality by Cooperatively Inducing Bak Activation and Bax Translocation," *Cancer Res* 67(2):782-791, 2007.
Chen et al., "Transcription inhibition by flavopiridol: mechanism of chronic lymphocytic leukemia cell death," *Blood* 106:2513-2519, 2005.
Chen et al., "Differential Targeting of Prosurvival Bcl-2 Proteins by Their BH3-Only Ligands Allows Complementary Apoptotic Function," *Molecular Cell* 17:393-403, 2005.
Chen et al., "Mechanism of action of SNS-032, a novel cyclin-dependent kinase inhibitor in chronic lymphocytic leukemia," *Blood* 113:4637-4645, 2009.
Cheng et al., "Bax-independent inhibition of apoptosis by $Bcl-X_L$," *Nature* 379:554-556, 1996.
Cheng et al., "BCL-2, $BCL-X_L$ Sequester BH3 Domain-Only Molecules Preventing BAX- and BAK-Mediated Mitochondrial Apoptosis," *Molecular Cell* 8:705-711, 2001.
Cheson et al., "National Cancer Institute-Sponsored Working Group Guidelines for Chronic Lymphocytic Leukemia: Revised Guidelines for Diagnosis and Treatment," *Blood* 87:4990-4997, 1996.
Chipuk et al., "Direct Activation of Bax by p53 Mediates Mitochondrial Membrane Permeabilization and Apoptosis," *Science* 303:1010-1014, 2004.
Chittenden et al., "A conserved domain in Bak, distinct from BH1 and BH2, mediates cell death and protein binding functions," *The EMBO Journal* 14(22):5589-5596, 1995.
Chittenden et al., "Induction of apoptosis by the Bcl-2 homologue Bak," *Nature* 374:733-736, 1995.
Chonghaile et al., "Mitochondrial Apoptotic Priming Measured by BH3 Profiling Regulates Clinical Response to Chemotherapy in Myeloma and Acute Lymphoblastic Leukemia and Explains Therapeutic Index," *Blood* 118:1442, 2011. (6 pages).
Chonghaile et al., "Pretreatment Mitochondrial Priming Correlates with Clinical Response to Cytotoxic Chemotherapy," *Science* 334:1129-1133, 2011.
Chonghaile et al., "Supporting Online Material for: Pretreatment Mitochondrial Priming Correlates with Clinical Response to Cytotoxic Chemotherapy," *Science* 334:1129-1133, 2011. (36 pages).
Chonghaile et al., "Mimicking the BH3 domain to kill cancer cells," *Oncogene* 27:S149-S157, 2009.

Choudhary et al., "MCL-1 and BCL-xL-dependent resistance to the BCL-2 inhibitor ABT-199 can be overcome by preventing PI3K/AKT/mTOR activation in lymphoid malignancies," *Cell Death and Disease* 6:e1593, 2015. (12 pages).
Cole et al., "The EBV-Hybridoma Technique and Its Application to Human Lung Cancer," in Reisfeld et al. (eds.), *Monoclonal Antibodies and Cancer Therapy*, Alan R. Liss, Inc., New York, New York, USA, 1985, pp. 77-96.
Conaway et al., "The Mediator Complex and Transcription Elongation," *Biochim Biophys Acta* 1829:69-75, 2013. (16 pages).
Cory et al., "The BCL2 Family: Regulators of the Cellular Life-Or-Death Switch," *Nature Reviews Cancer* 2:647-656, 2002.
Cosulich et al., "Regulation of apoptosis by BH3 domains in a cell-free system," *Current Biology* 7:913-920, 1997.
Cote et al., "Generation of human monoclonal antibodies reactive with cellular antigens," *Proc. Natl. Acad. Sci. USA* 80:2026-2030, 1983.
Czabotar et al., "Bax activation by Bim?" *Cell Death and Differentiation* 16:1187-1191, 2009.
Czabotar et al., "Structural insights into the degradation of Mcl-1 induced by BH3 domains," *PNAS* 104:6217-6222, 2007.
Czech et al., "Antitumoral activity of flavone L 86-8275," *International Journal of Oncology* 6:31-36, 1995.
Daigle et al., "Potent inhibition of DOT1L as treatment of MLL-fusion leukemia," *Blood* 122(6):1017-1025, 2013.
Danial et al., "Cell Death: Critical Control Points," *Cell* 116:205-219, 2004.
Davids et al., "BH3 Profiling Demonstrates That Restoration of Apoptotic Priming Contributes to Increased Sensitivity to PI3K Inhibition in Stroma-Exposed Chronic Lymphocytic Leukemia Cells," *Blood* 118:974, 2011. (6 pages).
Davids et al., "Targeting the B-Cell Lymphoma/Leukemia 2 Family in Cancer," *Journal of Clinical Oncology* 30(25):3127-3135, 2012.
Degrado, "Design of Peptides and Proteins," *Advances in Protein Chemistry* 39:51-124, 1988.
Deng et al., "BH3 Profiling Identifies Three Distinct Classes of Apoptotic Blocks to Predict Response to ABT-737 and Conventional Chemotherapeutic Agents," *Cancer Cell* 12:171-185, 2007.
Derenne et al., "Antisense strategy shows that Mcl-1 rather than Bcl-2 or $Bcl-_{XL}$ is an essential survival protein in human myeloma cells," *Blood* 100:194-199, 2002.
Desagher et al., "Bid-induced Conformational Change of Bax Is Responsible for Mitochondrial Cytochrome c Release during Apoptosis," *The Journal of Cell Biology* 144(5):891-901, 1999.
Dettman et al., "Context Dependent Diagnosis Test for Guiding Cancer Treatment," U.S. Appl. No. 62/102,499, filed Jan. 12, 2015, 71 pages.
Dettman et al., "Abstract 3400: Mitochondrial profiling in AML patients treated with an Alvocidib containing regimen reveals MCL1 dependency in responder bone marrow," *Cancer Res* 75:3400, 2015. (2 pages).
Di Lisa et al., "Mitochondrial Function and Cell Injury in Single Cardiac Myocytes Exposed to Anoxia and Reoxygenation," *Transplantation Proceedings* 27(5):2829-2830, 1995.
Di Lisa et al., "Mitochondrial membrane potential in single living adult rat cardiac myocytes exposed to anoxia or metabolic inhibition," *Journal of Physiology* 486.1:1-13, 1995.
Diamandis et al. (eds.), *Immunoassay*, Academic Press, San Diego, CA, 1996, 613 pages.
Dinnen et al., "Redirecting Apoptosis to Aponecrosis Induces Selective Cytotoxicity to Pancreatic Cancer Cells through Increased ROS, Decline in ATP Levels, and VDAC," *Mol Cancer Ther* 12(12):2792-2803, 2013.
Döhner et al., "Genomic Aberrations and Survival in Chronic Lymphocytic Leukemia," *The New England Journal of Medicine* 343:1910-1916, 2000.
Egle et al., "Bim is a suppressor of Myc-induced mouse B cell leukemia," *PNAS* 101(16):6164-6169, 2004.
Ellerby et al., "Anti-cancer activity of targeted pro-apoptotic peptides," *Nature Medicine* 5(9):1032-1038, 1999.
Elliott et al., "Intercellular Trafficking and Protein Delivery by a Herpesvirus Structural Protein," *Cell* 88:223-233, 1997.

(56) References Cited

OTHER PUBLICATIONS

Elston et al., "Pathological prognostic factors in breast cancer. I. The value of histological grade in breast cancer: experience from a large study with long-term follow-up," *Histopathology* 19:403-410, 1991.
Ember et al., "Acetyl-lysine Binding Site of Bromodomain-Containing Protein 4 (BRD4) Interacts with Diverse Kinase Inhibitors," *ACS Chem. Biol.* 9:1160-1171, 2014.
Eskes et al., "Bid Induces the Oligomerization and Insertion of Bax into the Outer Mitochondrial Membrane," *Molecular and Cellular Biology* 20(3):929-935, 2000.
Falkenberg et al., "Histone deacetylases and their inhibitors in cancer, neurological diseases and immune disorders," *Nature Reviews Drug Discovery* 13:673-691, 2014.
Fanidi et al., "Cooperative interaction between c-myc and bcl-2 proto-oncogenes," *Nature* 359:554-556, 1992.
Filippakopoulos et al., "Selective inhibition of BET bromodomains," *Nature* 468:1067-1073, 2010.
Filippakopoulos et al., "Targeting bromodomains: epigenetic readers of lysine acetylation," *Nature Reviews Drug Discovery* 13:337-356, 2014.
Fish et al., "Identification of a Chemical Probe for Bromo and Extra C-Terminal Bromodomain Inhibition through Optimization of a Fragment-Derived Hit," *J. Med. Chem.* 55:9831-9837, 2012.
Fiskum et al., "[21] Apoptosis-Related Activities Measured with Isolated Mitochondria and Digitonin-Permeabilized Cells," *Methods in Enzymology* 322:222-234, 2000.
Fiskus et al., "Highly Active Combination of BRD4 Antagonist and Histone Deacetylase Inhibitor against Human Acute Myelogenous Leukemia Cells," *Molecular Cancer Therapeutics* 13:1142-1154, 2014.
Flinn et al., "Flavopiridol administered as a 24-hour continuous infusion in chronic lymphocytic leukemia lacks clinical activity," *Leukemia Research* 29:1253-1257, 2005.
Foight et al., "Designed BH3 Peptides with High Affinity and Specificity for Targeting Mcl-1 in Cells," *ACS Chem. Biol.* 9:1962-1968, 2014.
Frankel et al., "Activity of synthetic peptides from the Tat protein of human immunodeficiency virus type 1," *Proc. Natl. Acad. Sci. USA* 86:7397-7401, 1989.
Friedman et al., "Precision medicine for cancer with next-generation functional diagnostics," *Nat Rev Cancer* 15(12):747-756, 2015. (26 pages).
Fuchs et al., "Pathway for Polyarginine Entry into Mammalian Cells," *Biochemistry* 43(9):2438-2444, 2004. (15 pages).
Fukui et al., "The Analysis of the Effect of JQ1 and Flavopiridol on Chondrocytes under Inflammatory Stimuli," *ORS 2014 Annual Meeting*, New Orleans, Louisiana, USA, Mar. 15-18, 2014, 4 pages.
Futaki et al., "Arginine-rich Peptides: An Abundant Source of Membrane-Permeable Peptides Having Potential as Carriers for Intracellular Protein Delivery," *The Journal of Biological Chemistry* 276(8):5836-5840, 2001.
Geserick et al., "The ratio of Mcl-1 and Noxa determines ABT737 resistance in squamous cell carcinoma of the skin," *Cell Death and Disease* 5:e1412, 2014. (14 pages).
Giles et al., "A Phase I Study of Intravenous LBH589, a Novel Cinnamic Hydroxamic Acid Analogue Histone Deacetylase Inhibitor, in Patients with Refractory Hematologic Malignancies," *Clin Cancer Res* 12(15):4628-4635, 2006.
Gojo et al., "The Cyclin-dependent Kinase Inhibitor Flavopiridol Induces Apoptosis in Multiple Myeloma Cells through Transcriptional Repression and Down-Regulation of Mcl-1," *Clinical Cancer Research* 8:3527-3538, 2002.
Goldsmith et al., "BH3 peptidomimetics potently activate apoptosis and demonstrate single agent efficacy in neuroblastoma," *Oncogene* 25:4525-4533, 2006.
Göttlicher et al., "Valproic acid defines a novel class of HDAC inhibitors inducing differentiation of transformed cells," *The EMBO Journal* 20(24):6969-6978, 2001.
Green, "Life, Death, BH3 Profiles, and the Salmon Mousse," *Cancer Cell* 12:97-99, 2007.
Green et al., "A matter of life and death," *Cancer Cell* 1:19-30, 2002.
Green et al., "The Pathophysiology of Mitochondrial Cell Death," *Science* 305:626-629, 2004.
Griffiths et al., "Cell Damage-induced Conformational Changes of the Pro-Apoptotic Protein Bak In Vivo Precede the Onset of Apoptosis," *The Journal of Cell Biology* 144(5):903-914, 1999.
Gross et al., "Enforced dimerization of BAX results in its translocation, mitochondrial dysfunction and apoptosis," *The EMBO Journal* 17(14):3878-3885, 1998.
Gruber et al., "Efficient Tumor Cell Lysis Mediated by a Bispecific Single Chain Antibody Expressed in *Escherichia coli*," *Journal of Immunology* 152:5368-5374, 1994.
Guha, "Cyclin-dependent kinase inhibitors move into Phase III," *Nature Reviews Drug Discovery* 11:892-894, 2012.
Gul et al., "Apoptotic blocks and chemotherapy resistance: strategies to identify Bcl-2 protein signatures," *Briefings in Functional Genomics and Proteomics* 7(1):27-34, 2008.
Hanahan, "Heritable formation of pancreatic β-cell tumours in transgenic mice expressing recombinant insulin/simian virus 40 oncogenes," *Nature* 315:115-122, 1985.
Hanahan et al., "The Hallmarks of Cancer," *Cell* 100:57-70, 2000.
Hans et al., "β-Carbolines induce apoptosis in cultured cerebellar granule neurons via the mitochondrial pathway," *Neuropharmacology* 48:105-117, 2005.
Harada et al., "Survival factor-induced extracellular signal-regulated kinase phosphorylates BIM, inhibiting its association with BAX and proapoptotic activity," *PNAS* 101(43):15313-15317, 2004.
Hemann et al., "Suppression of tumorigenesis by the p53 target PUMA," *PNAS* 101(25):9333-9338, 2004.
Hemann et al., "Evasion of the p53 tumour surveillance network by tumour-derived MYC mutants," *Nature* 436(7052):807-811, 2005. (13 pages).
Hengartner et al., "C. elegans Cell Survival Gene ced-9 Encodes a Functional Homolog of the Mammalian Proto-Oncogene bcl-2," *Cell* 76:665-676, 1994.
Hirst et al., "Application of Non-Parametric Regression to Quantitative Structure-Activity Relationships," *Bioorganic & Medicinal Chemistry* 10:1037-1041, 2002.
Hnisz et al., "Super-Enhancers in the Control of Cell Identity and Disease," *Cell* 155:934-947, 2013.
Holinger et al., "Bak BH3 Peptides Antagonize Bcl-$X_L$ Function and Induce Apoptosis through Cytochrome c-independent Activation of Caspases," *The Journal of Biological Chemistry* 274(19):13298-13304, 1999.
Holliger et al., ""Diabodies": Small bivalent and bispecific antibody fragments," *Proc. Natl. Acad. Sci. USA* 90:6444-6448, 1993.
Hoogenboom et al., "By-passing Immunisation—Human Antibodies from Synthetic Repertoires of Germline $V_H$ Gene Segments Rearranged in Vitro," *J. Mol. Biol.* 227:381-388, 1992.
Hopp et al., "Prediction of protein antigenic determinants from amino acid sequences," *Proc. Natl. Acad. Sci. USA* 78(6):3824-3828, 1981.
Hoppel et al., "The Action of Digitonin on Rat Liver Mitochondria," *Biochem J.* 107:367-375, 1968.
Hsu et al., "Nonionic Detergents Induce Dimerization among Members of the Bcl-2 Family," *The Journal of Biological Chemistry* 272(21):13829-13834, 1997.
Huang et al., "BH3-Only Proteins—Essential Initiators of Apoptotic Cell Death," *Cell* 103:839-842, 2000.
Huse et al., "Generation of a Large Combinatorial Library of the Immunoglobulin Repertoire in Phage Lambda," *Science* 246:1275-1281, 1989.
Innocenti et al., "Flavopiridol Metabolism in Cancer Patients Is Associated with the Occurrence of Diarrhea," *Clinical Cancer Research* 6:3400-3405, 2000.
Inohara et al., "harakiri, a novel regulator of cell death, encodes a protein that activates apoptosis and interacts selectively with survival-promoting proteins Bcl-2 and Bcl-$X_L$," *The EMBO Journal* 16(7):1686-1694, 1997.
Ishizawa et al., "Mitochondrial Profiling of Acute Myeloid Leukemia in the Assessment of Response to Apoptosis Modulating Drugs," *PLoS One* 10(9):e0138377, 2015. (16 pages).

(56) References Cited

OTHER PUBLICATIONS

Jackson et al., "Heat shock induces the release of fibroblast growth factor 1 from NIH 3T3 cells," *Proc. Natl. Acad. Sci. USA* 89:10691-10695, 1992.
Jameson et al., "A rationally designed CD4 analogue inhibits experimental allergic encephalomyelitis," *Nature* 368:744-746, 1994.
Jones et al., "Replacing the complementarity-determining regions in a human antibody with those from a mouse," *Nature* 321:522-525, 1986.
Jonkers et al., "Oncogene addiction: Sometimes a temporary slavery," *Cancer Cell* 6:535-538, 2004.
Kasper et al., "Targeting MCL-1 sensitizes FLT3-ITD-positive leukemias to cytotoxic therapies," *Blood Cancer J* 2: 10 pages, 2012.
Keating et al., "Results of First Salvage Therapy for Patients Refractory to a Fludarabine Regimen in Chronic Lymphocytic Leukemia," *Leukemia and Lymphoma* 43(9):1755-1762, 2002.
Keating et al., "Therapeutic role of alemtuzumab (Campath-1H) in patients who have failed fludarabine: results of a large international study," *Blood* 99:3554-3561, 2002.
Kelekar et al., "Bcl-2-family proteins: the role of the BH3 domain in apoptosis," *Trends in Cell Biology* 8:324-330, 1998.
Kelekar et al., "Bad Is a BH3 Domain-Containing Protein That Forms an Inactivating Dimer with Bcl-$X_L$," *Molecular and Cellular Biology* 17(12):7040-7046, 1997.
KG-1, ATCC® CCL-246™, ATCC Product Sheet, May 31, 2013, 3 pages.
Kitada et al., "Protein kinase inhibitors flavopiridol and 7-hydroxystaurosporine down-regulate antiapoptosis proteins in B-cell chronic lymphocytic leukemia," *Blood* 96:393-397, 2000.
Köhler et al., "Continuous cultures of fused cells secreting antibody of predefined specificity," *Nature* 256:495-497, 1975.
König et al., "The Novel Cyclin-Dependent Kinase Inhibitor Flavopiridol Downregulates Bcl-2 and Induces Growth Arrest and Apoptosis in Chronic B-Cell Leukemia Lines," *Blood* 90:4307-4312, 1997.
Korsmeyer et al., "Pro-apoptotic cascade activates BID, which oligomerizes BAK or BAX into pores that result in the release of cytochrome c," *Cell Death and Differentiation* 7:1166-1173, 2000.
Kozbor et al., "The production of monoclonal antibodies from human lymphocytes," *Immunology Today* 4(3):72-79, 1983.
Kryštof et al., "Cyclin-Dependent Kinase Inhibitors as Anticancer Drugs," *Current Drug Targets* 11:291-302, 2010.
Kuwana et al., "Bid, Bax, and Lipids Cooperate to Form Supramolecular Openings in the Outer Mitochondrial Membrane," *Cell* 111:331-342, 2002.
Kuwana et al., "BH3 Domains of BH3-Only Proteins Differentially Regulate Bax-Mediated Mitochondrial Membrane Permeabilization Both Directly and Indirectly," *Molecular Cell* 17:525-535, 2005.
Kyte et al., "A Simple Method for Displaying the Hydropathic Character of a Protein," *J. Mol. Biol.* 157:105-132, 1982.
La Vieira et al., "Cell permeable BH3-peptides overcome the cytoprotective effect of Bcl-2 and Bcl-$X_L$," *Oncogene* 21:1963-1977, 2002.
Labi et al., "Targeting the Bcl-2-regulated apoptosis pathway by BH3 mimetics: a breakthrough in anticancer therapy?," *Cell Death and Differentiation* 15:977-987, 2008.
Leo et al., "Characterization of the Antiapoptotic Bcl-2 Family Member Myeloid Cell Leukemia-1 (Mcl-1) and the Stimulation of Its Message by Gonadotropins in the Rat Ovary," *Endocrinology* 140(12):5469-5477, 1999.
Letai, "The BCL-2 network: Mechanistic insights and therapeutic potential," *Drug Discovery Today: Disease Mechanisms* 2(2):145-151, 2005.
Letai et al., "Antiapoptotic BCL-2 is required for maintenance of a model leukemia," *Cancer Cell* 6:241-249, 2004.
Letai, "Perturbing cancer cell mitochondria to learn how to kill cancer with BH3 profiling," Dana-Farber Cancer Institute, Broad Institute, *Cell Circuits and Epigenomics*, Jul. 28, 2014, 47 pages.
Letai, "BH3 domains as BCL-2 inhibitors: prototype cancer therapeutics," *Expert Opin. Biol. Ther.* 3:293-304, 2003.
Letai et al., "Distinct BH3 domains either sensitize or activate mitochondrial apoptosis, serving as prototype cancer therapeutics," *Cancer Cell* 2:183-192, 2002.
Li et al., "tsg101: A Novel Tumor Susceptibility Gene Isolated by Controlled Homozygous Functional Knockout of Allelic Loci in Mammalian Cells," *Cell* 85:319-329, 1996.
Li et al., "Cleavage of BID by Caspase 8 Mediates the Mitochondrial Damage in the Fas Pathway of Apoptosis," *Cell* 94:491-501, 1998.
Li et al., "Endonuclease G is an apoptotic DNase when released from mitochondria," *Nature* 412:95-99, 2001.
Lin et al., "Seventy-Two Hour Continuous Infusion Flavopiridol in Relapsed and Refractory Mantle Cell Lymphoma," *Leukemia & Lymphoma* 43:793-797, 2002.
Lin et al., "Flavopiridol given as a 30-min intravenous (IV) bolus followed by 4-hr continuous IV infusion (CIVI) results in clinical activity and tumor lysis in refractory chronic lymphocytic leukemia (CLL)," *Journal of Clinical Oncology, 2004 ASCO Annual Meeting Proceedings (Post-Meeting Edition)* 22(14S):8564, 2004. (1 page).
Liu et al., "Bax conformational change is a crucial step for PUMA-mediated apoptosis in human leukemia," *Biochemical and Biophysical Research Communications* 310:956-962, 2003.
Liu et al., "BH3-based Fusion Artificial Peptide Induces Apoptosis and Targets Human Colon Cancer," *Molecular Therapy* 17:1509-1516, 2009.
Liu et al., "CDKI-71, a novel CDK9 inhibitor, is preferentially cytotoxic to cancer cells compared to flavopiridol," *Int. J. Cancer* 130:1216-1226, 2012.
Lonberg et al., "Antigen-specific human antibodies from mice comprising four distinct genetic modifications," *Nature* 368:856-859, 1994.
Long et al., "Optimization and validation of mitochondria-based functional assay as a useful tool to identify BH3-like molecules selectively targeting anti-apoptotic Bcl-2 proteins," *BMC Biotechnology* 13:45, 2013. (10 pages).
Lovén et al., "Selective Inhibition of Tumor Oncogenes by Disruption of Super-Enhancers," *Cell* 153:320-334, 2013. (27 pages).
Lozanski et al., "Alemtuzumab is an effective therapy for chronic lymphocytic leukemia with p53 mutations and deletions," *Blood* 103:3278-3281, 2004.
Luo et al., "Bid, a Bcl2 Interacting Protein, Mediates Cytochrome c Release from Mitochondria in Response to Activation of Cell Surface Death Receptors," *Cell* 94:481-490, 1998.
Lutter et al., "The pro-apoptotic Bcl-2 family member tBid localizes to mitochondrial contact sites," *BMC Cell Biology* 2:22, 2001. (9 pages).
Marani et al., "Identification of Novel Isoforms of the BH3 Domain Protein Bim Which Directly Activate Bax to Trigger Apoptosis," *Molecular and Cellular Biology* 22(11):3577-3589, 2002.
Marks et al., "By-passing Immunization: Human Antibodies from V-gene Libraries Displayed on Phage," *J. Mol. Biol.* 222:581-597, 1991.
Marks et al., "By-Passing Immunization: Building High Affinity Human Antibodies by Chain Shuffling," *Nature Bio/Technology* 10:779-783, 1992.
Martin, "Opening the Cellular Poison Cabinet," *Science* 330:1330-1331, 2010.
Mason et al., "The Hypogonadal Mouse: Reproductive Functions Restored by Gene Therapy," *Science* 234:1372-1378, 1986.
Matsushita et al., "A High-Efficiency Protein Transduction System Demonstrating the Role of PKA in Long-Lasting Long-Term Potentiation," *The Journal of Neuroscience* 21(16):6000-6007, 2001.
Matsuzaki, "Why and how are peptide-lipid interactions utilized for self defence?," *Biochem. Soc. Transactions* 29:598-601, 2001.
McDonnell et al., "bcl-2-Immunoglobulin Transgenic Mice Demonstrate Extended B Cell Survival and Follicular Lymphoproliferation," *Cell* 57:79-88, 1989.
Means et al., *Chemical Modification of Proteins*, Holden-Day, Inc., San Francisco, California, USA, 1974, "Modifications to change properties," Chapter 3, pp. 35-54. (22 pages).
Miller et al., "Therapeutic Strategies to Enhance the Anticancer Efficacy of Histone Deacetylase Inhibitors," *Journal of Biomedicine and Biotechnology* 2011:514261, 2011. (17 pages).

(56) References Cited

OTHER PUBLICATIONS

Milstein et al., "Hybrid hybridomas and their use in immunohistochemistry," *Nature* 305:537-540, 1983.
Molassiotis et al., "Use of complementary and alternative medicine in cancer patients: A European Survery," *Annals of Oncology* 16:655-663, 2005.
Montero et al., "Drug-Induced Death Signaling Strategy Rapidly Predicts Cancer Response to Chemotherapy," *Cell* 160:977-989, 2015. (14 pages).
Moore et al., "Chronic lymphocytic leukemia requires BCL2 to sequester prodeath BIM, explaining sensitivity to BCL2 antagonist ABT-737," *The Journal of Clinical Investigation* 117(1):112-121, 2007.
Moore et al., "BH3 profiling—measuring integrated function of the mitochondrial apoptotic pathway to predict cell fate decisions," *Cancer Lett* 332:202-205, 2013. (10 pages).
Morrison, "Success in specification," *Nature* 368:812-813, 1994.
Muchmore et al., "X-ray and NMR structure of human Bcl-$X_L$, an inhibitor of programmed cell death," *Nature* 381:335-341, 1996. (16 pages).
Munson et al., "LIGAND: A Versatile Computerized Approach for Characterization of Ligand-Binding Systems," *Analytical Biochemistry* 107:220-239, 1980. (22 pages).
Murthi et al., "Structure-Activity Relationship Studies of Flavopiridol Analogues," *Bioorganic & Medicinal Chemistry Letters* 10:1037-1041, 2000.
Naik et al., "An Antiinflammatory Cum Immunomodulatory Piperidinylbenzopyranone From *Dysoxylum binectariferum*: Isolation, Structure and Total Synthesis," *Tetrahedron* 44:2081-2086, 1988.
Nakano et al., "PUMA, a Novel Proapoptotic Gene, Is Induced by p53," *Molecular Cell* 7:683-694, 2001.
Narita et al., "Bax interacts with the permeability transition pore to induce permeability transition and cytochrome c release in isolated mitochondria," *Proc. Natl. Acad. Sci. USA* 95:14681-14686, 1998.
Neuberger, "Generating high-avidity human Mabs in mice," *Nature Biotechnology* 14:826, 1996.
Noel et al., "Abstract C244: Development of the BET bromodomain inhibitor OTX015," *Proceedings of the AACR-NCI-EORTC International Conference: Molecular Targets and Cancer Therapeutics*, Oct. 19-23, 2013, Boston, MA, Philadelphia, PA: AACR; *Mol Cancer Ther* 12(11 Suppl): Abstract No. C244, 2013. (4 pages).
O'Brien et al., "Phase I to II Multicenter Study of Oblimersen Sodium, a Bcl-2 Antisense Oligonucleotide, in Patients With Advanced Chronic Lymphocytic Leukemia," *Journal of Clinical Oncology* 23(30):7697-7702, 2005.
O'Connor et al., "Bim: a novel member of the Bcl-2 family that promotes apoptosis," *The EMBO Journal* 17(2):384-395, 1998.
Oda et al., "Noxa, a BH3-Only Member of the Bcl-2 Family and Candidate Mediator of p53-Induced Apoptosis," *Science* 288:1053-1058, 2000.
Oh et al., "Conformational Changes in BID, a Pro-apoptotic BCL-2 Family Member, upon Membrane Binding," *The Journal of Biological Chemistry* 280(1):753-767, 2005.
Oltersdorf et al., "An inhibitor of Bcl-2 family proteins induces regression of solid tumours," *Nature* 435:677-681, 2005.
Opferman et al., "Development and maintenance of B and T lymphocytes requires antiapoptotic MCL-1," *Nature* 426:671-676, 2003.
Oscier et al., "Multivariate analysis of prognostic factors in CLL: clinical stage, IGVH gene mutational status, and loss or mutation of the p53 gene are independent prognostic factors," *Blood* 100:1177-1184, 2002.
Paoluzzi et al., "The BH3-only mimetic ABT-737 synergizes the antineoplastic activity of proteasome inhibitors in lymphoid malignancies," *Blood* 112:2906-2916, 2008.
Paquin et al., "Design and synthesis of 4-[(s-triazin-2-ylamino)methyl]-N-(2-aminophenyl)-benzamides and their analogues as a novel class of histone deacetylase inhibitors," *Bioorganic & Medicinal Chemistry Letters* 18:1067-1071, 2008.

Parker et al., "Early Induction of Apoptosis in Hematopoietic Cell Lines After Exposure to Flavopiridol," *Blood* 91:458-465, 1998.
Parry et al., "Dinaciclib (SCH 727965), a Novel and Potent Cyclin-Dependent Kinase Inhibitor," *Mol Cancer Ther* 9(8):2344-2353, 2010.
Paruch et al., "Discovery of Dinaciclib (SCH 727965): A Potent and Selective Inhibitor of Cyclin-Dependent Kinases," *ACS Med. Chem. Lett* 1:204-208, 2010.
Perkins et al., "Frequency and Type of Serious Infections in Fludarabine-Refractory B-Cell Chronic Lymphocytic Leukemia and Small Lymphocytic Lymphoma," *Cancer* 94:2033-2039, 2002.
Picaud et al., "PFI-1, a Highly Selective Protein Interaction Inhibitor, Targeting BET Bromodomains," *Cancer Res* 73(11):3336-3346, 2013.
Piekarz et al., "Inhibitor of histone deacetylation, depsipeptide (FR901228), in the treatment of peripheral and cutaneous T-cell lymphoma: a case report," *Blood* 98:2865-2868, 2001.
Pierceall et al., "BH3 Profiling Discriminates Response to Cytarabine-Based Treatment of Acute Myelogenous Leukemia," *Molecular Cancer Therapeutics* 12(12):2940-2949, 2013.
Pierceall et al., "Mcl-1 Dependence Predicts Response to Vorinostat and Gemtuzumab Ozogamicin in Acute Myeloid Leukemia," *Leuk Res* 38:564-568, 2014. (13 pages).
Pierceall et al., "Mitochondrial Priming of Chronic Lymphocytic Leukemia Patients Associates Bcl-$X_L$ Dependence with Alvocidib Response," *Leukemia* 28:2251-2254, 2014. (7 pages).
Pinkert et al., "An albumin enhancer located 10 kb upstream functions along with its promoter to direct efficient, liver-specific expression in transgenic mice," *Genes & Development* 1:268-276, 1987.
Plumb et al., "Pharmacodynamic Response and Inhibition of Growth of Human Tumor Xenografts by the Novel Histone Deacetylase Inhibitor PXD101," *Molecular Cancer Therapeutics* 2:721-728, 2003.
Pode-Shakked et al., "Development tumourigenesis: NCAM as a putative marker for the malignant renal stem/progenitor cell population," *J. Cell. Mol. Med.* 13(8B):1792-1808, 2009.
Polster et al., "BH3 Death Domain Peptide Induces Cell Type-selective Mitochondrial Outer Membrane Permeability," *The Journal of Biological Chemistry* 276:37887-37894, 2001.
Presta, "Antibody engineering," *Current Opinion in Structural Biology* 2:593-596, 1992.
Pritzker, "Cancer Biomarkers: Easier Said Than Done," *Clinical Chemistry* 48(8):1147-1150, 2002.
Putcha et al., "Induction of BIM, a Proapoptotic BH3-Only BCL-2 Family Member, Is Critical for Neuronal Apoptosis," *Neuron* 29:615-628, 2001.
Puthalakath et al., "The Proapoptotic Activity of the Bcl-2 Family Member Bim is Regulated by Interaction with the Dynein Motor Complex," *Molecular Cell* 3:287-296, 1999.
Puthalakath et al., "Bmf: A Proapoptotic BH3-Only Protein Regulated by Interaction with the Myosin V Actin Motor Complex, Activated by Anoikis," *Science* 293:1829-1832, 2001.
Puthalakath et al., "Keeping killers on a tight leash: transcriptional and post-translational control of the pro-apoptotic activity of BH3-only proteins," *Cell Death and Differentiation* 9:505-512, 2002.
Quinsay et al., "Abstract 1783: Pro-Apoptotic Bnip3 Mediates Permeabilization of Mitochondria and Release of Cytochrome c via a Novel Mechanism," *Circulation* 118:S388. 2008. (5 pages).
Raff, "Social controls on cell survival and cell death," *Nature* 356:397-400, 1992.
Rassenti et al., "ZAP-70 Compared with Immunoglobulin Heavy-Chain Gene Mutation Status as a Predictor of Disease Progression in Chronic Lymphocytic Leukemia," *N. Engl. J. Med.* 351:893-901, 2004.
Ray et al., "BNIP3 Heterodimerizes with Bcl-2/Bcl-$X_L$ and Induces Cell Death Independent of a Bcl-2 Homology 3 (BH3) Domain at Both Mitochondrial and Nonmitochondrial Sites," *The Journal of Biological Chemistry* 275(2):1439-1448, 2000.
Raychaudhuri, "Low probability Bid-Bax reaction generates heterogeneity in apoptosis resistance of cancer and cancer stem cells," arXiv:1108.2091 [q-bio.MN], 2011, 17 pages.

(56) References Cited

OTHER PUBLICATIONS

Ren et al., "BID, BIM, and PUMA Are Essential for Activation of the BAX- and BAK-Dependent Cell Death Program," *Science* 330:1390-1393, 2010.
Rezaei et al., "Leukemia markers expression of peripheral blood vs. bone marrow blasts using flow cytometry," *Med Sci. Monit* 9:CR359-CR362, 2003.
Richon et al., "A class of hybrid polar inducers of transformed cell differentiation inhibits histone deacetylases," *Proc. Natl. Acad. Sci. USA* 95:3003-3007, 1998.
Riechmann et al., "Reshaping human antibodies for therapy," *Nature* 332:323-327, 1988.
Rollins-Raval et al., "The value of immunohistochemistry for CD14, CD123, CD33, myeloperoxidase and CD68R in the diagnosis of acute and chronic myelomonocytic leukaemias," *Histopathology* 60:933-942, 2012.
Rothbard et al., "Conjugation of arginine oligomers to cyclosporin A facilitates topical delivery and inhibition of inflammation," *Nature Medicine* 6(11):1253-1257, 2000.
Rudek et al., "Clinical Pharmacology of Flavopiridol Following a 72-Hour Continuous Infusion," *Ann Pharmacother* 37:1369-1374, 2003.
Ryan et al., "Heightened mitochondrial priming is the basis for apoptotic hypersensitivity of $CD4^+$ $CD8^+$ thymocytes," *PNAS* 107(29): 12895-12900, 2010.
Ryan et al., "BH3 Profiling in Whole Cells by Fluorimeter or FACS," *Methods* 61:156-164, 2013. (22 pages).
Saito et al., "A synthetic inhibitor of histone deacetylase, MS-27-275, with marked in vivo antitumor activity against human tumors," *Proc. Natl. Acad. Sci. USA* 96:4592-4597, 1999.
Samson et al., "A 35 Amino Acid Fragment of Leptin Inhibits Feeding in the Rat," *Endocrinology* 137(11):5182-5185, 1996.
Sattler et al., "Structure of Bcl-$x_L$-Bak Peptide Complex: Recognition Between Regulators of Apoptosis," *Science* 275:983-986, 1997.
Sausville et al., "Inhibition of CDKs as a Therapeutic Modality," *Ann. NY Acad. of Sci.* 910:207-222, 2000.
Schimmer et al., "The BH3 domain of BAD fused to the Antennapedia peptide induces apoptosis via its alpha helical structure and independent of Bcl-2," *Cell Death and Differentiation* 8:725-733, 2001.
Schwartz et al., "Phase II Study of the Cyclin-Dependent Kinase Inhibitor Flavopiridol Administered to Patients With Advanced Gastric Carcinoma," *J Clin Oncol* 19:1985-1992, 2001.
Seal et al., "Identification of a novel series of BET family bromodomain inhibitors: Binding mode and profile of I-BET151 (GSK1210151A)," *Bioorganic & Medicinal Chemistry Letters* 22:2968-2972, 2012.
Sedlacek et al., "Flavopiridol (L86 8275; NSC 649890), a new kinase inhibitor for tumor therapy," *International Journal of Oncology* 9:1143-1168, 1996.
Sen et al., "Artemisinin triggers induction of cell-cycle arrest and apoptosis in *Leishmania donovani* promastigotes," *Journal of Medical Microbiology* 56:1213-1218, 2007.
Senderowicz et al., "Phase I Trial of Continuous Infusion Flavopiridol, a Novel Cyclin-Dependent Kinase Inhibitor, in Patients With Refractory Neoplasms," *J. Clin Oncol* 16:2986-2999, 1998.
Senderowicz et al., "Preclinical and Clinical Development of Cyclin-Dependent Kinase Modulators," *J Natl Cancer Inst* 92:376-387, 2000.
Senderowicz, "Flavopiridol: the first cyclin-dependent kinase inhibitor in human clinical trials," *Investigational New Drugs* 17:313-320, 1999.
Shalaby et al., "Development of Humanized Bispecific Antibodies Reactive with Cytotoxic Lymphocytes and Tumor Cells Overexpressing the HER2 Protooncogene," *J. Exp. Med.* 175:217-225, 1992.
Shangary et al., "Peptides Derived from BH3 Domains of Bcl-2 Family Members: A Comparative Analysis of Inhibition of Bcl-2, Bcl-$X_L$ and Bax Oligomerization, Induction of Cytochrome c Release, and Activation of Cell Death," *Biochemistry* 41:9485-9495, 2002.

Shapiro et al., "A Phase II Trial of the Cyclin-dependent Kinase Inhibitor Flavopiridol in Patients with Previously Untreated Stage IV Non-Small Cell Lung Cancer," *Clinical Cancer Research* 7:1590-1599, 2001.
Shibue et al., "Differential contribution of Puma and Noxa in dual regulation of p53-mediated apoptotic pathways," *The EMBO Journal* 25:4952-4962, 2006.
Shimizu et al., "Proapoptotic BH3-only Bcl-2 family members induce cytochrome c release, but not mitochondrial membrane potential loss, and do not directly modulate voltage-dependent anion channel activity," *PNAS* 97:577-582, 2000.
Shopes, "A Genetically Engineered Human IgG Mutant With Enhanced Cytolytic Activity," *The Journal of Immunology* 148(9):2918-2922, 1992.
Sinicrope et al., "Proapoptotic Bad and Bid Protein Expression Predict Survival in Stages II and III Colon Cancers," *Clin Cancer Res* 14(13):4128-4133, 2008.
Sinicrope et al., "Prognostic Impact of Bim, Puma, and Noxa Expression in Human Colon Carcinomas," *Clin Cancer Res* 14(18):5810-5818, 2008.
Smith et al., "Enhancer biology and enhanceropathies," *Nature Structural & Molecular Biology* 21:210-219, 2014.
Smith et al., "An alvocidib-containing regimen is highly effective in AML patients through a mechanism dependent on MCL1 expression and function," *2015 ASCO Annual Meeting*, Abstract No. 7062, 2015. (3 pages).
Soltow et al., "Overexpression of CuZnSOD or MnSOD protects satellite cells from doxorubicin-induced apoptosis," *The FASEB Journal* 21(5): Abstract No. A449, 2007. (2 pages).
Song et al., "Carbon Monoxide Promotes Fas/CD95-induced Apoptosis in Jurkat Cells," *The Journal of Biological Chemistry* 279(43):44327-44334, 2004. (11 pages).
Song et al., "Carbon Monoxide Promotes Fas/CD95-induced Apoptosis in Jurkat Cells," *The Journal of Biological Chemistry* 279(43):44327-44334, 2004—"Additions and Correction," *The Journal of Biological Chemistry* 280(23):22555-22556, 2005. (3 pages).
Stevenson et al., "A chimeric antibody with dual Fc regions (bisFabFc) prepared by manipulations at the IgG hinge," *Anti-Cancer Drug Design* 3:219-230, 1989.
Stewart et al., "The MCL-1 BH3 Helix is an Exclusive MCL-1 inhibitor and Apoptosis Sensitizer," *Nat. Chem. Biol.* 6(8):595-601, 2010. (17 pages).
Sturm et al., "Mutation of p53 and consecutive selective drug resistance in B-CLL occurs as a consequence of prior DNA-damaging chemotherapy," *Cell Death and Differentiation* 10:477-484, 2003.
Sugiyama et al., "Activation of mitochondrial voltage-dependent anion channel by a pro-apoptotic BH3-only protein Bim," *Oncogene* 21:4944-4956, 2002.
Suzuki et al., "Possible Existence of Common Internalization Mechanisms among Arginine-rich Peptides," *The Journal of Biological Chemistry* 277(4):2437-2443, 2002.
Tahir et al., "Potential mechanisms of resistance to venetoclax and strategies to circumvent it," *BMC Cancer* 17:399, 2017. (10 pages).
Tan et al., "Phase I Clinical and Pharmacokinetic Study of Flavopiridol Administered as a Daily 1-Hour Infusion in Patients With Advanced Neoplasms," *J Clin Oncol* 20:4074-4082, 2002.
Taussig et al., "Anti-CD38 antibody-mediated clearance of human repopulating cells masks the heterogeneity of leukemia-initiating cells," *Blood* 112:568-575, 2008.
Terradillos et al., "Direct addition of BimL to mitochondria does not lead to cytochrome c release," *FEBS Letters* 522:29-34, 2002.
Theisen et al., "Reversible inhibition of lysine specific demethylase 1 is a novel anti-tumor strategy for poorly differentiated endometrial carcinoma," *BMC Cancer* 14:752, 2014. (12 pages).
Thomas et al., "Phase I clinical pharmacokinetic trial of the cyclin-dependent kinase inhibitor flavopiridol," *Cancer Chemother Pharmacol* 50:465-472, 2002.
Thomenius et al., "Using BH3 Profiling As a Predictive Indicator for Myeloma Patient Response to Bortezomib," *Blood* 118:3952, 2011. (6 pages).

(56) References Cited

OTHER PUBLICATIONS

Thornton et al., "High dose methyl prednisolone can induce remissions in CLL patients with p53 abnormalities," *Ann Hematol* 82:759-765, 2003.
Thornton et al., "Characterisation of TP53 abnormalities in chronic lymphocytic leukaemia," *The Hematology Journal* 5:47-54, 2004.
Tolero Pharmaceuticals, "Jefferies 2016 Heathcare Conference," 2016, 31 pages.
Toogood et al., "Discovery of a Potent and Selective Inhibitor of Cyclin-Dependent Kinase 4/6," *J. Med. Chem.* 48:2388-2406, 2005.
Touzeau et al., "BH3-profiling identifies heterogeneous dependency of Bcl-2 family members in Multiple Myeloma and predicts sensitivity to BH3 mimetics," *Leukemia* 30(3):761-764, 2016. (8 pages).
Traunecker et al., "Bispecific single chain molecular (Janusins) target cytotoxic lymphocytes on HIV infected cells," *The EMBO Journal* 10(12):3655-3659, 1991.
Tsao et al., "Concomitant inhibition of DNA methyltransferase and BCL-2 protein function synergistically induce mitochondrial apoptosis in acute myelogenous leukemia cells," *Ann Hematol* 91(12):1861-1870, 2012.
Tutt et al., "Trispecific F(ab')$_3$ Derivatives That Use Cooperative Signaling Via the TCR/CD3 Complex and CD2 to Activate and Redirect Resting Cytotoxic T Cells," *The Journal of Immunology* 147(1):60-69, 1991.
Valencia et al., "A new reliable fluorescence in situ hybridization method for identifying multiple specific cytogenetic abnormalities in acute myeloid leukemia," *Leukemia & Lymphoma* 51(4):680-685, 2010.
Vaquero et al., "Extracellular Matrix Proteins Protect Pancreatic Cancer Cells From Death Via Mitochondrial and Nonmitochondrial Pathways," *Gastroenterology* 125:1188-1202, 2003.
Vaux et al., "Bcl-2 gene promotes haemopoietic cell survival and cooperates with c-myc to immortalize pre-B cells," *Nature* 335:440-442, 1988.
Venkat, "Flavopiridol: A Drug that May Save Lives," 2004, retrieved from https://web.archive.org/web/20060615112217/http://clltopics.org/Chemo/flavopiridol.htm, 7 pages.
Venugopal et al., "A Phase I Study of Quisinostat (JNJ-26481585), an Oral Hydroxamate Histone Deacetylase Inhibitor with Evidence of Target Modulation and Antitumor Activity, in Patients with Advanced Solid Tumors," *Clin Cancer Res* 19(15):4262-4272, 2013.
Verhoeyen et al., "Reshaping Human Antibodies: Grafting an Antilysozyme Activity," *Science* 239:1534-1536, 1988.
Ververis et al., "Histone deacetylase inhibitors (HDACIs): multitargeted anticancer agents," *Biologics: Targets and Therapy* 7:47-60, 2013.
Vitetta et al., "Redesigning Nature's Poisons to Create Anti-Tumor Reagents," *Science* 238:1098-1104, 1987.
Vivès et al., "A Truncated HIV-1 Tat Protein Basic Domain Rapidly Translocates through the Plasma Membrane and Accumulates in the Cell Nucleus," *The Journal of Biological Chemistry* 272(25):16010-16017, 1997.
Vo, "Mitochondrial Priming Determines Chemotherapeutic Response in Acute Myeloid Leukemia," Dissertation, The Division of Medical Sciences, Harvard University, Cambridge, Massachusetts, Apr. 2012, 119 pages.
Vo et al., "Relative Mitochondrial Priming of Myeloblasts and Normal HSCs Determines Chemotherapeutic Success in AML," *Cell* 151:344-355, 2012.
Wang, "The expanding role of mitochondria in apoptosis," *Genes & Development* 15:2922-2933, 2001.
Wang et al., "BID: a novel BH3 domain-only death agonist," *Genes & Development* 10:2859-2869, 1996.
Wang et al., "Cell Permeable Bcl-2 Binding Peptides: A Chemical Approach to Apoptosis Induction in Tumor Cells," *Cancer Research* 60:1498-1502, 2000.
Wang et al., "Structure-based discovery of an organic compound that binds Bcl-2 protein and induces apoptosis of tumor cells," *PNAS* 97(13):7124-7129, 2000.

Wei et al., "tBID, a membrane-targeted death ligand, oligomerizes BAK to release cytochrome c," *Genes & Development* 14:2060-2071, 2000.
Wei et al., "Proapoptotic BAX and BAK: A Requisite Gateway to Mitochondrial Dysfunction and Death," *Science* 292:727-730, 2001.
Weinstein, "Addiction to Oncogenes—the Achilles Heal of Cancer," *Science* 297:63-64, 2002.
Weniger et al., "Treatment-Induced Oxidative Stress and Cellular Antioxidant Capacity Determine Response to Bortezomib in Mantle Cell Lymphoma," *Clinical Cancer Research* 17(15):5101-5112, 2011.
Werner et al., "Bcl-2 Family Member Bfl-1/A1 Sequesters Truncated Bid to Inhibit Its Collaboration with Pro-apoptotic Bak or Bax," *The Journal of Biological Chemistry* 277(25):22781-22788, 2002.
Westerhoff et al., "Magainins and the disruption of membrane-linked free-energy transduction," *Proc. Natl. Acad. Sci. USA* 86:6597-6601, 1989.
Wilkinson, "Ultimate Abs—Immunochemical techniques inspire development of new antibody purification methods," *The Scientist* 14(8):25-28, 2000. (6 pages).
Willis et al., "Proapoptotic Bak is sequestered by Mcl-1 and Bcl-$X_L$, but not Bcl-2, until displaced by BH3-only proteins," *Genes & Development* 19:1294-1305, 2005.
Willis et al., "Apoptosis Initiated When BH3 Ligands Engage Multiple Bcl-2 Homologs, Not Bax or Bak," *Science* 315:856-859, 2007.
Wolff et al., "Monoclonal Antibody Homodimers: Enhanced Antitumor Activity in Nude Mice," *Cancer Research* 53:2560-2565, 1993.
Wolter et al., "Movement of Bax from the Cytosol to Mitochondria during Apoptosis," *The Journal of Cell Biology* 139(5): 1281-1292, 1997.
Worland et al., "Alteration of the Phosphorylation State of $p34^{cdc2}$ Kinase by the Flavone L86-8275 in Breast Carcinoma Cells," *Biochemical Pharmacology* 46(10):1831-1840, 1993.
Woyach et al., "Targeted therapies in CLL: mechanisms of resistance and strategies for management," *Blood* 126:471-477, 2015.
Wyatt et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design," *J. Med. Chem.* 51:4986-4999, 2008.
Yamaguchi et al., "Bcl-XL Protects BimEL-induced Bax Conformational Change and Cytochrome c Release Independent of Interacting with Bax or BimEL," *The Journal of Biological Chemistry* 277(44):41604-41612, 2002.
Yang et al., "[11] Calculation of Protein Conformation from Circular Dichroism," *Methods Enzymol* 130:208-269, 1986.
Yang et al., "Bad, a Heterodimeric Partner for Bcl-$X_L$ and Bcl-2, Displaces Bax and Promotes Cell Death," *Cell* 80:285-291, 1995.
Yang et al., "A novel liposomal formulation of flavopiridol," *International Journal of Pharmaceutics* 365:170-174, 2009.
Yang et al., "Bone marrow stroma-mediated resistance to FLT3 inhibitors in FLT3-ITD AML is mediated by persistent activation of extracellular regulated kinase," *British Journal of Haematology* 164:61-72, 2014.
Yasuda et al., "BNIP3α: A Human Homolog of Mitochondrial Proapoptotic Protein BNIP3," *Cancer Research* 59:533-537, 1999.
Yeh et al., "Up-regulation of CDK9 kinase activity and Mcl-1 stability contributes to the acquired resistance to cyclin-dependent kinase inhibitors in leukemia," *Oncotarget* 6(5):2667-2679, 2014.
Yi et al., "Inhibition of Bid-induced Apoptosis by Bcl-2," *The Journal of Biological Chemistry* 278(19):16992-16999, 2003.
Yu et al., "Catalytic site remodelling of the DOT1L methyltransferase by selective inhibitors," *Nature Communications* 3:1288, 2012. (12 pages).
Zeng et al., "Targeting the leukemia microenvironment by CXCR4 inhibition overcomes resistance to kinase inhibitors and chemotherapy in AML," *Blood* 113:6215-6224, 2009.
Zha et al., "Serine Phosphorylation of Death Agonist BAD in Response to Survival Factor Results in Binding to 14-3-3 Not BCL-$X_L$," *Cell* 87:619-628, 1996.

(56) References Cited

OTHER PUBLICATIONS

Zha et al., "BH3 Domain of BAD Is Required for Heterodimerization with BCL-$X_L$ and Pro-apoptotic Activity," *The Journal of Biological Chemistry* 272(39):24101-24104, 1997.

Zha et al., "Posttranslational N-Myristoylation of BID as a Molecular Switch for Targeting Mitochondria and Apoptosis," *Science* 290:1761-1765, 2000.

Zhai et al., "Clinical pharmacology and pharmacogenetics of flavopiridol 1-h i.v. infusion in patients with refractory neoplasms," *Anti-Cancer Drugs* 14:125-135, 2003.

Zhao et al., "The Making of I-BET762, a BET Bromodomain Inhibitor Now in Clinical Development," *J. Med. Chem.* 56:7498-7500, 2013.

Zhou et al., "Novel mutant-selective EGFR kinase inhibitors against EGFR T790M," *Nature* 462(7276):1070-1074, 2009.

Zong et al., "BH3-only proteins that bind pro-survival Bcl-2 family members fail to induce apoptosis in the absence of Bax and Bak," *Genes & Development* 15:1481-1486, 2001.

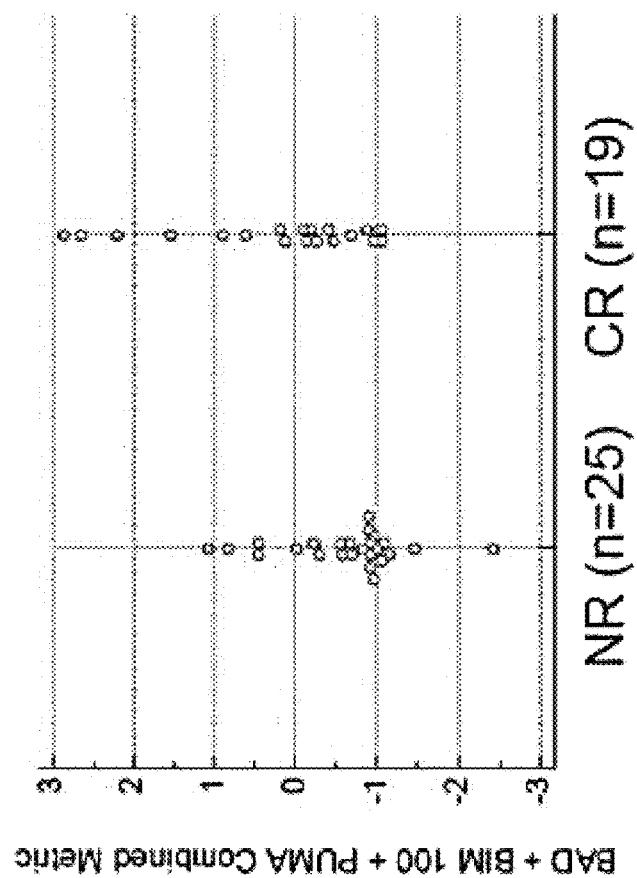
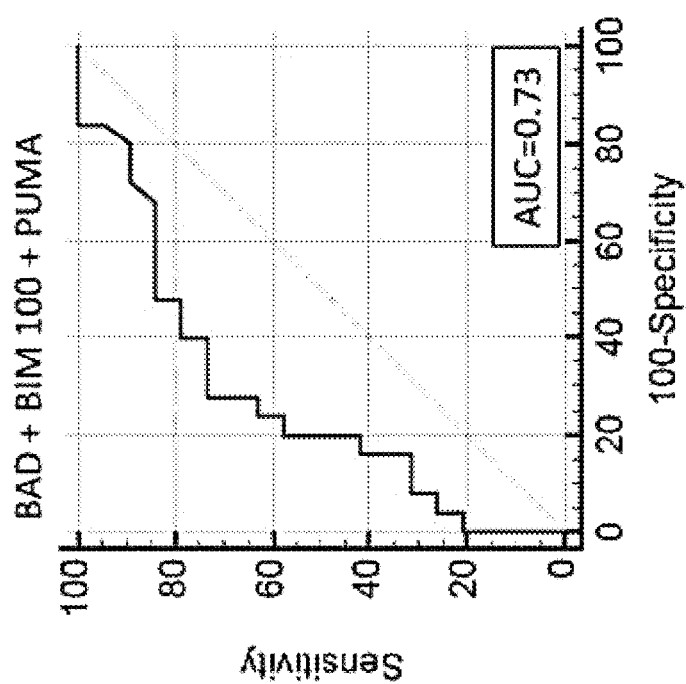
FIG. 2B
FIG. 2A

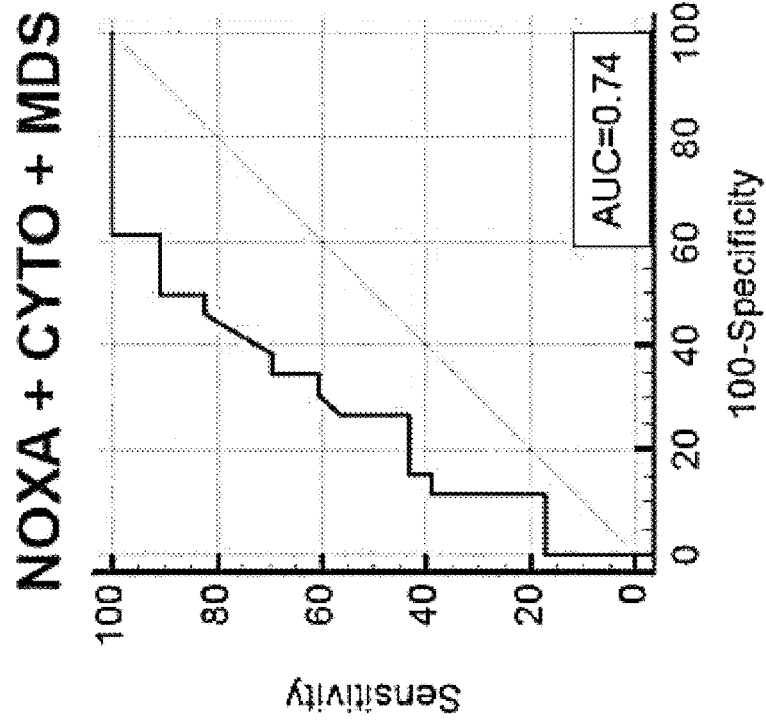
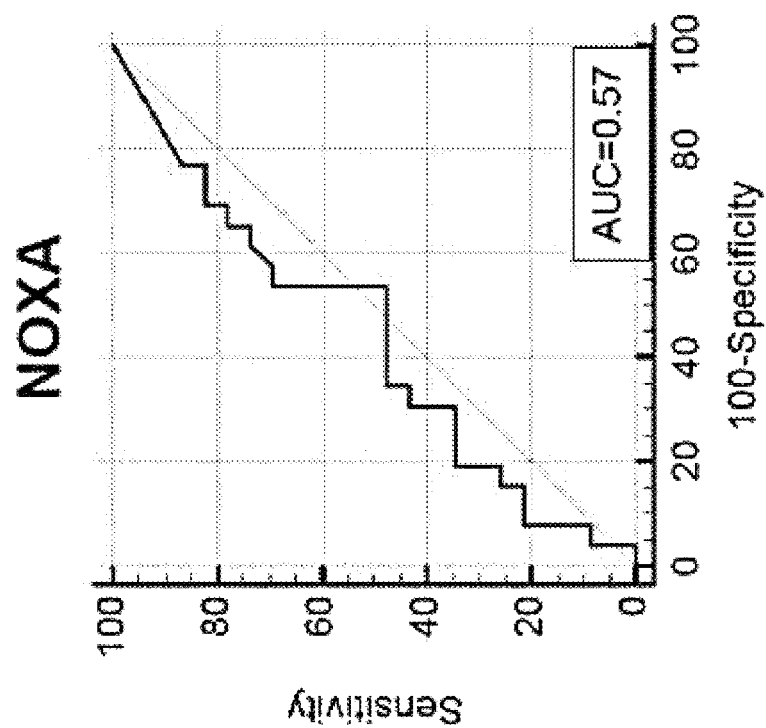
FIG. 4A
FIG. 4B

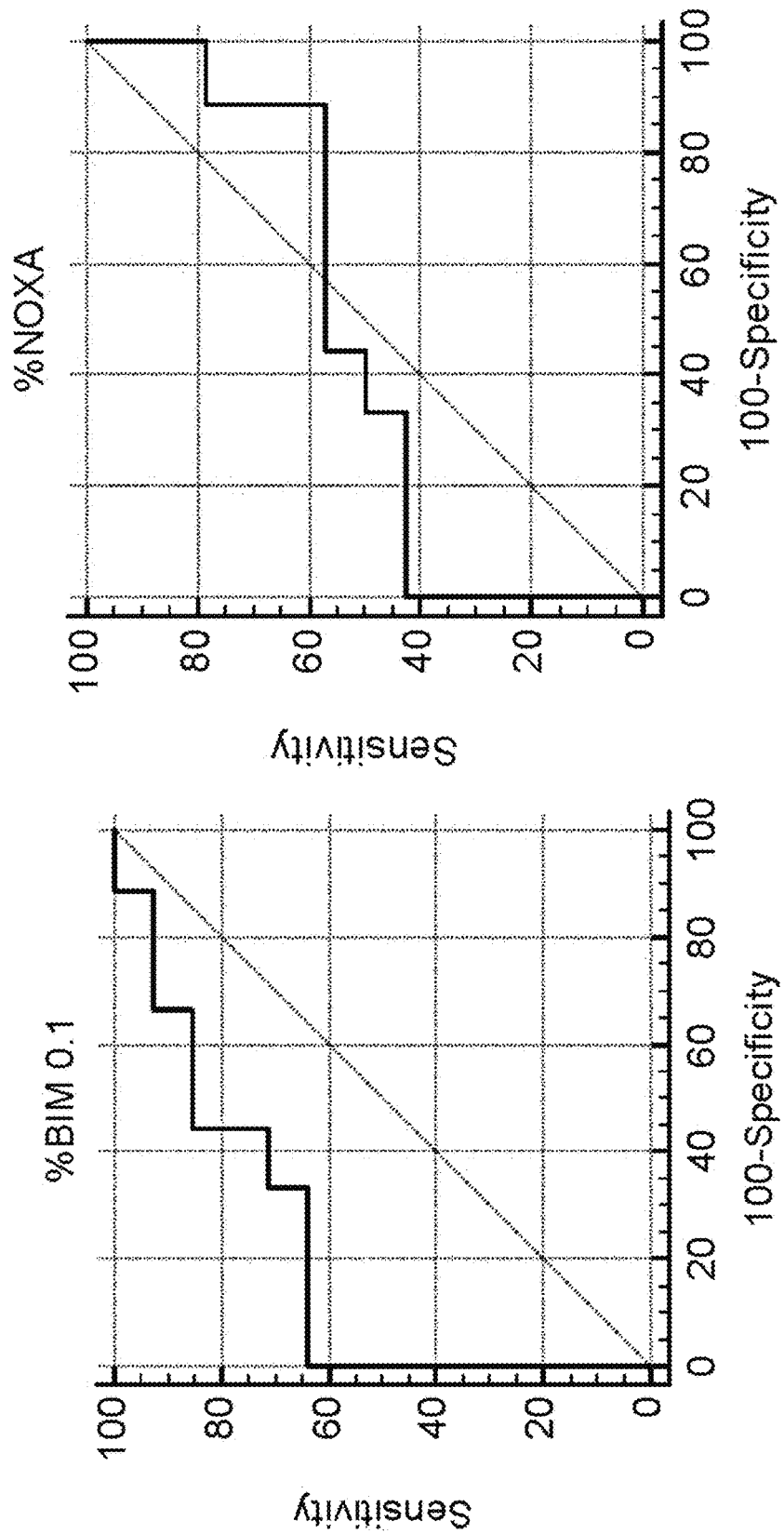

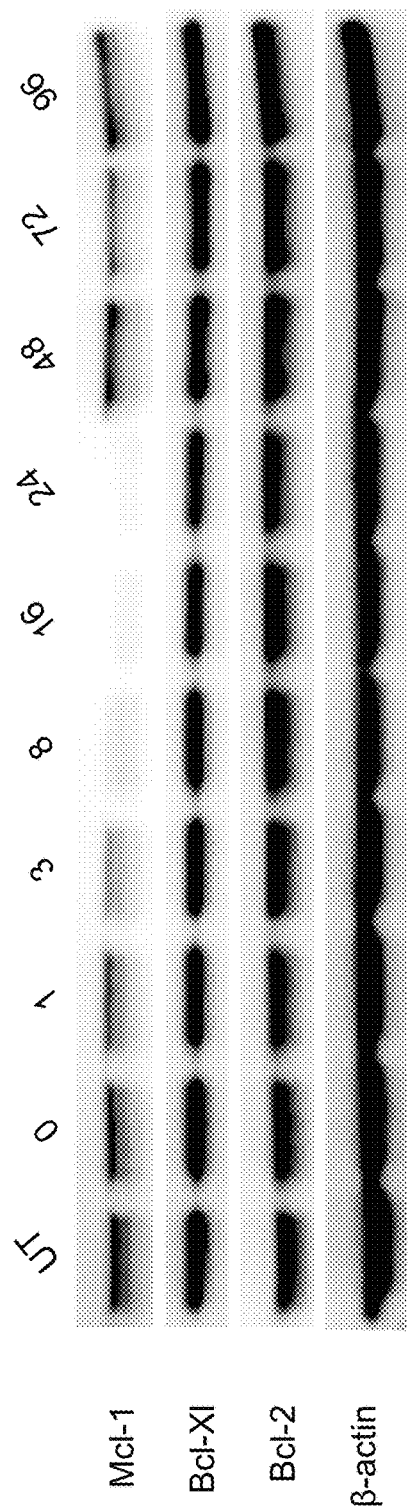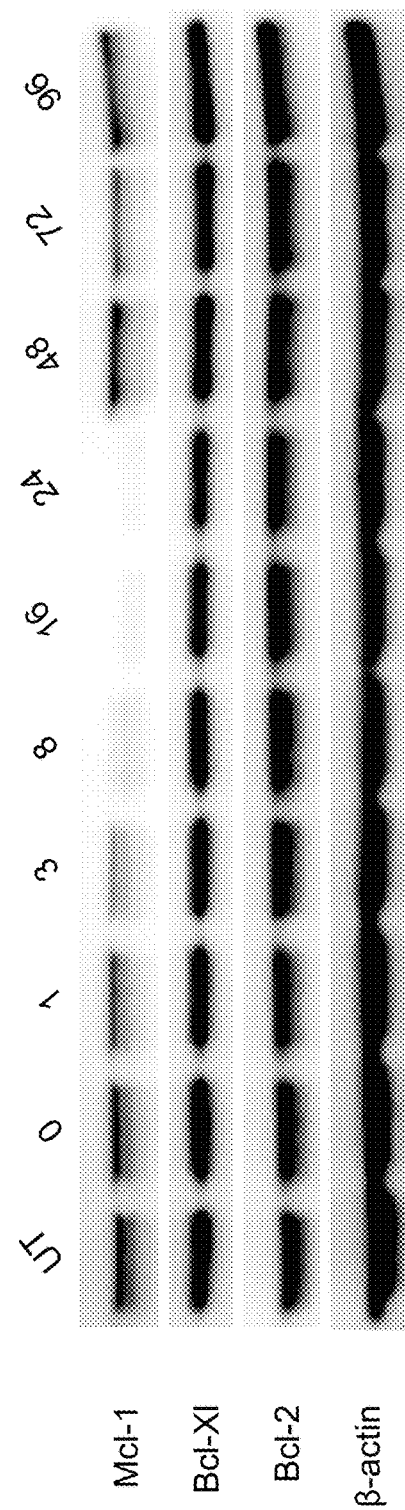
FIG. 13A
FIG. 13B

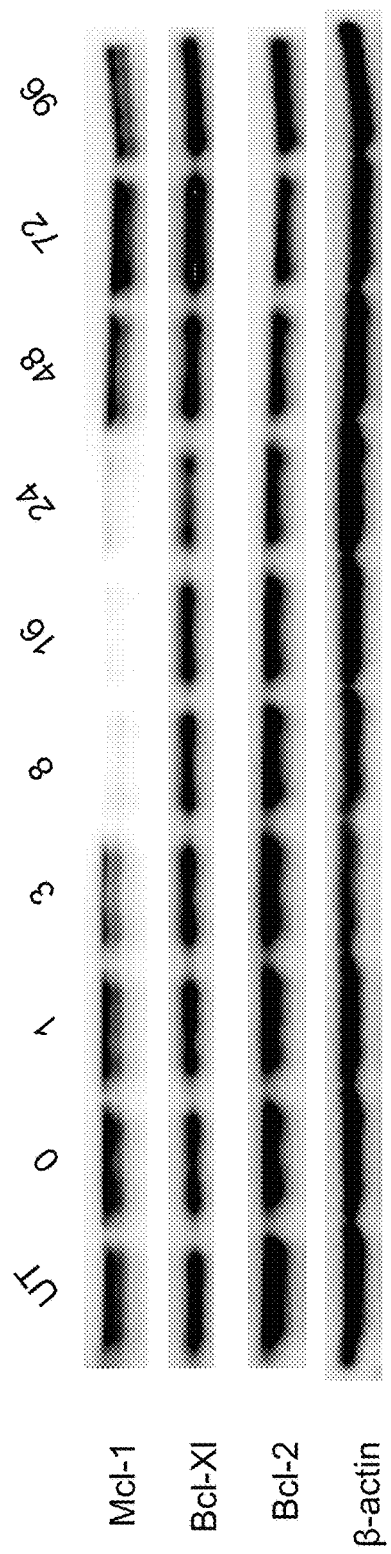
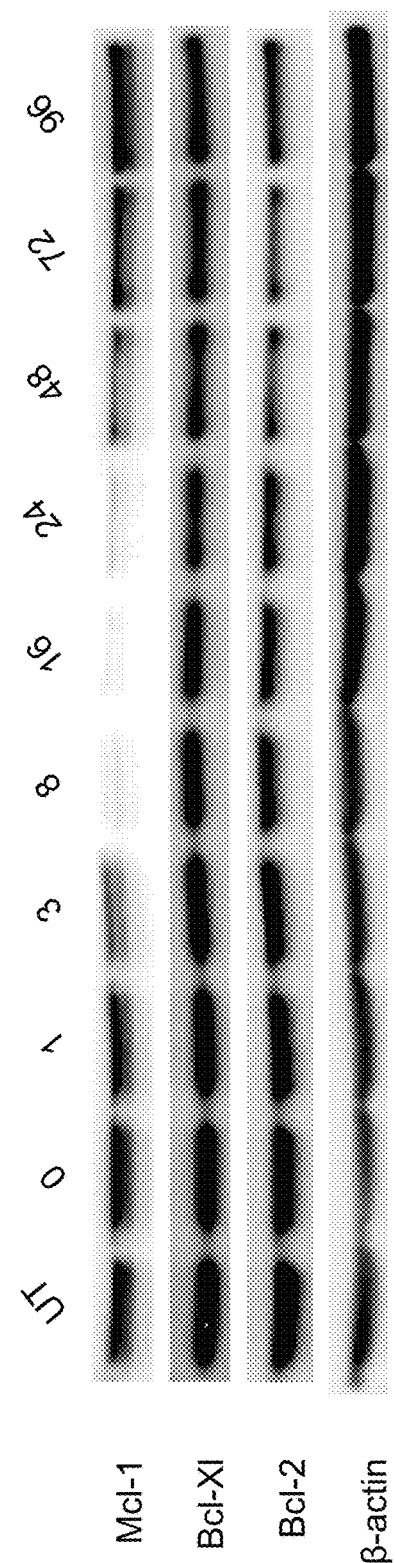
FIG. 15A
FIG. 15B

US 10,357,488 B2

PREDICTING RESPONSE TO ALVOCIDIB BY MITOCHONDRIAL PROFILING

This application is a continuation of prior application Ser. No. 15/874,755, which is a continuation of prior application Ser. No. 15/134,051, now U.S. Pat. No. 9,901,574.

JOINT RESEARCH AGREEMENT

The subject matter claimed herein was made as a result of activities undertaken within the scope of a joint research agreement. The parties to the joint research agreement are: (1) Tolero Pharmaceuticals, Inc.; and (2) Eutropics Pharmaceuticals, Inc.

FIELD OF THE INVENTION

The present disclosure is generally directed to methods for treating cancer by administration of an alvocidib-containing regimen to a patient having a high likelihood of response to the alvocidib-containing regimen. In some embodiments, the methods include predicting a patient's response to an alvocidib-containing treatment regimen.

BACKGROUND

The use of predictive and prognostic biomarkers paired with targeted cancer therapies may hold the key to reducing drug development time, improving drug efficacy, and guiding clinical decision making. While there are advances in cancer treatment, chemotherapy remains largely inefficient and ineffective. One reason for the generally poor performance of chemotherapy is that the selected treatment is often not closely matched to the individual patient's disease. A personalized medicine approach that couples precise diagnostics with therapeutics might alleviate this problem.

To date there are only a handful of biomarkers that have added value to clinical oncology practice. In part this is because perceived markers often are correlative but not causal to drug mechanism. Even when the "biomarker" biology does line up with the pharmacology of the companion therapy there is still significant challenge to predicting how a drug will work in a patient. Beyond this, the path to clinical development requires the participation of physician-scientists who see the value of the test and believe it can bring benefit to their patients.

The anti-apoptotic Bcl-2 family proteins are pivotal causal factors to cancer cell response to chemotherapy. Measurements of the functionality of these proteins in modulating mitochondrial apoptosis has proven to provide predictive biomarkers for cancer patient response to treatment. Many chemotherapies rely on apoptosis to be effective and in some cases modulation of apoptosis by a specific anti-apoptotic proteins correlates with responsiveness to particular therapy. The measurement of a particular protein then provides the biomarker for drug response. Accordingly, biomarkers that determine the expected response to a therapeutic agent continue to be sought after.

SUMMARY OF THE INVENTION

Accordingly, in one embodiment the present disclosure provides a method for treatment of cancer in a patient in need thereof, the method comprising:
  a) requesting BH3 profiling data for a cancer cell specimen obtained from the bone marrow of the patient; and
  b) administering a treatment regimen comprising alvocidib to the patient if NOXA priming in the cancer cell specimen is at least 15%.

In another embodiment, the disclosure is directed to a method for treatment of cancer in a patient in need thereof, the method comprising:
  a) requesting MCL-1 expression data for a cancer cell specimen obtained from the bone marrow of the patient; and
  b) administering a treatment regimen comprising alvocidib to the patient if MCL-1 expression in the cancer cell specimen is at least 1.1× the MCL-1 expression in a normal cell.

In still other embodiments, the disclosure is directed to a method for determining a patient's likelihood of response to a treatment regimen comprising alvocidib, the method comprising:
  contacting a permeabilized cancer cell specimen from the bone marrow of the patient with one or more BH3 domain peptides;
  determining NOXA priming in the specimen; and
  categorizing the patient as a likely responder to the treatment regimen if NOXA priming in the specimen is at least 15%.

In other related embodiments, the disclosure provides a method for determining a patient's likelihood of response to a treatment regimen comprising alvocidib, the method comprising:
  determining MCL-1 expression in a cancer cell specimen from the bone marrow of the patient; and
  categorizing the patient as a likely responder to the treatment regimen if MCL-1 expression in the specimen is at least 1.1×MCL-1 expression in normal cells.

In another aspect, the invention provides a method for selecting a cancer treatment for a patient, comprising determining a response to agents that perturb the MCL1 and BFL1 proteins in their function to sequester pro-apoptotic proteins using BH3 profiling of patients cancer cells and determining one or more clinical factors of the patient, and classifying the patient for likelihood of clinical response to one or more cancer treatments that perturb the function of MCL1.

In some embodiments, and as shown herein, patient cancer specimen are comprised of cancer cells purified from bone marrow aspirates. Cancer cells are exposed to agents that selectively perturb MCL1, or MCL1 and BFL1 binding to pro-apoptotic proteins Bim, Bid, Bax or Bak as determined using peptides comprising the BH3 only protein NOXA or BH3 mimetics that are selective for MCL1 or MCL1 and BFL1.

In some embodiments, and as shown herein, BH3 assay readouts from patient cancer specimens comprised of cancer cells purified from bone marrow aspirates and BH3 profiling readouts from peripheral blood are compared. The different readouts predict response to distinct treatment options. Further, BH3 profiling conducted on AML cells taken from patient bone marrow has been shown to predict FLAM treatment whereas BH3 profiling on AML cells from Peripheral blood does not, but does predict 7+3 treatment.

In some embodiments, and as shown herein, various clinical factors, even those unrelated or not known to be related to apoptosis, may be used to increase the predictive power of BH3 profiling, transforming the test to a predictive, not merely prognostic, test.

In some embodiments, the methods described herein provide a diagnostic test that is predictive of a leukemia patient response to a CDK-9 inhibiting compound. In some aspects, the CDK-9 inhibitor is flavopiridol (alvocidib). In additional aspects, the CDK-9 inhibitor may be co-administered with one or more additional compounds as part of a therapeutic regimen. For example, a regimen may be alvocidib in combination with ara-C and mitoxantrone (FLAM). Additional variables may be considered to increase the sensitivity of the assay variables. For example, patient cytogenetic profile or status and/or age may be factored into a predictive algorithm. In some embodiments, the diagnostic test comprises measuring function of MCL1, including measuring change in mitochondrial membrane potential in response to the BH3 peptide Noxa, or the MCL1/Bfl-1 selective BH3 mimetic compounds EU5346 (compound 9 in D. Richard et al. Molecular Cancer Therapeutics, 2013).

In another aspect, the invention provides a method for determining a cancer treatment for a patient, comprising contacting permeabilized cancer cells of the patient with one or more BH3 domain peptides to determine the extent of priming; determining the presence or absence of one or more clinical factors of the patient's cancer cells by immunohistochemistry and/or fluorescent in situ hybridization (FISH); and classifying the patient for likelihood of clinical response to one or more cancer treatments.

In another aspect, the invention provides a method for determining an AML patient response to alvocidib or FLAM treatment comprising: determining a BH3 profile for the patient's AML cancer cell specimen collected from bone marrow; determining one or more clinical factors of the patient, and wherein the one or more clinical factors are selected from age profile and/or cytogenetic status; and classifying the patient for likelihood of clinical response to one or more cancer treatments.

In another aspect, the invention provides a method for determining an AML patient response to alvocidib or FLAM treatment, or cytarabine based treatment alone comprising: determining a BH3 profile for the patient's AML cancer cell specimen collected from bone marrow; determining one or more clinical factors of the patient, and wherein the one or more clinical factors are selected from age profile and/or cytogenetic status; and classifying the patient for likelihood of clinical response to one or more cancer treatments. This readout is then compared to the BH3 profile readout from peripheral blood specimens. Specifically the BH3 profile readout of the Bim BH3 peptide at 0.1 PM and demonstrated to predictive for ara-C based treatment without alvocidib.

In another aspect, the invention provides a method for determining an AML patient response to an (interleukin-6) IL-6 antagonizing therapeutic, or and MCL1 selective BH3 mimetic comprising: determining a BH3 profile for the patient's AML cancer cell specimen collected from bone marrow; determining one or more clinical factors of the patient, and wherein the one or more clinical factors are selected from age profile and/or cytogenetic status; and classifying the patient for likelihood of clinical response to one or more cancer treatments. This readout is then compared to the BH3 profile readout from peripheral blood specimens.

The details of embodiments of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Further, the in vivo context of the cancer cell affects the extent to which the MCL1 protein is involved in the onset and maintenance of the cancer, and the efficacy of MCL1 targeted therapies. Specifically, myeloid leukemia and myeloma cells that are in the stroma of the bone marrow are more dependent on MCL1 for survival than those that are circulating in the peripheral blood. Further, it has been established that BIM BH3 peptide from the peripheral blood samples correlates to AML patient response to ara-c with anthracyclin, 7+3. Neither this readout however, nor any BH3 profiling readout from the leukemia cells in the peripheral blood predicts AML patient response to FLAM or to other MCL1 inhibiting therapies.

BH3 profiling on its own is known to provide a general sense of chemosensitivity or chemoresponsiveness to therapies. Here, however, recognizing the specific correlate for mechanisms that are focused on the MCL1 protein provides a uniquely sensitive method for predicting patient response to MCL1 affecting treatments. This however, is only true for certain MCL1 targeting therapies when the cancer cells are isolated from the stroma of the bone marrow.

BRIEF DESCRIPTION OF THE FIGURES

FIGS. 2A-F show BH3 Peptide Association by receiver operator channel (ROC) curve analyses with Response in all FLAM-treated patient specimens. Panels A, C, and E show the receiver operator channel (ROC) curve analyses of BAD, BIM 100, and PUMA in combination with the cytogenetic risk factor and MDS history clinical variables. Panels B, D, and F show corresponding dot plots illustrating each patient data point from the combined metrics in the patients who reached CR compared with those who did not.

FIGS. 4A-D show Noxa BH3 Peptide Association by receiver operator channel (ROC) curve analyses with Response in bone marrow-derived FLAM treated patient specimens. Panels A and B show the receive operator channel (ROC) curve analyses of NOXA peptide priming in combination with the cytogenetic risk factor and MDS history clinical variables in all samples. Panels C and D show the same in samples drawn from bone marrow, but not in samples from the peripheral blood. Addition of cytogenetic risk factor and MDS history improves the predictive power of the test, with an AUC value of 0.92 in BM NOXA priming with cytogenetic risk factor and MDS history.

FIGS. 5A-B show examples of BIM 0.1 and NOXA profiling.

FIGS. 13A-B show alvocidib suppresses expression of oncogenic proteins in a time dependent manner with a wash step (FIG. 13A), and without a wash step (FIG. 13B), for Panc-1 cells.

FIGS. 15A-B show alvocidib suppresses expression of oncogenic proteins in a time dependent manner with a wash step (FIG. 15A), and without a wash step (FIG. 15B), for Yugen8 cells.

Figure 1B:
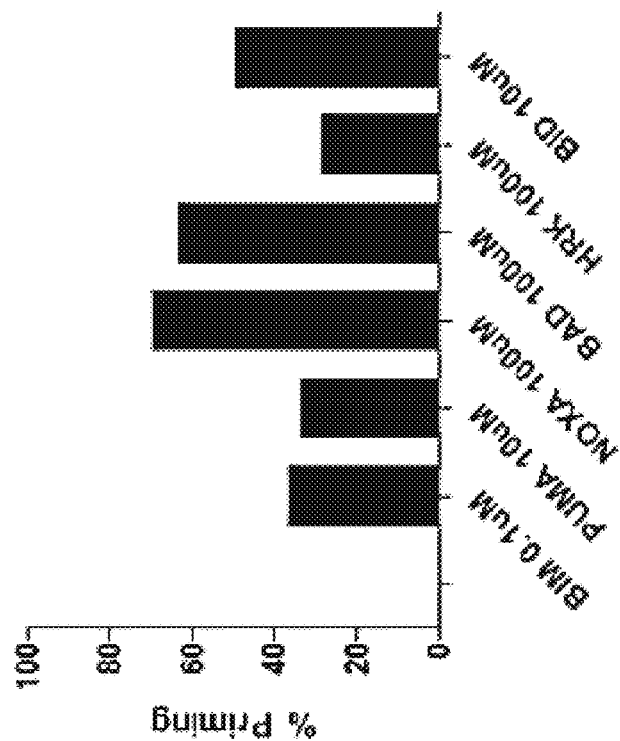
FIGS. 1A-E show representative BH3 profiling data from bone marrow samples obtained from patients that were treated with the FLAM regimen. The figure shows differences in patterns of high versus low primed blast cells from AML patients. The cutoff identified was ideal by ROC analysis for NOXA priming in the bone marrow was around 10.7%. Panels A-C show examples of each cytogenetic risk category (Fav-favorable, adv-adverse, and int-intermediate) showing higher NOXA priming and underwent CR. Panels D-E show an intermediate risk and adverse risk with low NOXA priming that had treatment failures.
Figure 1A:
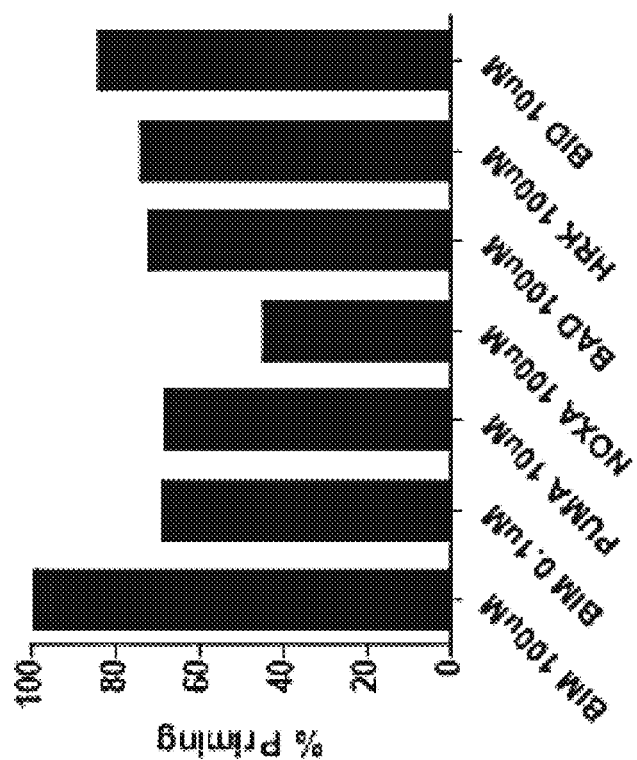
Figure 1D:
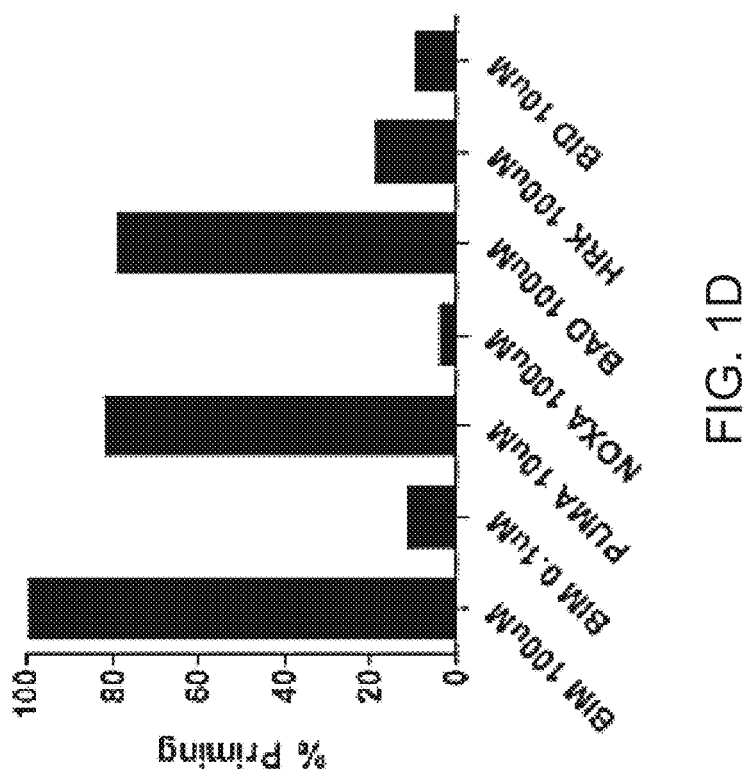
Figure 1C:
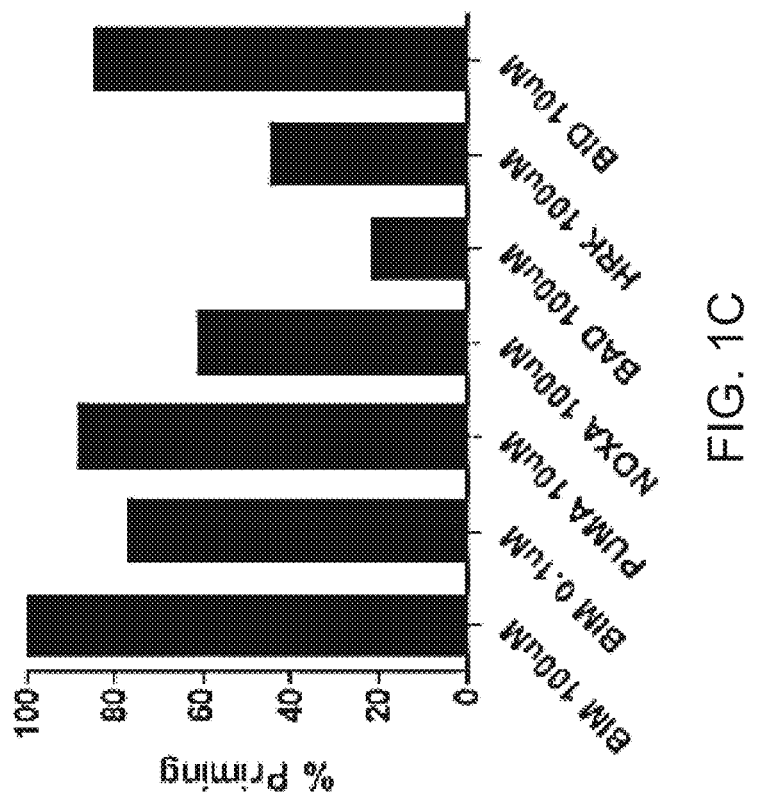
Figure 1E:
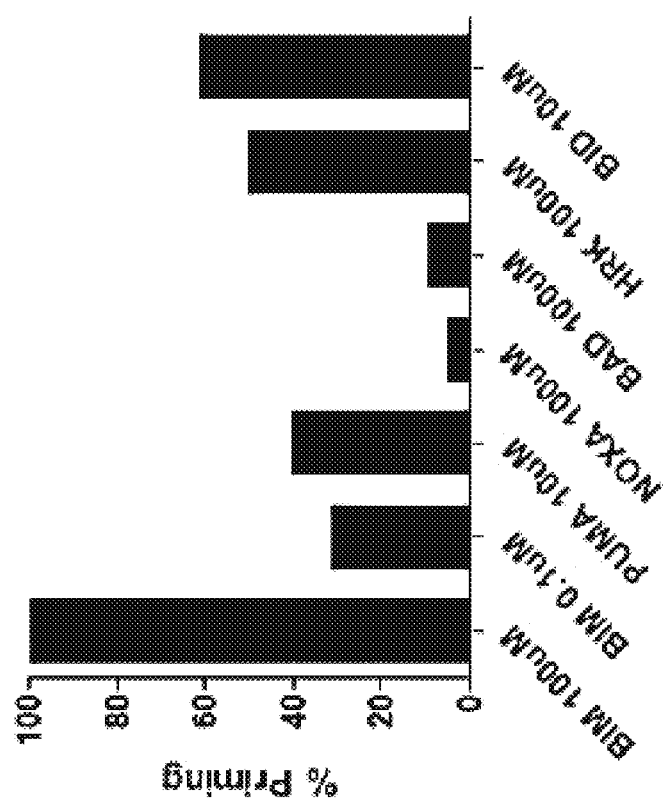

Table 1 shows a FLAM patient study. The overall patient summary is shown in the table, with the numbers of patients positive for each metric above over the total number with available data for each value.

Table 2 shows FLAM treated patient summary analysis. The table lists all samples obtained. Patients were enrolled on three different protocols (J0669, J0856, and J01101) and were mostly newly diagnosed AML patients. Samples were obtained from either the peripheral blood or bone marrow aspirates. Age was calculated at the time of diagnosis. Cytogenetic risk factor was determined using CALGB guidelines. Cytogenetics, FLT-3, and NPM1 mutations status, MDS history, chemotherapy history, percent bone marrow blast, white blood cell (WBC) counts, treatments, and response were all obtained. Samples that are shaded gray were not successfully assay for BH3 priming and are excluded from all subsequent analyses (MRD—minimal residual disease, TF—treatment failure, PR—partial response, CR—complete remission).

Table 3 shows the Clinical Characteristics Associations with FLAM Response. Statistical analyses of clinical variables were performed relative to response. Each of the indicated metrics was tested for significance by the rank-sum Mann-Whitney test and by Logistic Regression analysis. The AUC (area under the curve) was obtained from ROC curve analysis.

Table 4 shows the BH3 Profiling Data from FLAM patient study. BH3 profiling was performed on all patient samples listed in Table 2. Rows that are shaded grey are samples that failed the acceptance criteria of BH3 profiling during processing. Any cell containing a dash (-) did not have sufficient cells to perform the respective BH3 peptide assay for the indicated sample. Signal to noise is a measure of the DMSO JC-1 red mean fluorescence intensity (MFI) over the CCCP JC-1 read MFI. The cell counts and percent viability were determined by manual cell counting with trypan blue exclusion. Percent blasts are the percentages of CD45-dim, CD3/CD20 negative, and SSC-low of the permeabilized viable cells. All BH3 profiling was performed on those gated blast cells.

Table 5 shows Associations of individual BH3 peptide profiles with CR. Statistical analyses of BH peptides were performed relative to response, with CR samples compared with all partial responses, minimal residual diseases, and treatment failures (NR—non-responder). Each of the indicate metrics was tested for significance by the rank-sum Mann-Whitney test and by Logistic Regression analysis. The AUC (area under the curve) was obtained from ROC curve analysis.

Table 6 shows Multivariate Analysis of BH3 Peptide Profiling with Other Clinical Variables in FLAM study. Statistical analyses of BH3 peptides were performed relative to response, with CR samples compared with NR samples. Combinations of variables were tested using logistic regression to determine coefficients and constants under a logistic regression model, and then these coefficients and constants were tested by the rank-sum Mann-Whitney test and ROC curve analysis.

Table 7 shows Associations of Individual BH3 Peptide Profiles with CR in Bone Marrow Samples. Statistical analyses of BH3 peptides were performed in only those samples that were obtained from bone marrow as done in Table 5. Each of the indicated metrics was tested for significance by the rank-sum Mann-Whitney test and by Logistic Regression analysis. The AUC (area under the curve) was obtained from ROC curve analysis. This analysis reveals that NOXA priming is significantly higher in the patients that responded to treatment compared with the non-responders.

Table 8 shows Statistical analyses of BH3 peptides were performed in only those samples that were obtained from bone marrow. Statistical analyses of BH 3 peptides were performed in only those samples that were obtained from bone marrow as done in Table 6. Combinations of variables were tested using logistic regression to determine coefficients and constants under a logistic regression model, and then these coefficients and constants were tested by the rank-sum Mann-Whitney test and ROC curve analysis. This analysis shows that the combination of BAD, BIM 100, and PUMA is also associated with response in bone marrow samples alone. Bothe the NOXA and the three peptide readouts are additive to the cytogenetic risk category and MDS history and result in higher significance and AUC values.

DETAILED DESCRIPTION OF THE INVENTION

The present disclosure is based, in part, on the discovery that the medical utility of the BH3 profiling assay can be realized for predicting response to CDK inhibitors, such as a CDK-9 inhibitor (e.g. alvocidib) alone or in a co-treatment regime by measuring the response in cancer cells that have been exclusively collected from patient bone marrow aspirate. The sensitivity and/or specificity of BH3 profiling measurements are significantly improved over blood collected from peripheral blood or combinations of peripheral blood samples and bone marrow samples. It was seen that a dramatic improvement in correlation of the Noxa generated signal occurred a 0.445 p-value improved to 0.0007 when the samples were exclusively taken from bone marrow compared to a peripheral blood sample from the same patient. (Tables 6 and 7). The sensitivity of the assay improved from 0.805 (AUC) to 0.91 (AUC) when clinical variables, cytogenetics and age, were factored into the analysis.

The diagnostic approaches described herein provide a new method for predicting response to MCL1 perturbing therapies.

In one aspect, the invention provides a method for determining a cancer treatment for a patient, comprising determining the extent of MCL1 dependence in a patient's tumor or cancer cell specimen exclusively collected from bone marrow; determining one or more clinical factors of the patient, and classifying the patient for likelihood of clinical response to one or more cancer treatments; wherein the one or more clinical factors are selected to increase specificity and/or sensitivity of the MCL1 specific BH3 profiling readout for association with clinical response.

In another aspect, the invention provides a method for determining a cancer treatment for a patient, comprising contacting permeabilized cancer cells of the patient with the Noxa BH3 domain peptides to determine the extent of priming; determining the presence or absence of one or more clinical factors of the patient's cancer cells by immunohistochemistry and/or fluorescent in situ hybridization (FISH); and classifying the patient for likelihood of clinical response to one or more cancer treatments.

In another aspect, the invention provides a method for determining an AML patient response to cytarabine and/or FLAM comprising: determining a BH3 profile for the patient's AML cancer cell specimen taken wither from bone marrow or peripheral blood; comparing readouts from those two cancer cell sources and using that information to guide either FLAM or cytarabine based treatment.

In various embodiments, the clinical factor is one or more of age, cytogenetic status, performance, histological subclass, gender, and disease stage. In another embodiment, the method further comprises a measurement of an additional biomarker selected from mutational status, single nucleotide polymorphisms, steady state protein levels, and dynamic protein levels, which can add further specificity and/or sensitivity to the test. In another embodiment, the method further comprises predicting a clinical response in the patient. In another embodiment, the clinical response is at least about 1, about 2, about 3, or about 5 year progression/event-free survival.

In certain embodiments, the priming is defined by the following equation: in which the AUC comprises either area under the curve or signal intensity; the DMSO comprises the baseline negative control; and the CCCP (Carbonyl cyanide m-chlorophenyl hydrazone) comprises an effector of protein synthesis by serving as uncoupling agent of the proton gradient established during the normal activity of electron carriers in the electron transport chain in the mitochondria comprises the baseline positive control. In some embodiments, the area under the curve is established by homogenous time-resolved fluorescence (HTRF). In some embodiments, the time occurs over a window from between about 0 to about 300 min to about 0 to about 30 min. In some embodiments, the area under the curve is established by fluorescence activated cell sorting (FACS). In some embodiments, the signal intensity is a single time point measurement that occurs between about 5 min and about 300 min.

$$\% \text{ Priming} = \left[100 * \left(\frac{DMSO\ AUC - \text{Peptide}_1\ AUC}{DMSO\ AUC - CCCP_{avg}AUC}\right)\right]\text{Peptide}_1 +$$
$$\left[100 * \left(\frac{DMSO\ AUC - \text{Peptide}_2\ AUC}{DMSO\ AUC - CCCP_{avg}AUC}\right)\right]\text{Peptide}_2 + \cdots / (n\text{ peptides})$$

Exemplary Clinical Decisions

In some embodiments, the methods described herein are useful in the evaluation of a patient, for example, for evaluating diagnosis, prognosis, and response to treatment. In various aspects, the present invention comprises evaluating a tumor or hematological cancer. In various embodiments, the evaluation may be selected from diagnosis, prognosis, and response to treatment.

Diagnosis refers to the process of attempting to determine or identify a possible disease or disorder, such as, for example, cancer. Prognosis refers to predicting a likely outcome of a disease or disorder, such as, for example, cancer. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment. Responses to treatment can be, by way of non-limiting example, pathological complete response, survival, and progression free survival, time to progression, probability of recurrence.

In various embodiments, the present methods direct a clinical decision regarding whether a patient is to receive a specific treatment. In one embodiment, the present methods are predictive of a positive response to neoadjuvant and/or adjuvant chemotherapy or a non-responsiveness to neoadjuvant and/or adjuvant chemotherapy. In one embodiment, the present methods are predictive of a positive response to a pro-apoptotic agent or an agent that operates via apoptosis and/or an agent that does not operate via apoptosis or a non-responsiveness to apoptotic effector agent and/or an agent that does not operate via apoptosis. In various embodiments, the present invention directs the treatment of a cancer patient, including, for example, what type of treatment should be administered or withheld.

In one embodiment, the present methods direct a clinical decision regarding whether a patient is to receive adjuvant therapy after primary, main or initial treatment, including, without limitation, a single sole adjuvant therapy. Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease.

In some embodiments, the present methods direct a patient's treatment to include adjuvant therapy. For example, a patient that is scored to be responsive to a specific treatment may receive such treatment as adjuvant therapy. Further, the present methods may direct the identity of an adjuvant therapy, by way of non-limiting example, as a treatment that induces and/or operates in a pro-apoptotic manner or one that does not. In one embodiment, the present methods may indicate that a patient will not be or will be less responsive to a specific treatment and therefore such a patient may not receive such treatment as adjuvant therapy. Accordingly, in some embodiments, the present methods provide for providing or withholding adjuvant therapy according to a patient's likely response. In this way, a patient's quality of life, and the cost of care, may be improved.

In some embodiments, the present methods direct a clinical decision regarding whether a patient is to receive a specific type of treatment. Accordingly, in some embodiments, the present methods are a guiding test for patient treatment.

In some embodiments, the present methods provide information about the likely response that a patient is to have to a particular treatment. In some embodiments, the present methods provide a high likelihood of response and may direct treatment, including aggressive treatment. In some embodiments, the present methods provide a low likelihood of response and may direct cessation of treatment, including aggressive treatment, and the use of palliative care, to avoid unnecessary toxicity from ineffective chemotherapies for a better quality of life.

In an exemplary embodiment, the present method will indicate a likelihood of response to a specific treatment. For example, in some embodiments, the present methods indicate a high or low likelihood of response to a pro-apoptotic agent and/or an agent that operates via apoptosis and/or an agent that operates via apoptosis driven by direct protein modulation. In various embodiments, exemplary pro-apoptotic agents and/or agents that operate via apoptosis and/or an agent that operates via apoptosis driven by direct protein modulation include ABT-263 (Navitoclax), and obatoclax, WEP, bortezomib, and carfilzomib. In some embodiments, the present methods indicate a high or low likelihood of response to an agent that does not operate via apoptosis and/or an agent that does not operate via apoptosis driven by direct protein modulation. In various embodiments, exemplary agents that do not operate via apoptosis include kinesin spindle protein inhibitors, cyclin-dependent kinase inhibitor, Arsenic Trioxide (TRISENOX), MEK inhibitors, pomolidomide, azacytidine, decitibine, vorinostat, entinostat, dinaciclib, gemtuzumab, BTK inhibitors, PI3 kinase delta inhibitors, lenolidimide, anthracyclines, cytarabine, melphalam, Akt inhibitors, mTOR inhibitors.

In an exemplary embodiment, the present method will indicate whether a patient is to receive a pro-apoptotic agent or an agent that operates via apoptosis for cancer treatment. In another exemplary embodiment, the present method will indicate whether a patient is to receive an agent that does not operate via apoptosis.

In a specific embodiment, the present methods are useful in predicting a cancer patient's response to any of the treatments (including agents) described herein. In an exemplary embodiment, the present invention predicts an AML patient's likelihood of response to cytarabine and azacytidine and comprises an evaluation of the BH3 profile, age profile and cytogenetic factors of the patient.

In various embodiments, a cancer treatment is administered or withheld based on the methods described herein. Exemplary treatments include surgical resection, radiation therapy (including the use of the compounds as described herein as, or in combination with, radiosensitizing agents), chemotherapy, pharmacodynamic therapy, targeted therapy, immunotherapy, and supportive therapy (e.g., painkillers, diuretics, antidiuretics, antivirals, antibiotics, nutritional supplements, anemia therapeutics, blood clotting therapeutics, bone therapeutics, and psychiatric and psychological therapeutics).

In various other embodiments, the invention is directed to a method for treatment of cancer in a patient in need thereof, the method comprising:
a) requesting BH3 profiling data for a cancer cell specimen obtained from the bone marrow of the patient; and
b) administering a treatment regimen comprising alvocidib to the patient if NOXA priming in the cancer cell specimen is at least 15%.

In some embodiments of the foregoing, the treatment regimen is administered to the patient only if NOXA priming in the cancer cell specimen is at least 20%, at least 25%, at least 30%, at least 35% or at least 40%.

In still more embodiments, MCL-1 expression in the cancer cell specimen is also used to determine a patient's suitability for treatment with an alvocidib-containing regiment, the method further comprising requesting MCL-1 expression data obtained from the cancer cell specimen, and administering the treatment regimen to the patient only if MCL-1 expression in the cancer cell specimen is at least 1.1× the MCL-1 expression in a normal cell. In further embodiments, the treatment regimen is administered to the patient only if MCL-1 expression in the cancer cell specimen is at least 1.5×, 2×, 3×, 4×, 5× or even 10× the MCL-1 expression in a normal cell.

In still other embodiments, the treatment regimen is administered to the patient only if the patient's cytogenetics are high risk.

In more embodiments of the foregoing, the treatment regimen is administered to the patient only if the patient has a prior history of myelodysplasic syndrome (MDS).

In still other embodiments of the foregoing, the BH3 profiling data is obtained from a method comprising permeabilizing the cancer cell specimen, determining a change in mitochondrial membrane potential upon contacting the permeabilized cell with one or more BH3 domain peptides; and correlating a loss of mitochondrial membrane potential with chemosensitivity of the cell to apoptosis-inducing chemotherapeutic agents.

In more exemplary embodiments, the BH3 domain peptide is BIM, BIM2A, BAD, BID, HRK, PUMA, NOXA, BMF, BIK or PUMA2A, or combinations thereof. For example, in some embodiments the BH3 domain peptide is used at a concentration ranging from 0.1 μM to 200 μM.

In still other embodiments, MCL-1 expression is used as the primary guide for determining a patient's suitability for treatment with an alvocidib-containing regimen. For example, in some embodiments the invention provides a method for treatment of cancer in a patient in need thereof, the method comprising:
a) requesting MCL-1 expression data for a cancer cell specimen obtained from the bone marrow of the patient; and
b) administering a treatment regimen comprising alvocidib to the patient if MCL-1 expression in the cancer cell specimen is at least 1.1× the MCL-1 expression in a normal cell. In some embodiments, the cancer cell is a tumor cell.

In other embodiments of the foregoing, the treatment regimen is administered to the patient only if MCL-1 expression in the cancer cell specimen is at least 1.5×, 2×, 3×, 4×, 5× or even 10× the MCL-1 expression in a normal cell.

In still more embodiments NOXA priming is considered along with MCL-1 expression, and the method further comprises requesting BH3 profiling data for the cancer cell specimen and administering the treatment regimen only if NOXA priming in the tumor or cancer cell specimen is at least 15%, at least 20%, at least 25%, at least 30%, at least 35% or at least 40%.

In still more embodiments, the treatment regimen is administered to the patient only if the patient's cytogenetics are high risk. In other embodiments, the treatment regimen is administered to the patient only if the patient has a prior history of myelodysplasic syndrome (MDS).

In any of the foregoing treatment methods, the cancer is a hematologic cancer. For example, in some embodiments the hematologic cancer is selected from acute myelogenous leukemia (AML), multiple myeloma, follicular lymphoma, acute lymphoblastic leukemia (ALL), chronic lymphocytic leukemia, and non-Hodgkin's lymphoma. In some specific embodiments, the hematological cancer is acute myelogenous leukemia (AML).

In some other embodiments of the foregoing, the hematologic cancer is myelodysplasic syndrome (MDS). In different embodiments of the foregoing, the hematologic cancer is chronic lymphocytic leukemia (CLL).

In other of any of the foregoing embodiments, the treatment regimen comprising alvocidib comprises alvocidib, cytarabine, and mitoxantrone (FLAM).

In still more embodiments of the foregoing, the cancer cell specimen is derived from the biopsy of a non-solid tumor. For example, in some embodiments the cancer cell specimen is derived from the biopsy of a patient with multiple myeloma, acute myelogenous leukemia, acute lymphocytic leukemia, chronic lymphogenous leukemia, mantle cell lymphoma, diffuse large B-cell lymphoma or non-Hodgkin's lymphoma.

In still more other embodiments, the cancer cell specimen is a multiple myeloma cell that is enriched by selection from a biopsy sample with an anti-CD138 antibody bound to a solid matrix or bead. For example, in some embodiments the cancer cell specimen is an acute myelogenous leukemia cell that is enriched by binding to a CD45-directed antibody. In other embodiments, the cancer cell specimen is a chronic lymphogenous leukemia or diffuse large B-cell lymphoma that is enriched by non-B cell depletion.

In still more embodiments, the invention is directed to a method for determining a patient's likelihood of response to a treatment regimen comprising alvocidib, the method comprising:

contacting a permeabilized cancer cell specimen from the bone marrow of the patient with one or more BH3 domain peptides;

determining NOXA priming in the specimen; and categorizing the patient as a likely responder to the treatment regimen if NOXA priming in the specimen is at least 15%.

A "likely responder" is a patient with greater than 50% chance of responding favorably (e.g., partial or complete remission) to treatment.

In still other embodiments, the invention provides a method for determining a patient's likelihood of response to a treatment regimen comprising alvocidib, the method comprising:

determining MCL-1 expression in a cancer cell specimen from the bone marrow of the patient; and categorizing the patient as a likely responder to the treatment regimen if MCL-1 expression in the specimen is at least 1.1×MCL-1 expression in normal cells.

In further embodiments of the foregoing, the method further comprises administering the treatment regimen to a patient categorized as a likely responder.

In still more embodiments, the invention is directed to a method of selecting between cancer therapy strategies in a pre-treatment AML patient, the method comprising (a) requesting results of a test to determine NOXA priming in a bone marrow (BM) sample of the patient;

(b) requesting results of a test to determine BIM 0.1 priming in a peripheral blood (PB) sample of the patient;

(c) comparing the NOXA priming to the BIM 0.1 priming; and (i) administering an alvocidib-containing regiment (e.g., FLAM) to the patient where BM NOXA>10.8% and BM/PB BIM 0.1<35%;

(ii) administering a 7+3 regimen to the patient where BM NOXA<10.8% and BM/PB BIM 0.1>15%;

(ii) administering a 7+3 regimen to the patient where BM NOXA<10.8% and BM/PB BIM 0.1>35%; or (iv) administering another therapy to the patient where BM NOXA<10.8% and BM/PB BIM 0.1<15%.

Exemplary Treatments

In exemplary embodiments, the invention selects a treatment agent. Examples of such agents include, but are not limited to, one or more of anti-cancer drugs, chemotherapy, surgery, adjuvant therapy, and neoadjuvant therapy. In one embodiment, the cancer treatment is one or more of a BH3 mimetic, epigenetic modifying agent, topoisomerase inhibitor, cyclin-dependent kinase inhibitor, and kinesin-spindle protein stabilizing agent. In another embodiment, the cancer treatment is a proteasome inhibitor; and/or a modulator of cell cycle regulation (by way of non-limiting example, a cyclin dependent kinase inhibitor); and/or a modulator of cellular epigenetic mechanistic (by way of non-limiting example, one or more of a histone deacetylase (HDAC) (e.g. one or more of vorinostat or entinostat), azacytidine, decitabine); and/or an anthracycline or anthracenedione (by way of non-limiting example, one or more of epirubicin, doxorubicin, mitoxantrone, daunorubicin, idarubicin); and/or a platinum-based therapeutic (by way of non-limiting example, one or more of carboplatin, cisplatin, and oxaliplatin); cytarabine or a cytarabine-based chemotherapy; a BH3 mimetic (by way of non-limiting example, one or more of BCL2, BCLXL, or MCL1); and an inhibitor of MCL1.

In various embodiments, the invention pertains to cancer treatments including, without limitation, those described in US Patent Publication No. US 2012-0225851 and International Patent Publication No. WO 2012/122370, the contents of which are hereby incorporated by reference in their entireties.

In various embodiments, the invention pertains to cancer treatments including, without limitation, one or more of alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-I, Raf, H-Ras, EGFR (e.g., erlotinib (Tarceva)) and VEGF-A that reduce cell proliferation, dacogen, velcade, and pharmaceutically acceptable salts, acids or derivatives of any of the above.

Exemplary Detection Methods

In various embodiments, the present methods comprise evaluating a presence, absence, or level of a protein and/or a nucleic acid. In various embodiments, the present methods comprise evaluating a presence, absence, or level of a protein and/or a nucleic acid which can enhance the specificity and/or sensitivity of BH3 profiling. In some embodiments, the evaluating is of a marker for patient response. In some embodiments, the present methods comprise measurement using one or more of immunohistochemical staining, western blotting, in cell western, immunofluorescent staining, ELISA, and fluorescent activating cell sorting (FACS), or any other method described herein or known in the art. The present methods may comprise contacting an antibody with a tumor specimen (e.g. biopsy or tissue or body fluid) to identify an epitope that is specific to the tissue or body fluid and that is indicative of a state of a cancer.

There are generally two strategies used for detection of epitopes on antigens in body fluids or tissues, direct methods and indirect methods. The direct method comprises a one-step staining, and may involve a labeled antibody (e.g. FITC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, NY, 1988), Harlow et al. (Using Antibodies, A Laboratory Manual, Cold Spring Harbor Laboratory, NY, 1999), Virella (Medical Immunology, 6th edition, Informa HealthCare, New York, 2007), and Diamandis et al. (Immunoassays, Academic Press, Inc., New York, 1996). Kits for conducting these assays are commercially available from, for example, Clontech Laboratories, LLC. (Mountain View, Calif.).

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the VL, VH, CL and CH1 domains; a F(ab)2 fragment, a bivalent fragment including two Fab fragments linked by a disulfide bridge at the hinge region; a Fd fragment consisting of the VH and CH1 domains; a Fv fragment consisting of the VL and VH domains of a single arm of an antibody; and the like). In various embodiments, polyclonal and monoclonal antibodies are useful, as are isolated human or humanized antibodies, or functional fragments thereof.

Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

In another embodiment, the measurement comprises evaluating a presence, absence, or level of a nucleic acid. A person skilled in the art will appreciate that a number of methods can be used to detect or quantify the DNA/RNA levels of appropriate markers.

Gene expression can be measured using, for example, low-to-mid-plex techniques, including but not limited to reporter gene assays, Northern blot, fluorescent in situ hybridization (FISH), and reverse transcription PCR (RT-PCR). Gene expression can also be measured using, for example, higher-plex techniques, including but not limited, serial analysis of gene expression (SAGE), DNA microarrays. Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP. A person skilled in the art will appreciate that a number of methods can be used to detect or quantify the level of RNA products of the biomarkers within a sample, including arrays, such as microarrays, RT-PCR (including quantitative PCR), nuclease protection assays and Northern blot analyses.

Exemplary Cancers and Patients

In some embodiments the invention provides a method for determining a cancer treatment and/or comprises a patient's tumor or cancer cell specimen. A cancer or tumor refers to an uncontrolled growth of cells and/or abnormal increased cell survival and/or inhibition of apoptosis which interferes with the normal functioning of the bodily organs and systems. A subject that has a cancer or a tumor is a subject having objectively measurable cancer cells present in the subject's body. Included in this invention are benign and malignant cancers, as well as dormant tumors or micrometastases. Cancers which migrate from their original location and seed vital organs can eventually lead to the death of the subject through the functional deterioration of the affected organs.

In various embodiments, the invention is applicable to pre-metastatic cancer, or metastatic cancer. Metastasis refers to the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are often detected through the sole or combined use of magnetic resonance imaging (MRI) scans, computed tomography (CT) scans, blood and platelet counts, liver function studies, chest X-rays and bone scans in addition to the monitoring of specific symptoms.

The methods described herein are directed toward the prognosis of cancer, diagnosis of cancer, treatment of cancer, and/or the diagnosis, prognosis, treatment, prevention or amelioration of growth, progression, and/or metastases of malignancies and proliferative disorders associated with increased cell survival, or the inhibition of apoptosis. In some embodiments, the cancer is a hematologic cancer, including, but not limited to, acute myelogenous leukemia (AML), multiple myeloma, follicular lymphoma, acute lymphoblastic leukemia (ALL), chronic lymphocytic leukemia, and non-Hodgkin's lymphoma including, but not limited to, mantle cell lymphoma and diffuse large B-cell lymphoma. In some embodiments, the cancer is a solid tumor, including, but not limited to, non-small lung cell carcinoma, ovarian cancer, and melanoma.

In some embodiments, the invention relates to one or more of the following cancers: acute lymphoblastic leukemia (ALL), acute myeloid leukemia (AML), adrenocortical carcinoma, AIDS-related cancers, anal cancer, appendix cancer, astrocytoma (e.g. childhood cerebellar or cerebral), basal-cell carcinoma, bile duct cancer, bladder cancer, bone tumor (e.g. osteosarcoma, malignant fibrous histiocytoma), brainstem glioma, brain cancer, brain tumors (e.g. cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's lymphoma, carcinoid tumors, central nervous system lymphomas, cerebellar astrocytoma, cervical cancer, chronic lymphocytic leukemia (CLL), chronic myelogenous leukemia (CML), chronic myeloproliferative disorders, colon cancer, cutaneous t-cell lymphoma, desmoplastic small round cell tumor, endometrial cancer, ependymoma, esophageal cancer, Ewing's sarcoma, extracranial germ cell tumor, extragonadal germ cell tumor, extrahepatic bile duct cancer, eye cancer, gallbladder cancer, gastric (stomach) cancer, gastrointestinal stromal tumor (GIST), germ cell tumor (e.g. extracranial, extragonadal, ovarian), gestational trophoblastic tumor, gliomas (e.g. brain stem, cerebral astrocytoma, visual pathway and hypothalamic), gastric carcinoid, head and neck cancer, heart cancer, hepatocellular (liver) cancer, hypopharyngeal cancer, hypothalamic and visual pathway glioma, intraocular melanoma, islet cell carcinoma (endocrine pancreas), kidney cancer (renal cell cancer), laryngeal cancer, leukemias (e.g. acute lymphocytic leukemia, acute myelogenous leukemia, chronic lymphocytic leukemia, chronic myeloid leukemia, hairy cell), lip and oral cavity cancer, liposarcoma, liver cancer, lung cancer (e.g. non-small cell, small cell), lymphoma (e.g. AIDS-related, Burkitt, cutaneous T-cell Hodgkin, non-Hodgkin, primary central nervous system), medulloblastoma, melanoma, Merkel cell carcinoma, mesothelioma, metastatic squamous neck cancer, mouth cancer, multiple endocrine neoplasia syndrome, multiple myeloma, mycosis fungoides, myelodysplastic syndromes, myelodysplastic/myeloproliferative diseases, myelogenous leukemia, myeloid leukemia, myeloid leukemia, myeloproliferative disorders, chronic, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma, ovarian cancer, pancreatic cancer, pancreatic cancer, paranasal sinus and nasal cavity cancer, parathyroid cancer, penile cancer, pharyngeal cancer, pheochromocytoma, pineal astrocytoma and/or germinoma, pineoblastoma and supratentorial primitive neuroectodermal tumors, pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter, retinoblastoma, rhabdomyosarcoma, salivary gland cancer, sarcoma (e.g. Ewing family, Kaposi, soft tissue, uterine), Sézary syndrome, skin cancer (e.g. nonmelanoma, melanoma, merkel cell), small cell lung cancer, small intestine cancer, soft tissue sarcoma, squamous cell carcinoma, squamous neck cancer, stomach cancer, supratentorial primitive neuroectodermal tumor, t-cell lymphoma, testicular cancer, throat cancer, thymoma and thymic carcinoma, thyroid cancer, trophoblastic tumors, ureter and renal pelvis cancers, urethral cancer, uterine cancer, uterine sarcoma, vaginal cancer, visual pathway and hypothalamic glioma, vulvar cancer, Waldenström macroglobulinemia, and Wilms tumor.

In one embodiment, the cancer is AML. AML is the second most common leukemia, with approximately 13,000 newly diagnosed cases and 9,000 deaths annually in the US. Although approved therapies exist, the prognosis of many leukemia patients is poor and the likelihood of successful treatment is low. The current standard of care for AML is induction cytosine arabinoside (ara-C) in combination with an anthracycline agent (such as, for example, daunorubicin, idarubicine or mitoxantrone). This therapeutic regimen is typically followed by administration of high dose cytarabine and/or stem cell transplantation. These treatments have improved outcome in young patients. Progress has also been made in the treatment of acute promyelocytic leukemia, where targeted therapy with all-trans retinoic acid (ATRA) or arsenic trioxide have resulted in excellent survival rates. However, patients over 60, a population which represents the vast majority of AML cases, remain a therapeutic enigma. Although 65-85% of patients initially respond to existing treatments, 65% of such responders undergo relapse, and many patients succumb to the disease. For at least this reason and because the afore-mentioned treatments may have severe side effects, the inventive predictive test can guide use of the treatment that mitigates these litigations. In some embodiments, the present invention improves the likelihood of successful treatment by matching the right patient to the right treatment. Further, there are currently no tests to predict AML patient response to treatment.

The term subject, as used herein unless otherwise defined, is a mammal, e.g., a human, mouse, rat, hamster, guinea pig, dog, cat, horse, cow, goat, sheep, pig, or non-human primate, such as a monkey, chimpanzee, or baboon. The terms "subject" and "patient" are used interchangeably.

Exemplary Specimens

In certain embodiments, the specimen is a human tumor-derived cell line. In certain embodiments, the specimen is a cancer stem cell. In other embodiments, the specimen is derived from the biopsy of a solid tumor, such as, for example, a biopsy of a colorectal, breast, prostate, lung, pancreatic, renal, or ovarian primary tumor.

In certain embodiments, the specimen is derived from the biopsy of a non-solid tumor, such as, for example, any of the cancer described herein. In specific embodiments, the specimen is derived from the biopsy of a patient with multiple myeloma, acute myelogenous leukemia, acute lymphocytic leukemia, chronic lymphogenous leukemia, mantle cell lymphoma, diffuse large B-cell lymphoma, and non-Hodgkin's lymphoma. In a specific embodiment, the specimen is a multiple myeloma cell that is enriched by selection from a biopsy sample with an anti-CD138 antibody bound to a solid matrix or bead. In a specific embodiment, the specimen is an acute myelogenous leukemia cell that is enriched by binding to a CD45-directed antibody. In a specific embodiment, the specimen is a chronic lymphogenous leukemia or diffuse large B-cell lymphoma that is enriched by non-B cell depletion.

In some embodiments, the specimen is derived from a circulating tumor cell.

BH3 Profiling

In various embodiments, the invention comprises BH3 profiling. In various embodiments, the invention comprises BH3 profiling in which at least two, or three, or four, or five, or six, or seven, or eight, or nine, or ten BH3 peptides are evaluated at once. In some embodiments, the present methods comprise a multipeptide analysis, as opposed to an evaluation of a single BH3 peptide. In some embodiments, a panel of BH3 peptides is screened on a single patient specimen.

BH3 profiling and reagents useful for such a method is described in U.S. Pat. Nos. 7,868,133; 8,221,966; and 8,168,755 and US Patent Publication No. 2011/0130309, the contents of which are hereby incorporated by reference in their entireties.

Briefly, without wishing to be bound by theory, as a result of aberrant phenotypes, cancer cells develop blocks in apoptosis pathways. These blocks make cancer cells both resistant to some therapies, and, surprisingly, make some cancer cells sensitive to other therapies. The concept of "oncogene addiction" describes the phenomena of the acquired dependence of cancer cells on, or addiction to, particular proteins for survival. BH3 profiling determines if such a dependence on certain apoptosis regulating proteins occurs in given cancer cells, and identifies the dependent protein. Cancer cells can be, but are not always, pre-set to undergo apoptosis and this is a function of these cells being dependent on any, or all of the anti-apoptotic Bcl-2 family proteins for their otherwise unintended survival. This provides insight into the likelihood of a cancer cell to respond to treatment.

Cancer cells, without wishing to be bound by theory, exhibit abnormalities, such as DNA damage, genetic instability, abnormal growth factor signaling, and abnormal or missing matrix interactions, any of which should typically induce apoptosis through the intrinsic (mitochondrial) apoptosis pathway. However, rather than respond to these apoptosis signals cancer cells survive. Often, in doing so, these cells become highly dependent on selected blocks to chronic apoptosis signals. This adaptation provides a survival mechanism for the cancer cells; however, these adaptations can also make cancer cells susceptible to particular apoptosis inducing therapies. A crucial event that commits a cell to die by intrinsic apoptosis is the permeabilization of the mitochondrial outer membrane (MOMP) and the release of molecules that activate the effector caspases. In many cases, MOMP is the point of no return in the intrinsic apoptosis pathway. The Bcl-2 family proteins are the key regulators of MOMP, and their activity is linked to the onset of lymphoid and several solid tumor cancers and is believed in many cancers to be the key mediator of resistance to chemotherapy.

Bcl-2 proteins are regulated by distinct protein-protein interactions between pro-survival (anti-apoptotic) and pro-apoptotic members. These interactions occur primarily through BH3 (Bcl-2 homology domain-3) mediated binding. Apoptosis-initiating signaling occurs for the most part upstream of the mitochondria and causes the translocation of short, BH3-only, Bcl-2 family members to the mitochondria where they either activate or sensitize MOMP. The activator BH3 only proteins, Bim and Bid, bind to and directly activate the effector, pro-apoptotic proteins Bax and Bak, and also bind to and inhibit the anti-apoptotic Bcl-2 family proteins, Bcl-2, MCL1., Bfl-1, Bcl-w and Bcl-xL. The sensitizer BH3 proteins, Bad, Bik, Noxa, Hrk, Bmf and Puma, bind only to the anti-apoptotic Bcl-2 family proteins, Bcl-2, MCL1., Bfl-1, Bcl-w and Bcl-xL, blocking their anti-apoptotic functions. Without wishing to be bound by theory, each sensitizer protein has a unique specificity profile. For example, Noxa (A and B) bind with high affinity to MCL1., Bad binds to Bcl-xL and Bcl-2 but only weakly to MCL1., and Puma binds well to all three targets. An anti-apoptotic function of these proteins is the sequestering of the activator BH3 protein Bim and Bid. Displacement of these activators by sensitizer peptides results in Bax/Bak-mediated apoptotic commitment. These interactions can have various outcomes, including, without limitation, homeostasis, cell death, sensitization to apoptosis, and blockade of apoptosis.

A defining feature of cancer cells in which apoptotic signaling is blocked is an accumulation of the BH3 only activator proteins at the mitochondrial surface, a result of these proteins being sequestered by the anti-apoptotic proteins. This accumulation and proximity to their effector target proteins accounts for increased sensitivity to antagonism of Bcl-2 family proteins in the "BH3 primed" state.

In some embodiments, a cell yielding a high apoptotic response to Noxa (A or B) is MCL1. primed, while a high response to the peptide Bad indicates that Bcl-xL or Bcl-2 provides the apoptotic block. In some embodiments, Puma reflects pan-Bcl-2 family priming. In this way, cells that are dependent on either MCL1. or Bcl-xL, on both proteins, or on several Bcl-2 family members are readily distinguished so that appropriate treatment may be tailored accordingly. The distinctions in mitochondrial response to these peptides guides the use of therapies that are known to work through pathways that funnel into either MCL1. or Bcl-xL affected intrinsic signaling. The use of a Bcl-2 inhibiting or a MCL1. inhibiting compound may be indicated in such cases. In some embodiments, the present methods also indicate or contraindicate therapies that target entities upstream of MCL1. or Bcl-xL.

BH3 profiling assay identifies when a cancer cell is in the primed state, as well as in which configuration the priming has occurred and this has predictive value.

Exemplary Clinical Factors and Additional Biomarkers

In some embodiments, the invention comprises the evaluation of clinical factors. In some embodiments, the invention comprises an evaluation of BH3 profiling and/or clinical factors to assess a patient response. In some embodiments, a clinical factor that provides patient response information in combination with a BH3 profiling study may not be linked to apoptosis. In some embodiments, a clinical factor is non-apoptosis affecting.

In one embodiment, the clinical factor is shown in Table 3.

In one embodiment, the clinical factor is one or more of age, cytogenetic status, performance, histological subclass, gender, and disease stage In one embodiment, the clinical factor is age. In one embodiment, the patient age profile is classified as over about 10, or over about 20, or over about 30, or over about 40, or over about 50, or over about 60, or over about 70, or over about 80 years old.

In one embodiment, the clinical factor is cytogenetic status. In some cancers, such as Wilms tumor and retinoblastoma, for example, gene deletions or inactivations are responsible for initiating cancer progression, as chromosomal regions associated with tumor suppressors are commonly deleted or mutated. For example, deletions, inversions, and translocations are commonly detected in chromosome region 9p21 in gliomas, non-small-cell lung cancers, leukemias, and melanomas. Without wishing to be bound by theory, these chromosomal changes may inactivate the tumor suppressor cyclin-dependent kinase inhibitor 2A. Along with these deletions of specific genes, large portions of chromosomes can also be lost. For instance, chromosomes 1p and 16q are commonly lost in solid tumor cells. Gene duplications and increases in gene copy numbers can also contribute to cancer and can be detected with transcriptional analysis or copy number variation arrays. For example, the chromosomal region 12q13-q14 is amplified in many sarcomas. This chromosomal region encodes a binding protein called MDM2, which is known to bind to a tumor suppressor called p53. When MDM2 is amplified, it prevents p53 from regulating cell growth, which can result in tumor formation. Further, certain breast cancers are associated with overexpression and increases in copy number of the ERBB2 gene, which codes for human epidermal growth factor receptor 2. Also, gains in chromosomal number, such as chromosomes 1q and 3q, are also associated with increased cancer risk.

Cytogenetic status can be measured in a variety of manners known in the art. For example, FISH, traditional karyotyping, and virtual karyotyping (e.g. comparative genomic hybridization arrays, CGH and single nucleotide polymorphism arrays) may be used. For example, FISH may be used to assess chromosome rearrangement at specific loci and these phenomenon are associated with disease risk status. In some embodiments, the cytogenetic status is favorable, intermediate, or unfavorable.

In one embodiment, the clinical factor is performance. Performance status can be quantified using any system and methods for scoring a patient's performance status are known in the art. The measure is often used to determine whether a patient can receive chemotherapy, adjustment of dose adjustment, and to determine intensity of palliative care. There are various scoring systems, including the Karnofsky score and the Zubrod score. Parallel scoring systems include the Global Assessment of Functioning (GAF) score, which has been incorporated as the fifth axis of the Diagnostic and Statistical Manual (DSM) of psychiatry. Higher performance status (e.g., at least 80%, or at least 70% using the Karnofsky scoring system) may indicate treatment to prevent progression of the disease state, and enhance the patient's ability to accept chemotherapy and/or radiation treatment. For example, in these embodiments, the patient is ambulatory and capable of self care. In other embodiments, the evaluation is indicative of a patient with a low performance status (e.g., less than 50%, less than 30%, or less than 20% using the Karnofsky scoring system), so as to allow conventional radiotherapy and/or chemotherapy to be tolerated. In these embodiments, the patient is largely confined to bed or chair and is disabled even for self-care.

The Karnofsky score runs from 100 to 0, where 100 is "perfect" health and 0 is death. The score may be employed at intervals of 10, where: 100% is normal, no complaints, no signs of disease; 90% is capable of normal activity, few symptoms or signs of disease, 80% is normal activity with some difficulty, some symptoms or signs; 70% is caring for self, not capable of normal activity or work; 60% is requiring some help, can take care of most personal requirements; 50% requires help often, requires frequent medical care; 40% is disabled, requires special care and help; 30% is severely disabled, hospital admission indicated but no risk of death; 20% is very ill, urgently requiring admission, requires supportive measures or treatment; and 10% is moribund, rapidly progressive fatal disease processes.

The Zubrod scoring system for performance status includes: 0, fully active, able to carry on all pre-disease performance without restriction; 1, restricted in physically strenuous activity but ambulatory and able to carry out work of a light or sedentary nature, e.g., light house work, office work; 2, ambulatory and capable of all self-care but unable to carry out any work activities, up and about more than 50% of waking hours; 3, capable of only limited self-care, confined to bed or chair more than 50% of waking hours; 4, completely disabled, cannot carry on any self-care, totally confined to bed or chair; 5, dead.

In one embodiment, the clinical factor is histological subclass. In some embodiments, histological samples of tumors are graded according to Elston & Ellis, Histopathology, 1991, 19:403-10, the contents of which are hereby incorporated by reference in their entirety.

In one embodiment, the clinical factor is gender. In one embodiment, the gender is male. In another embodiment the gender is female.

In one embodiment, the clinical factor is disease stage. By way of non-limiting example, using the overall stage grouping, Stage I cancers are localized to one part of the body; Stage II cancers are locally advanced, as are Stage III cancers. Whether a cancer is designated as Stage II or Stage III can depend on the specific type of cancer. In one non-limiting example, Hodgkin's disease, Stage II indicates affected lymph nodes on only one side of the diaphragm, whereas Stage III indicates affected lymph nodes above and below the diaphragm. The specific criteria for Stages II and III therefore differ according to diagnosis. Stage IV cancers have often metastasized, or spread to other organs or throughout the body.

In some embodiments, the clinical factor is the French-American-British (FAB) classification system for hematologic diseases (e.g. indicating the presence of dysmyelopoiesis and the quantification of myeloblasts and erythroblasts). In one embodiment, the FAB for acute lymphoblastic leukemias is L1-L3, or for acute myeloid leukemias is M0-M7. In another embodiment, the method further comprises a measurement of an additional biomarker selected from mutational status, single nucleotide polymorphisms, steady state protein levels, and dynamic protein levels. In another embodiment, the method further comprises predicting a clinical response in the patient. In another embodiment, the clinical response is about 1, about 2, about 3, or about 5 year progression/event-free survival.

A variety of clinical factors have been identified, such as age profile and performance status. A number of static measurements of diagnosis have also been utilized, such as cytogenetics and molecular events including, without limitation, mutations in the genes MLL, AML/ETO, Flt3-ITD, NPM1 (NPMc+), CEBPI, IDH1, IDH2, RUNX1, ras, and WT1 and in the epigenetic modifying genes TET2 and ASXL, as well as changes in the cell signaling protein profile.

In some embodiments, the preventive methods comprise administering a treatment to a patient that is likely to be afflicted by cancer as guided by the methods described herein. In some embodiments, a subject is likely to be afflicted by cancer if the subject is characterized by one or more of a high risk for a cancer, a genetic predisposition to a cancer (e.g. genetic risk factors), a previous episode of a cancer (e.g. new cancers and/or recurrence), a family history of a cancer, exposure to a cancer-inducing agent (e.g. an environmental agent), and pharmacogenomic information (the effect of genotype on the pharmacokinetic, pharmacodynamic or efficacy profile of a therapeutic).

In some embodiments, a subject is likely to be afflicted by cancer if the subject is characterized by a high risk for a cancer. In some embodiments, a subject is likely to be afflicted by cancer if the subject is characterized by a genetic predisposition to a cancer. In some embodiments, a genetic predisposition to a cancer is a genetic clinical factor, as is known in the art. Such clinical factors may include, by way of example, HNPCC, MLH1, MSH2, MSH6, PMS1, PMS2 for at least colon, uterine, small bowel, stomach, urinary tract cancers. In some embodiments, a subject is likely to be afflicted by cancer if the subject is characterized by a previous episode of a cancer. In some embodiments, the subject has been afflicted with 1, or 2, or 3, or 4, or 5, or 6, previous episodes of cancer. In some embodiments, a subject is likely to be afflicted by cancer if the subject is characterized by a family history of a cancer. In some embodiments, a parent and/or grandparent and/or sibling and/or aunt/uncle and/or great aunt/great uncle, and/or cousin has been or is afflicted with a cancer. In some embodiments, a subject is likely to be afflicted by cancer if the subject is characterized by exposure to a cancer-inducing agent (e.g. an environmental agent). For example, exposing skin to strong sunlight is a clinical factor for skin cancer. By way of example, smoking is a clinical factor for cancers of the lung, mouth, larynx, bladder, kidney, and several other organs.

Further, in some embodiments, the any one of the following clinical factors may be useful in the methods described herein: gender; genetic risk factors; family history; personal history; race and ethnicity; features of the certain tissues; various benign conditions (e.g. non-proliferative lesions); previous chest radiation; carcinogen exposure and the like.

Further still, in some embodiments, the any one of the following clinical factors may be useful in the methods described herein: one or more of a cell surface marker CD33, a cell surface marker CD34, a FLT3 mutation status, a p53 mutation status, a phosphorylation state of MEK-1 kinase, and phosphorylation of serine at position 70 of Bcl-2.

In some embodiments, the clinical factor is expression levels of the cytokines, including, without limitation, interleukin-6. In some embodiments, interleukin-6 levels will correlate with likelihood of response in MM patients, including a poor patient prognosis or a good patient prognosis.

In certain embodiments, the likelihood of response is determined by assessing a percent priming. In certain embodiments, the priming is defined by the following equation:

$$\% \text{ Priming} = \left[100*\left(\frac{DMSO\ AUC - \text{Peptide}_1\ AUC}{DMSO\ AUC - CCCP_{avg}AUC}\right)\right]\text{Peptide}_1 + \\ \left[100*\left(\frac{DMSO\ AUC - \text{Peptide}_2\ AUC}{DMSO\ AUC - CCCP_{avg}AUC}\right)\right]\text{Peptide}_2 + \cdots /(n\text{ peptides})$$

in which the AUC comprises either area under the curve or signal intensity; the DMSO comprises the baseline negative control; and the CCCP (Carbonyl cyanide m-chlorophenyl hydrazone) comprises an effector of protein synthesis by serving as uncoupling agent of the proton gradient established during the normal activity of electron carriers in the electron transport chain in the mitochondria comprises the baseline positive control. In some embodiments, the area under the curve is established by homogenous time-resolved fluorescence (HTRF). In some embodiments, the time occurs over a window from between about 0 to about 300 min to about 0 to about 30 min. In some embodiments, the area under the curve is established by fluorescence activated cell sorting (FACS). In some embodiments, the signal intensity is a single time point measurement that occurs between about 5 min and about 300 min.

In another embodiment, the method comprises measuring the BH3 profiling assay and one or more of a cell surface marker CD33, a cell surface marker CD34, a FLT3 mutation status, a p53 mutation status, a phosphorylation state of MEK-1 kinase, and phosphorylation of serine at position 70 of Bcl-2; and correlating to efficacy in treating AML patients with cytarabine or cytarabine-based chemotherapy and/or azacytidine.

In another embodiment, the method comprises measuring the BH3 profiling assay and one or more of a cell surface marker CD33, a cell surface marker CD34, a FLT3 mutation status, a p53 mutation status, a phosphorylation state of MEK-1 kinase, and phosphorylation of serine at position 70 of Bcl-2; and correlating to efficacy in treating MM patients with chemotherapy.

In still another embodiment, the cancer is AML and/or MM and the clinical factor is age profile and/or cytogenetic status; or the cancer is AML and/or MM and the cancer treatment is cytarabine or cytarabine-based chemotherapy and/or azacytidine, or the cancer treatment is cytarabine or cytarabine-based chemotherapy and/or azacytidine and the clinical factor is age profile and/or cytogenetic status, or the cancer treatment is cytarabine or cytarabine-based chemotherapy and/or azacytidine; the cancer is AML and/or MM; and the clinical factor is age profile and/or cytogenetic status.

The invention also provides kits that can simplify the evaluation of tumor or cancer cell specimens. A typical kit of the invention comprises various reagents including, for example, one or more agents to detect a BH3 peptide. A kit may also comprise one or more of reagents for detection, including those useful in various detection methods, such as, for example, antibodies. The kit can further comprise materials necessary for the evaluation, including welled plates, syringes, and the like. The kit can further comprise a label or printed instructions instructing the use of described reagents. The kit can further comprise an treatment to be tested.

The term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the invention, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

Embodiments of this invention is further illustrated by the following non-limiting examples.

EXAMPLES

Example 1

Studies Using AML Patient-Based Cohorts

Johns Hopkins University Hospitals and Clinics has in its tissue repository viably frozen AML patient specimens from two previously conducted clinical trials. 63 peripheral blood and bone marrow samples from newly diagnosed patients with AML or MDS enrolled on protocols NCT00795002 (J0856), NCT00407966 (J0669), or NCT01349972 (J1101) from Johns Hopkins University were obtained and analyzed. Patients were treated with FLAM: alvocidib (Flavopiridol), Ara-C and Mitoxantrone (n=54) or 7+3 (Ara C and Daunorubicin, n=9). Complete response, characterized by less than 5% myeloblasts with normal maturation of all cell lines, an ANC. 1000/μL and platelet count. 100,000/μL, absence of blast in peripheral blood, absence of leukemic cells in the marrow, clearance of cytogenetics associated with disease, and clearance of previous extramedullary disease. Overall patient characteristics were provided by Johns Hopkins University after BH3 profiling was completed and are summarized in Table 1, including patient age, cytogenetic risk, FLT-3 mutation, NPM1 Mutation, MDS/Marrow Disorder History, Prior Chemotherapy History, BM Blast %, WBC Count at Diagnosis, and response to the therapy. Individual patient characteristics are listed in Table 2.

TABLE 1

Patient Summary

|  | # Pos/Total Number |
|---|---|
| Number of Patients | 63 |
| Median Age | 58 |
| Median BM Blast % | 38 |
| Median WBC Count at Diagnosis | 6020 |
| Adverse Cytogenetics | 26/63 |
| Intermediate Cytogenetics | 34/63 |
| Favorable Cytogenetics | 3/63 |
| FLT3 Mutation | 11/62 |
| NPM1 Mutation | 10/37 |
| MDS/Marrow Disorder History | 25/63 |
| Prior Chemo History | 7/63 |
| FLAM Treatment | 54/63 |
| Complete Remission | 29/63 |

TABLE 2

Patient Characteristics

| EIN | UPI | Protocol | Diagnosis | Source | Age | Cytogenetic Risk | FLT-3 | NPM1 | MDS/Marrow Disorder Hx | Prior Chemo Hx | % BM Blast | WBC at Dx | Tx | Response to Induction |
|---|---|---|---|---|---|---|---|---|---|---|---|---|---|---|
| 577 | 13566 | J0669 | AML | Marrow | 59 | INT | Neg | Not Done | Likely | No | 25 | 9880 | FLAM/IT Chemo | CR |
| 580 | 13548 | J0669 | AML | Marrow | 61 | INT | Neg | Not Done | No | No | 20 | 1500 | FLAM | CR |

TABLE 2-continued

Patient Characteristics

| EIN | UPI | Protocol | Diagnosis | Source | Age | Cyto-genetic Risk | FLT-3 | NPM1 | MDS/Marrow Disorder Hx | Prior Chemo Hx | % BM Blast | WBC at Dx | Tx | Response to Induction |
|---|---|---|---|---|---|---|---|---|---|---|---|---|---|---|
| 582 | 20866 | J0856 | AML | Blood | 49 | INT | Neg | Not Done | No | No | 6 | 2130 | FLAM | CR |
| 583 | 22844 | J0856 | Unknown | Blood | 57 | ADV | Neg | Neg | No | Yes | 13 | 2530 | FLAM | CR |
| 584 | 20345 | J0856 | Unknown | Marrow | 54 | INT | Neg | Not Done | Likely | No | 79 | 8030 | FLAM | CR |
| 585 | 21666 | J0856 | AML | Blood | 60 | INT | Pos (ITD) | Neg | No | No | 48 | 31330 | FLAM/IT Chemo | CR |
| 586 | 20566 | J0856 | AML | Marrow | 58 | ADV | Pos (ITD) | Pos | No | NO | 94 | 38180 | FLAM | CR |
| 587 | 21845 | J0856 | AML | Marrow | 49 | FAV | Neg | Neg | No | No | 91 | 75630 | FLAM | CR |
| 589 | 21885 | J0856 | AML | Marrow | 53 | ADV | Neg | Neg | Yes | Yes | 5 | 2640 | FLAM | CR |
| 591 | 22228 | J0856 | AML | Marrow | 67 | ADV | Neg | Not Done | Yes | No | 58 | 890 | FLAM | CR |
| 597 | 19064 | J0856 | MDS | Marrow | 64 | INT | Neg | Neg | Yes | Yes | 13 | 10800 | FLAM | CR |
| 598 | 21905 | J0856 | AML | Blood | 59 | INT | Pos (ITD) | Neg | No | No | 71 | 10390 | FLAM | CR |
| 599 | 20725 | J0856 | AML | Blood | 52 | ADV | Neg | Not Done | Yes | No | 12 | 36990 | FLAM | CR |
| 603 | 22424 | J0856 | AML | Marrow | 73 | INT | Neg | Not Done | Yes | Yes | 83 | 10160 | FLAM | CR |
| 605 | 20284 | J0856 | AML | Blood | 54 | INT | Neg | Pos | No | No | 74 | 46690 | FLAM/IT Chemo | CR |
| 615 | 21905 | J1101 | AML | Blood | 59 | INT | Pos (ITD) | Neg | No | No | 71 | 103900 | FLAM | CR |
| 620 | 2569 | J1101 | AML | Marrow | 69 | INT | Neg | Neg | Yes | No | 56 | 4580 | FLAM | CR |
| 621 | 2590 | J1101 | AML | Blood | 60 | INT | Neg | Neg | No | No | 10 | 25430 | FLAM | CR |
| 628 | 2453 | J1101 | AML | Blood | 63 | INT | Neg | Pos | Yes | No | 6 | 9350 | FLAM | CR |
| 631 | 2190 | J1101 | MDS | Marrow | 37 | INT | N/A | N/A | Yes | No | 12 | 1640 | FLAM | CR |
| 634 | 2526 | J1101 | AML | Blood | 57 | INT | Neg | Pos | No | No |  | 71340 | FLAM | CR |
| 636 | 2539 | J1101 | AML | Marrow | 48 | INT | Neg | Neg | Yes | No | 12 | 1720 | FLAM | CR |
| 638 | 2671 | J1101 | AML | Marrow | 62 | INT | Neg | Neg | No | No | 47 | 2600 | 7 + 3 Ara C + Dauno | CR |
| 612 | 2754 | J1101 | AML | Marrow | 63 | ADV | Neg | Neg | No | No | 91 | 32130 | 7 + 3 Ara C + Dauno | Max RD |
| 624 | 2455 | J1101 | AML | Blood | 55 | ADV | Neg | Neg | Yes | No | 6 | 1870 | FLAM | MAX RD |
| 588 | 20784 | J0856 | AML | Blood | 68 | INT | Pos (ITD) | Neg | No | No | 79 | 53580 | FLAM | MRD-F |
| 592 | 21627 | J0856 | AML | Blood | 51 | INT | Neg | Not Done | No | No | 70 | 420 | FLAM | MRD-F |
| 593 | 20744 | J0856 | AML | Marrow | 57 | INT | Neg | Not Done | Yes | No | 14 | 900 | FLAM | MRD-F |
| 607 | 20384 | J0856 | AML | Marrow | 52 | ADV | Neg | Not Done | yes | No | 38 | 1440 | FLAM | MRD-F |
| 610 | 25524 | J1101 | AML | Marrow | 45 | ADV | Neg | Neg | Yes | Yes | 29 | 1560 | FLAM | MRD-F |
| 622 | 2578 | J1101 | AML | Marrow | 68 | ADV | Neg | Neg | No | No | 81 | 4900 | FLAM | MRD-F |
| 626 | 2561 | J1101 | AML | Blood | 58 | INT | Neg | Pos (ITD) | No | No | 64 | 18930 | 7 + 3 Ara C + Dauno | MRD-M |
| 627 | 2669 | J1101 | MDS | Marrow | 65 | ADV | Neg | Neg | Yes | No | 1 | 17850 | FLAM | MRD-M |
| 630 | 2694 | J1101 | AML | Marrow | 57 | ADV | Neg | Neg | No | No | 71 | 1820 | FLAM | MRD-M |
| 596 | 22065 | J0856 | M6 | Blood | 71 | ADV | Neg | Not Done | No | NO | 4 | 7080 | FLAM | PR-TD |
| 637 | 2747 | J1101 | AML | Marrow | 53 | INT | Neg | Pos | No | No | 25 | 1295 | FLAM | PR-TD |
| 590 | 18523 | J0856 | Unknown | Marrow | 50 | INT | Neg | Not Done | No | No | 81 | 6020 | FLAM | TF |
| 594 | 19123 | J0856 | AML | Marrow | 51 | ADV | Neg | Neg | No | No | 79 | 9920 | FLAM | TF |
| 595 | 20945 | J0856 | AML | Blood | 70 | ADV | Neg | Neg | No | No | 18 | 1830 | FLAM | TF |
| 601 | 20965 | J0856 | AML | Blood | 54 | INT | Neg | Neg | Likely | No | 17 | 1320 | FLAM | TF |
| 602 | 18843 | J0856 | AML | Marrow | 65 | ADV | Neg | Neg | Yes | Yes | 24 | 980 | FLAM | TF |
| 604 | 19085 | J0856 | AML | Marrow | 65 | FAV | Neg | Neg | No | No | 88 | 71670 | FLAM | TF |
| 606 | 20564 | J0856 | AML | Blood | 61 | INT | Neg | Neg | NO | No | 89 | 37350 | FLAM | TF |
| 608 | 2328 | J1101 | AML | Blood | 67 | ADV | Neg | Neg | No | No | 66 | 2440 | 7 + 3 Ara C + Dauno | TF |
| 614 | 2514 | J1101 | AML | Blood | 58 | ADV | Neg | Neg | Yes | No | 3 | 1770 | 7 + 3 Ara C + Dauno | TF |
| 616 | 2653 | J1101 | AML | Marrow | 65 | ADV | Neg | Neg | No | No | 53 | 1100 | 7 + 3 Ara C + Dauno | TF |

TABLE 2-continued

Patient Characteristics

| EIN | UPI | Protocol | Diagnosis | Source | Age | Cyto-genetic Risk | FLT-3 | NPM1 | MDS/Marrow Disorder Hx | Prior Chemo Hx | % BM Blast | WBC at Dx | Tx | Response to Induction |
|---|---|---|---|---|---|---|---|---|---|---|---|---|---|---|
| 619 | 2721 | J1101 | AML | Marrow | 63 | ADV | Neg | Neg | No | No | 28 | 4950 | FLAM | TF |
| 625 | 2708 | j1 | AML | Marrow | 54 | ADV | Neg | Neg | No | No | 74 | 2610 | FLAM | TF |
| 629 | 2828 | J1101 | AML | Marrow | 53 | INT | Pos (ITD) | Pos | No | No | 96 | 64840 | FLAM | TF |
| 632 | 2792 | J1101 | AML | Marrow | 22 | INT | Neg | Neg | No | No | 36 | 4130 | 7 + 3 Ara C + Dauno | TF |
| 633 | 2576 | J1101 | AML | Blood | 70 | INT | Neg | Neg | No | No | 32 | 3120 | FLAM | TF |
| 635 | 2167 | J1101 | AML | Marrow | 34 | INT | Pos (ITD) | Neg | No | No | 91 | 54300 | 7 + 3 Ara C + Dauno | TF |
| 576 | 22944 | J0669 | AML | Marrow | 56 | INT | Pos (ITD) | Neg | yes | No | 39 | 47860 | FLAM | MRD-F |
| 578 | 13068 | J0669 | AML | Unknown | 51 | ADV | Neg | Not Done | Yes | Yes | 6 | 29740 | FLAM | CR |
| 579 | 13938 | J0669 | AML | Marrow | 70 | INT | Neg | Not Done | yes | no | 38 | 4030 | FLAM | CR |
| 581 | 14337 | J0669 | AML | Marrow | 66 | FAV | Pos (ITD) | Not Done | No | No | 87 | 11800 | FLAM | MRD-F |
| 600 | 20728 | J0856 | AML | Unknown | 54 | ADV | Neg | Neg | No | No | 58 | 10780 | FLAM | CR |
| 609 | 2280 | J1101 | MDS->AML | unknown | 51 | INT | Neg | Pos | Yes | No | 5 | 11710 | FLAM | CR |
| 611 | 2357 | J1101 | AML | Blood | 64 | INT | Neg | Pos | Yes | No | 79 | 3010 | 7 + 3 Ara C + Dauno | CR |
| 613 | 2414 | J1101 | AML | Blood | 68 | ADV | Neg | Neg | No | No | 24 | 1570 | FLAM | CR |
| 617 | 2415 | J1101 | AML | Blood | 61 | INT | Pos (ITD) | Neg | Yes | No | 13 | 7770 | FLAM | MRD-F |
| 618 | 2354 | J1101 | AML | Blood | 54 | ADV | Pos (ITD) | Neg | No | No | 32 | 6780 | FLAM | MRD-M |
| 623 | 2338 | J1101 | AML | Blood | 68 | ADV | Neg | Pos | No | No | 31 | 2080 | FLAM | TF |

Mitochondrial Profiling

Briefly, frozen, extracted leukocyte samples were rapidly thawed, and cell viability was determined by Trypan Blue exclusion. Cells were washed in FACS buffer (1× PBS with 2% FBS) and immunophenotyped using fluorescently labeled CD45, CD3, and CD20 monoclonal antibodies. Cells were then resuspended in Newmeyer buffer (10 mM Trehalose, 10 mM HEPES, 80 mM KCl, 20 μM EGTA, 20 μM EDTA, 5 mM succinate, pH 7.4) for the perturbation step. The BH3 peptides were diluted in Newmeyer buffer to make working solutions resulting in final concentrations of: BIM (100 μM), BIM (0.1 μM), NOXA (100 μM), Puma (10 μM), HRK (100 μM), BAD (100 μM), and BID (1.0 μM). DMSO and CCCP were used as negative and positive peptide controls. Digitonin and oligomycin were added to individual FACS tubes, followed by the BH3 peptides. Cells were then added to the FACS tubes and incubated for 2 hours and 15 minutes at room temperature, in order for cell permeabilization, delivery of peptides or compounds, and mitochondrial depolarization to occur. After the incubation, JC-1 dye was prepared in Newmeyer buffer and added to directly to the treated cells. An additional tube of cells that was not treated with a peptide or compound was stained with propidium iodide (PI) to ensure that cells were effectively permeabilized by the digitonin. After 45 minutes of incubation with JC-1, cells were analyzed on a three laser BD FACSCanto II. AML Blasts were gated based on four parameters: 1) permeabilization (as determined by PI staining), 2) singlet discrimination based on SSC, 3) CD45 dim and CD3/CD20 negative, and 4) SSC low. The median JC-1 red fluorescence of the gated blast population was then used to calculate % depolarization as compared to DMSO (negative) and CCCP (positive) controls. Cytogenetic Risk Status Determination Cytogenetic analysis was provided by Johns Hopkins University. Individual Patient cytogenetic risk classification (Favorable, Intermediate, and Adverse) was determined from the Cancer and Leukemia Group B (CALGB) guidelines: Favorable=inv16, t(8:21), T(15;17) intermediate=diploid, Unfavorable=−5, −7, +8, t(6;9), 11q, PH1+, 3 unrelated cytogenetic abnormalities, etc.

Statistical Analysis: For each peptide, the percentage priming was calculated using the following formula that determines the priming based on the DMSO negative control as completely unprimed and the CCCP as a 100% primed reference:

$$\text{Percentage Priming} = \left[1 - \frac{(\text{Peptide} - CCCP)}{(DMSO - CCCP)}\right] \times 100$$

For analysis, all patients not classified as CR were treated as non-responders [Minimal Residual Disease (MRD), Partial Remission (PR), and TF (treatment failure)]. Student's t-tests, Mann-Whitney rank-sum non-parametric tests, multi-variate logistic regression, and ROC curve analyses, between the BH3 peptides (and other tumor characteristics, such as cytogenetics, etc.) and response, were calculated using GraphPad Prism Version 5.04 and MedCalc Version 14.8.1.

Mitochondrial Profiling of AML Patient Samples Enrolled on FLAM Protocols A total of 63 patient samples were received and processed, and those samples are summarized in Tables 1 and 2. Full profiles were obtained from 43 of the samples, and an additional nine (9) were processed with subsets of the profiles (due to insufficient cell numbers to perform the entire assay). The remaining eleven (11) samples were of insufficient quality to determine any BH3 profiling, either due to poor signal to noise ratios (cells were already apoptotic before the assay) or inadequate cell numbers. All subsequent analyses were performed only on those samples that were successfully processed for any BH3 profiling (n=52 total).

The clinical variables obtained from the patients were compared to response to determine which, if any, of these factors influenced whether patients would respond to the therapies or not (Table 3). The only variable that was found to have a significant association with CR was the cytogenetic risk factor, where those with adverse classifications being less likely to respond to the therapies. The WBC, history of MDS, and which protocol was followed were all close to being significant, with higher WBC values and a history of MDS being associated with response to therapy. Protocol J0856 had a higher CR rate (13 CRs in 25 patients) than J1101 (8 of 25), and protocol J0669 was only represented by two patients that were successfully BH3 profiled. Age, BM Blast percentage, and NPM/FLT-3 mutation status were not significantly associated with response in this dataset.

TABLE 3

Clinical Characteristics Associations with Response

| Metric | Median NR (n = 29) | Median CR (n = 23) | Mann-Whitney p-value | Logistic Reg p-value | AUC |
|---|---|---|---|---|---|
| Age | 59 | 58 | 0.740 | 0.954 | 0.527 |
| WBC Count as DX | 3120 | 9880 | 0.078 | 0.112 | 0.643 |

TABLE 3-continued

Clinical Characteristics Associations with Response

| Metric | Median NR (n = 29) | Median CR (n = 23) | Mann-Whitney p-value | Logistic Reg p-value | AUC |
|---|---|---|---|---|---|
| BM Blast % | 53 | 36 | 0.296 | 0.332 | 0.586 |
| Cytogenic Risk | — | — | 0.024 | 0.024 | 0.663 |
| NPM Mutation | — | — | 0.295 | 0.268 | 0.571 |
| FLT3 Mutation | — | — | 0.287 | 0.259 | 0.557 |
| MDS Marrow Disorder History | — | — | 0.144 | 0.132 | 0.601 |
| Protocol Followed | — | — | 0.060 | 0.038 | 0.637 |

All BH3 individual patient data is summarized in Tables 4 and 5, which detail each BH3 peptide's ability to induce mitochondrial depolarization in the blast cells. Looking at all of the responses, the BIM 100 μM peptide resulted in the highest median depolarization (99.2%) and NOXA had the lowest overall priming (16.0%). The single peptide BH3 profiles were then compared in the patients who responded to treatment (CR) to those who did not (NR) in Table 6. No single peptide was significantly associated with response; however, the BAD peptide approached significance with a p-value of 0.09, but only had an AUC value of 0.65. This indicates that using the entire patient set, no individual BH3 peptide is sufficient to identify patients who respond to an alvocidib containing regimen, such as the FLAM treatment.

TABLE 4

BH3 Profiling Data

| EIN | Viable Cell # | % Viability | $ Blast | DMSO/ CCCP | BIM 100 μM | BIM 0.1 μM | PUMA 10 μM | NOXA 100 μM | BAD 100 μM | HRK 100 μM | BID 10 μM |
|---|---|---|---|---|---|---|---|---|---|---|---|
| 577 | 1.84E+07 | 57.2 | 16.00 | 124.80 | 32.92 | 5.65 | 12.11 | 55.03 | 18.14 | 63.42 | 7.52 |
| 580 | 3.20E+06 | 66.7 | 9.80 | 206.00 | 99.88 | 76.93 | 88.41 | 61.23 | 21.47 | 44.83 | 84.47 |
| 582 | 6.40E+06 | 9.93 | 35.20 | 95.50 | 97.85 | 28.93 | 49.81 | 0.00 | 34.24 | 31.10 | 22.74 |
| 583 | 5.00E+06 | 96.2 | 10.38 | 19.50 | 99.10 | 68.30 | 85.70 | 88.50 | — | 92.70 | 96.30 |
| 584 | 3.13E+06 | 8.15 | 12.14 | 76.18 | — | 19.91 | 33.45 | 45.55 | 2.89 | 54.70 | — |
| 585 | 5.40E+06 | 76.1 | 11.95 | 50.26 | 10.76 | 30.50 | 5.20 | 0.00 | 49.41 | 28.09 | 0.00 |
| 586 | 3.00E+06 | 61.2 | 16.58 | 35.75 | — | 36.60 | 33.30 | 69.70 | 63.00 | 28.50 | 49.20 |
| 587 | 1.14E+08 | 82.6 | 38.00 | 62.13 | 99.02 | 68.89 | 67.81 | 44.48 | 72.20 | 73.92 | 83.78 |
| 589 | 1.65E+07 | 94.9 | 19.00 | 424.30 | 100.06 | 49.13 | 83.99 | 17.22 | 79.91 | 82.17 | 76.90 |
| 591 | 7.20E+06 | 61.0 | 17.00 | 20.70 | 38.96 | 8.46 | 9.56 | 55.30 | 24.31 | — | — |
| 597 | 1.33E+07 | 55.6 | 11.00 | 40.50 | 26.02 | 0.00 | 0.17 | 46.15 | 75.58 | 33.39 | 0.00 |
| 598 | 7.69E+07 | 91.6 | 29.75 | 58.50 | 99.20 | 65.40 | 65.30 | 0.10 | 70.10 | 64.90 | 69.90 |
| 599 | 3.95E+07 | 92.1 | 30.68 | 357.84 | 99.50 | 10.10 | 34.60 | 0.90 | 11.70 | 25.50 | 16.00 |
| 603 | 4.12E+07 | 79.0 | 36.00 | 168.08 | 67.76 | 12.82 | 43.18 | 11.64 | 45.94 | 22.34 | 16.80 |
| 604 | 5.846 | 94.8 | 25.00 | 72.01 | 99.70 | 28.20 | 49.60 | 27.70 | 35.40 | 59.70 | 66.50 |
| 615 | 1.20E+07 | 91.1 | 46.46 | 178.42 | 100.00 | 10.70 | 40.20 | 4.50 | 23.80 | 11.80 | 12.50 |
| 620 | 4.00E+06 | 85.1 | 8.50 | 200.71 | 99.95 | 8.69 | 53.68 | 10.89 | 49.64 | 14.12 | 2.13 |
| 621 | 9.00E+06 | 80.0 | 37.04 | 63.60 | 100.17 | 49.49 | 71.69 | 26.03 | 56.90 | 56.11 | 74.89 |
| 628 | 8.60E+06 | 84.3 | 22.60 | 78.60 | 100.98 | 14.46 | 67.70 | 8.91 | 65.95 | 36.62 | 19.85 |
| 631 | 2.70E+06 | 62.8 | 5.60 | 60.52 | 76.37 | 30.91 | 33.77 | 14.43 | 44.87 | 7.15 | 7.22 |
| 634 | 8.70E+06 | 95.6 | 55.14 | 57.02 | 100.10 | 57.40 | 74.40 | 26.80 | 61.30 | 77.50 | 87.30 |
| 636 | 140E+07 | 63.00 | 38.97 | 25.76 | 98.60 | 47.00 | 84.40 | 0.00 | — | 0.00 | 96.90 |
| 638 | 1.12E+07 | 97.4 | 8.90 | 563.30 | 100.02 | 14.23 | 18.52 | 13.90 | 6.79 | 5.40 | 6.77 |
| 612 | 4.00E+07 | 92.6 | 11.72 | 487.02 | 100.00 | 14.40 | 50.90 | 0.00 | 55.30 | 7.8 | 23.60 |
| 624 | 2.40E+06 | 75.0 | 6.50 | 285.60 | 99.48 | 68.16 | 67.25 | 64.74 | 51.71 | 79.78 | 70.48 |
| 588 | 1.27E+07 | 95.2 | 59.52 | 20.98 | 96.10 | 62.00 | 69.30 | 21.40 | 68.60 | 81.50 | 85.40 |
| 592 | 1.90E+06 | 63.3 | 6.37 | 23.93 | 91.60 | 24.70 | 36.10 | 53.50 | 91.10 | 65.50 | 37.10 |
| 593 | 2.89E+06 | 58.3 | 15.00 | 235.54 | 100.16 | 68.96 | 80.06 | 21.66 | 77.15 | 77.34 | 72.75 |
| 607 | 7.36E+06 | 83.6 | 54.48 | 390.31 | 97.67 | 19.87 | 40.24 | 18.96 | 40.98 | 23.63 | 15.85 |
| 610 | 1.05E+06 | 26.2 | 15.60 | 73.20 | 58.50 | 2.72 | — | — | — | — | — |

TABLE 4-continued

BH3 Profiling Data

| EIN | Viable Cell # | % Viability | $ Blast | DMSO/ CCCP | BIM 100 μM | BIM 0.1 μM | PUMA 10 μM | NOXA 100 μM | BAD 100 μM | HRK 100 μM | BID 10 μM |
|---|---|---|---|---|---|---|---|---|---|---|---|
| 622 | 7.70E+06 | 79.4 | 19.72 | 78.63 | 100.98 | 14.46 | 67.70 | 9.81 | 66.95 | 36.62 | 19.85 |
| 626 | 2.06E+06 | 97.6 | 65.40 | 477.90 | 100.00 | 64.70 | 88.60 | 0.00 | 85.00 | 55.00 | 69.80 |
| 627 | 8.00E+06 | 97.6 | 10.75 | 120.50 | 99.80 | 25.10 | 55.10 | 0.00 | 5.70 | 12.20 | 76.80 |
| 630 | 1.43E+07 | 92.9 | 27.00 | 264.46 | 100.00 | 0.00 | 46.97 | 0.60 | 49.36 | 0.00 | 0.00 |
| 596 | 2.02E+06 | 92.2 | 28.82 | 104.71 | 99.70 | 46.10 | 66.40 | 30.90 | 48.60 | 71.70 | 80.30 |
| 637 | 7.20E+06 | 90.0 | 18.47 | 124.44 | 94.50 | 66.93 | — | — | — | — | — |
| 590 | 4.40E+07 | 88.7 | 32.00 | 332.63 | 99.90 | 11.13 | 81.72 | 3.65 | 79.12 | 18.72 | 9.74 |
| 594 | 3.30E+07 | 79.3 | 36.00 | 302.16 | 100.27 | 34.73 | 73.89 | 10.78 | 72.09 | 34.02 | 19.44 |
| 595 | 6.00E+06 | 67.4 | 10.24 | 23.17 | 18.40 | 0.00 | 19.50 | 33.00 | 97.50 | 7.60 | 0.00 |
| 601 | 7.90E+06 | 88.8 | 6.01 | 79.21 | 89.70 | 26.60 | 46.20 | 38.90 | 55.00 | 46.50 | 52.40 |
| 602 | 1.08E+07 | 72.5 | 27.00 | 357.00 | 98.00 | 0.00 | 20.69 | 0.00 | 33.51 | 33.68 | 11.78 |
| 604 | 6.40E+07 | 76.2 | 36.00 | 45.36 | 99.82 | 35.90 | 45.18 | 22.75 | 25.21 | 45.64 | 39.31 |
| 606 | 1.50E+06 | 65.2 | 11.00 | 95.28 | 100.01 | 85.07 | 92.94 | 93.99 | — | — | — |
| 608 | 7.10E+06 | 7.24 | 30.95 | 308.70 | 99.23 | 70.83 | 88.60 | 45.57 | 52.23 | 55.45 | 62.87 |
| 614 | 5.10E+06 | 68.9 | 6.07 | 17.94 | 98.70 | 43.20 | 67.00 | 0.00 | 82.40 | 71.60 | 58.40 |
| 616 | 1.18E+07 | 87.4 | 25.90 | 253.16 | 99.97 | 0.00 | 63.31 | 0.50 | 61.17 | 10.21 | 7.15 |
| 619 | 7.20E+06 | 82.8 | 15.65 | 208.03 | 99.90 | 31.40 | 40.20 | 5.20 | 9.00 | 50.20 | 61.21 |
| 625 | 6.20E+06 | 87.3 | 41.40 | 221.00 | 99.98 | 15.46 | 27.28 | 23.28 | 34.50 | 27.36 | 14.28 |
| 629 | 1.11E+07 | 94.1 | 36.00 | 148.87 | 99.79 | 44.04 | 73.69 | 25.24 | 76.93 | 50.35 | 33.93 |
| 632 | 1.15E+07 | 93.5 | 22.00 | 371.06 | 99.95 | 5.81 | 33.53 | 0.00 | 3.12 | 9.00 | 19.16 |
| 633 | 650E+06 | 85.5 | 8.68 | 229.99 | 99.70 | 29.00 | 64.00 | 47.20 | 55.20 | 60.30 | 57.90 |
| 635 | 2.00E+06 | 83.3 | 36.00 | 280.90 | — | 18.94 | — | — | — | — | — |

TABLE 5

Associations of Individual BH3 Peptide Profiles with CR

| Metric | Median NR (n = 29) | Median CR (n = 23) | Mann-Whitney p-value | Logistic Reg p-value | AUC |
|---|---|---|---|---|---|
| BAD | 55.3 | 45.9 | 0.090 | 0.084 | 0.647 |
| BID | 37.1 | 22.7 | 0.843 | 0.767 | 0.517 |
| BIM 0.1 | 26.6 | 28.9 | 0.927 | 0.975 | 0.507 |
| BIM 100 | 99.8 | 99.2 | 0.461 | 0.094 | 0.562 |
| NOXA | 20.2 | 17.2 | 0.394 | 0.445 | 0.571 |
| PUMA | 63.7 | 49.6 | 0.229 | 0.156 | 0.600 |
| HRK | 45.6 | 35 | 0.915 | 0.943 | 0.509 |

TABLE 6

Multivariate Analysis of BH3 Peptide Profiling with Other Clinical Variables

| Metric | Median NR (n = 29) | Median CR (n = 23) | Mann-Whitney p-value | Logistic Reg p-value | AUC |
|---|---|---|---|---|---|
| Cytogenetic Risk | — | — | 0.024 | 0.024 | 0.663 |
| MDS Marrow Disorder History | — | — | 0.144 | 0.132 | 0.601 |
| BAD | 55.3 | 45.9 | 0.09 | 0.084 | 0.647 |
| BIM 100 | 99.8 | 99.2 | 0.461 | 0.094 | 0.562 |
| PUMA | 63.7 | 49.6 | 0.229 | 0.156 | 0.6 |
| BAD + BIM 100 + PUMA | — | — | 0.009 | 0.039 | 0.732 |
| BAD + BIM 100 + PUMA + Cytogenetics | — | — | 0.0001 | 0.003 | 0.84 |
| BAD + BIM 100 + PUMA + Cytogenetics + MDS History | — | — | 0.0001 | 0.002 | 0.851 |
| NOXA | 20.2 | 17.2 | 0.394 | 0.445 | 0.571 |
| NOXA + Cytogenetics | — | — | 0.024 | 0.054 | 0.689 |
| NOXA + Cytogenetics + MDS History | — | — | 0.004 | 0.024 | 0.739 |

Next, the BH3 peptides were tested in multivariate analysis with other BH3 peptide profiles and with the clinical variables (Table 7). This analysis reveals that a strongly significant association between BIM 100 μM plus BAD plus PUMA exists in relation to response, with a p-value of 0.009 and a ROC AUC of 0.732 (FIG. 1). When these three peptides are combined with cytogenetic risk category, the p-value becomes 0.0001 with an AUC of 0.84. Further addition of the MDS history to the analysis creates further significance with a p-value of 0.0001 and an AUC of 0.85. Cytogenetic risk category alone only yields an AUC value of 0.60 (Cytogenetic risk plus MDS history gives an AUC of 0.72). This indicates that addition of the BH3 peptide priming to the analysis greatly increases the ability to identify those patients who respond to alvocidib (e.g., FLAM). At an ideal cutoff (Youden index) using the BH3 peptide data along with cytogenetic risk category and MDS history, this assay is 89.5% sensitive and 76% specific at identifying patients who responded to treatment in this study. This indicates that using the BH3 peptide priming data from these three peptides along with clinical information could be valuable in predictive value for treatment with alvocidib.

TABLE 7

Associations of Individual BH3 Peptide Profiles with CR and Bone Marrow Samples

| Metric | Median NR (n = 29) | Median CR (n = 23) | Mann-Whitney p-value | Logistic Reg p-value | AUC |
|---|---|---|---|---|---|
| BAD | 49.4 | 45.4 | 0.719 | 0.695 | 0.544 |
| BID | 19.4 | 16.8 | 0.917 | 0.368 | 0.512 |
| BIM 0.1 | 17.2 | 19.9 | 0.535 | 0.430 | 0.566 |
| BIM 100 | 99.9 | 98.6 | 0.067 | 0.012 | 0.709 |
| NOXA | 5.2 | 44.5 | 0.006 | 0.0007 | 0.805 |
| PUMA | 50.9 | 33.8 | 0.339 | 0.275 | 0.610 |
| HRK | 27.4 | 30.9 | 0.714 | 0.461 | 0.542 |

Figures 2C, 2D:
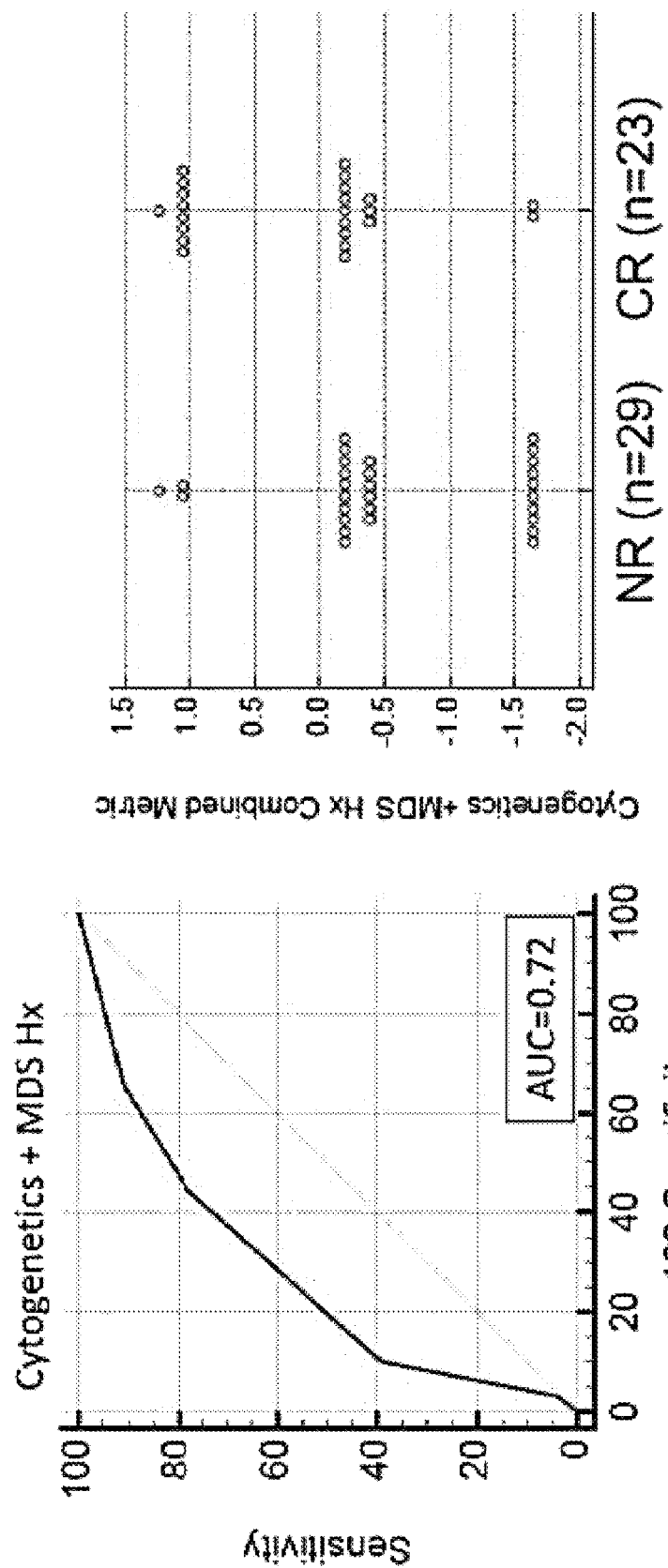
Figures 2E, 2F:
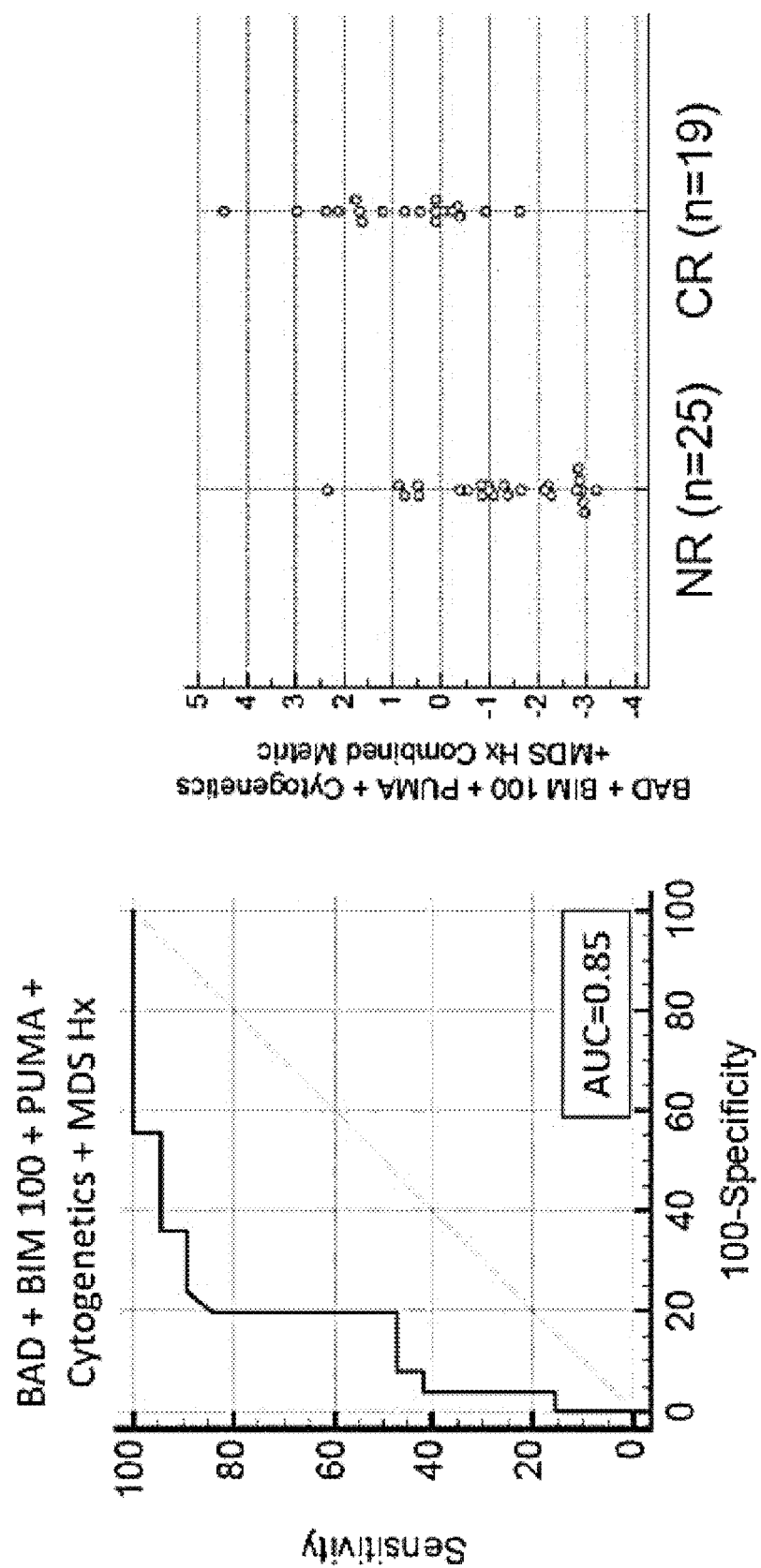
Figures 3A, 3B, 3C:
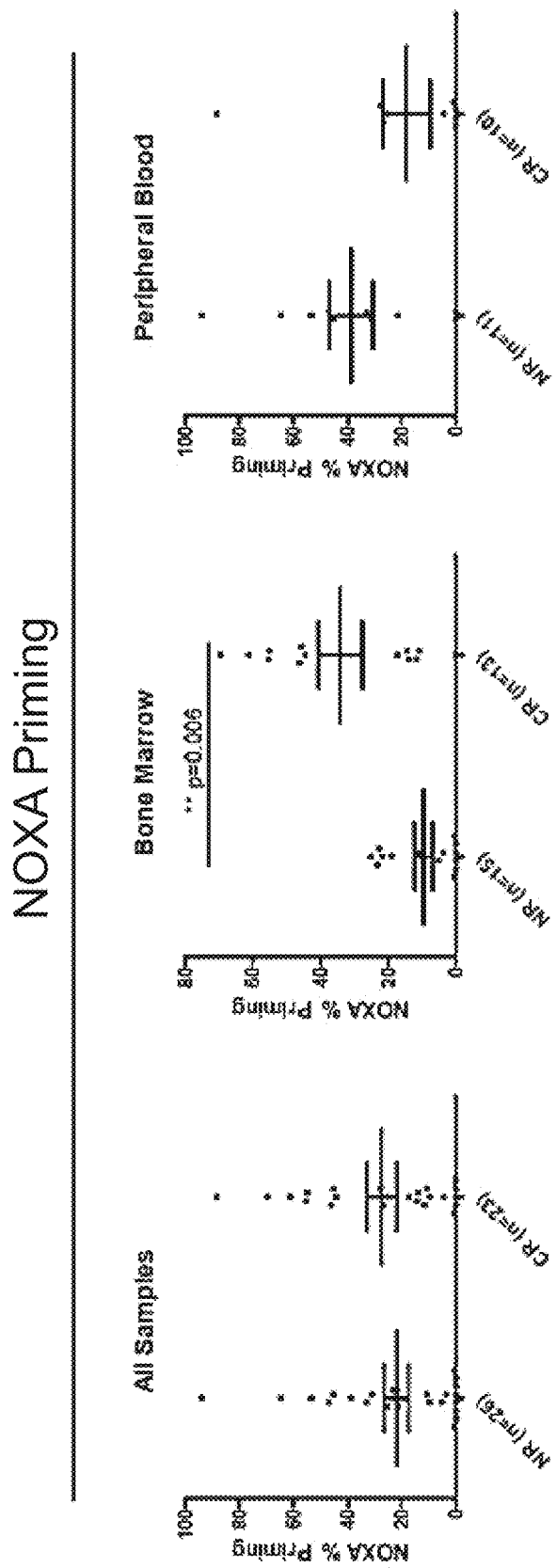
FIGS. 3A-C show Noxa BH3 Peptide Association by Dot blot correlation analysis with Response in bone marrow-derived FLAM treated patient specimens. NOXA priming alone shows predictive value in bone marrow samples. Panels A-C show dot plots representing NOXA priming measured in all samples (A), and those taken from the bone marrow (B) or the peripheral blood (C). Samples obtained from the bone marrow show a significant associate with CR, which is not seen in samples taken from the peripheral blood.
Figures 4C, 4D:
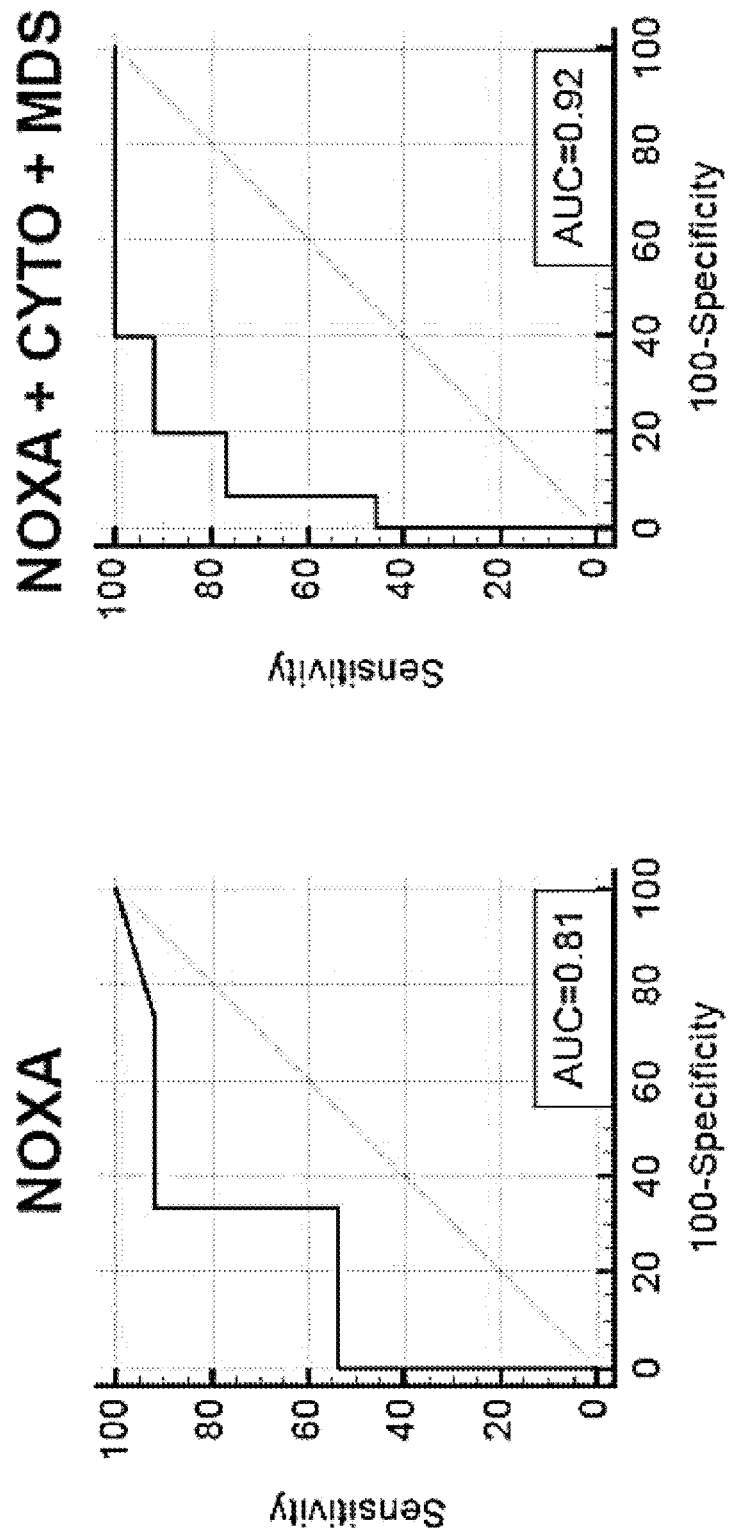

During the course of this study, we also examined other factors that may play a role in BH3 priming. Since the source of leukemic cells (i.e. peripheral blood or bone marrow) could potentially isolate different populations of cells, we performed analysis in only those samples that were obtained from the bone marrow of the patients. Table 8 shows the association of each BH3 peptide with response in only bone marrow samples. In this sample subset, NOXA priming is significantly (p=0.006) higher in patients that respond to treatment compared with those that did not (44.5% and 5.2% respectively) and has an AUC value of 0.805 (FIG. 2 and FIG. 3). None of the other single peptides showed significant association with response in the bone marrow samples alone. With a cutoff value of higher than 10.78% NOXA priming, the test is 92% sensitive and 67% specific. NOXA priming of 15% or more appears to be associated with a high likelihood of response to alvocidib treatment (e.g., FLAM), while NOXA priming of about 30% or more is predictive of a near 100% response to alvocidib-containing regimens. Addition of cytogenetic risk factor and MDS history to the algorithm shows that NOXA priming adds to these variables in predicting response to treatment, and yields an AUC value of 0.92 with a sensitivity of 92% and specificity of 80% at an ideal cutoff value (Table 8 and FIG. 3).

TABLE 8

Statistical analyses of BH3 peptides were performed in only those samples that were obtained from bone marrow

| Metric | Median NR (n = 29) | Median CR (n = 23) | Mann-Whitney p-value | Logistic Reg p-value | AUC |
|---|---|---|---|---|---|
| BAD | 49.4 | 45.4 | 0.710 | 0.695 | 0.544 |
| BIM 100 | 99.9 | 98.6 | 0.067 | 0.012 | 0.709 |
| PUMA | 50.9 | 33.8 | 0.339 | 0.275 | 0.61 |
| BAD + BIM 100 + PUMA | — | — | 0.008 | 0.0058 | 0.813 |
| BAD + BIM 100 + PUMA + Cytogenetics | — | — | 0.0007 | 0.0051 | 0.887 |
| BAD + BIM 100 + PUMA + Cytogenetics + MDS History | — | — | 0.001 | 0.0069 | 0.893 |
| NOXA | 5.2 | 44.5 | 0.006 | 0.0007 | 0.805 |
| NOXA + Cytogenetics | — | — | 0.0008 | 0.0015 | 0.874 |
| NOXA + Cytogenetics + MDS History | — | — | 0.0002 | 0.0002 | 0.918 |

The results of this study indicate that BH3 profiling may prove useful in identifying patients that are likely to respond to alvocidib treatment, such as the FLAM treatment. Looking at the entire dataset, while individual BH3 peptides did not correlate with response, combinations of several peptides (BIM, BAD, and PUMA) did show strong correlations with alvocidib response. These several peptides showed correlations with response in both the bone marrow and peripheral blood samples within the study. It is encouraging that these data were additive to known patient risk factors to identify an algorithm incorporating the cytogenetic status along with the MDS history of the patient into a single metric that predicts the patient response.

Another interesting finding of this study is that while NOXA signaling was not found to be significantly associated with FLAM response in the entire dataset, examination of the bone marrow samples alone showed very strong associations with response. As the niche of AML tumor cells would be the bone marrow, it is not surprising that there would be different BH3 profiles in the peripheral blood compared with the bone marrow, as phenotypic markers of blasts can be different in the peripheral blood compared with the bone marrow (1,2). Additionally, bone marrow stroma has previously been shown to confer resistance to AML cells to various therapies through direct cell contact and through soluble factors present in the bone marrow (3). Since the bone marrow draw would potentially collect AML blasts, soluble factors, and potentially the actual stromal cells, the BH3 priming assay in bone marrow may represent a more direct test of the leukemic cells in their normal environmental context. Functional differences have previously been observed in AML with FLT3 kinase inhibitor monotherapy, where circulating blasts are cleared from the peripheral blood by the therapy while bone marrow blasts are minimally affected (4). The NOXA readout may be detecting a similar functional difference, where priming with NOXA results in Mcl-1 displacement and leads to apoptosis to identify those cancers that are likely to respond to FLAM.

Both of the algorithms identified in this study, NOXA and [BAD+BIM 100+PUMA] priming, may be identifying cancer cells that are Mcl-1 primed. A cell yielding a high apoptotic response to NOXA is said to be Mcl-1 primed, while a high response to the peptide Bad indicates that Bcl-xL or Bcl-2 provides the apoptotic block. Since PUMA may reflect pan-Bcl-2 family priming, and the algorithm behind [BAD+BIM 100+PUMA] is actually PUMA−BAD−BIM100, so in effect; both of these readings may be effectively measuring the priming state of Mcl-1, and ultimately those patients that respond to alvocidib treatment, such as the FLAM regimen may be Mcl-1 dependent. Accordingly, MCL-1 overexpression in patient cancer cells is believed to be associated with a high likelihood of response to alvocidib.

Example 2

Algorithm to Discern Between a FLAM Regimen Versus a Traditional 7+3 Treatment Strategy BIM 0.1 priming in AML patient bone marrow or peripheral blood was correlated with response to the 7+3 regimen (cytarabine plus anthracycline); See Pierceall, et al. "BH3 Profiling Discriminates Response to Cytarabine-based Treatment of Acute Myelogenous Leukemia" Molecular Cancer Therapeutics. As discussed above, NOXA bone marrow priming is correlated with response to the FLAM (alvocidib, ara-C, mitoxantrone) regimen. We investigated what algorithm would distinguish between whether FLAM or 7+3 should be used to treat naive AML patients.

BIM 0.1 is predictive of response to 7+3 in a BM sample subset with an AUC value of 0.80 and sensitivity and specificity of 64.3% and 100% respectively—below left. However, in those same samples NOXA has essentially no predictive power with an AUC value of 0.54 and sensitivity and specificity of 42.9% and 100% specificity. See FIG. 5. (compared with an AUC of 0.81 and 92%/67% sensitivity/specificity when treated with FLAM). This indicates that NOXA priming, when detected in bone marrow cells taken from pretreatment AML patients, is correlated with response to FLAM and not 7+3, and that the BIM 0.1 reading from the peripheral blood of AML patients tested prior to treatment is correlated with response to 7+3 and not FLAM.

Figure 6:
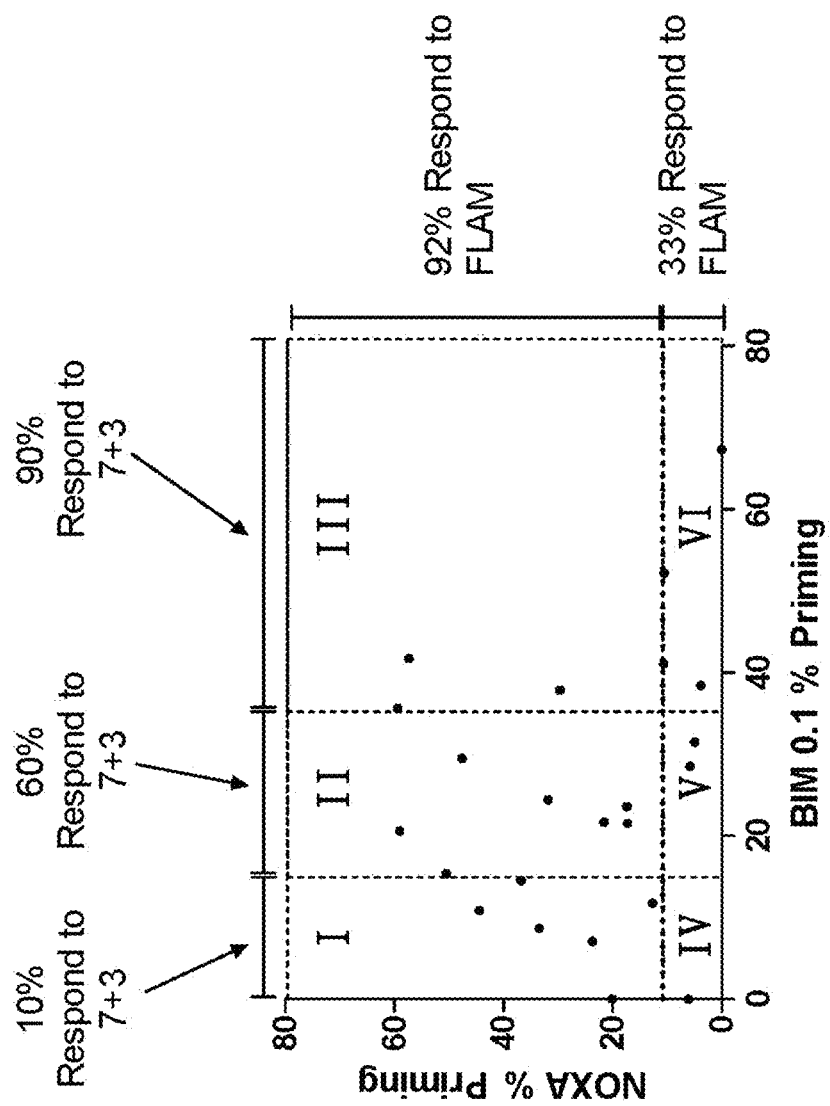
FIG. 6 shows a method for identifying an algorithm for selecting between cancer therapies in a treatment-naïve AML patient. By comparing the relative IM 0.1 and NOXA profiling, the patient can be assigned to FLAM therapy, 7+3 therapy or is identified as not suitable for either therapy.

Further examination of the NOXA priming compared with the BIM 0.1 priming reveals that there are subclasses of patients with priming values that would indicate that they are unlikely to respond one agent but likely to respond to another. FIG. 6 illustrates the NOXA priming versus the BIM 0.1 priming from bone marrow samples from the original 7+3 study (n=23). The data in FIG. 6 provide a method of selecting between cancer therapy strategies in a pre-treatment AML patient by comparing NOXA priming in a bone marrow sample versus BIM 0.1 priming in a peripheral blood (PB) sample of the patient. If the BM NOXA>10.8% and BM/PB BIM 0.1<35% then the patient is a candidate for FLAM. If the BM NOXA is <10.8% and BM/PB BIM 0.1>15% then patient is a candidate for 7+3 therapy. The patient is also a candidate for 7+3 therapy where BM NOXA<10.8% and BM/PB BIM 0.1>35%. Finally, where BM NOXA<10.8% and BM/PB BIM 0.1<15% the patient is not a candidate for either FLAM or 7+3 therapy Example 3

Figures 7A, 7B:
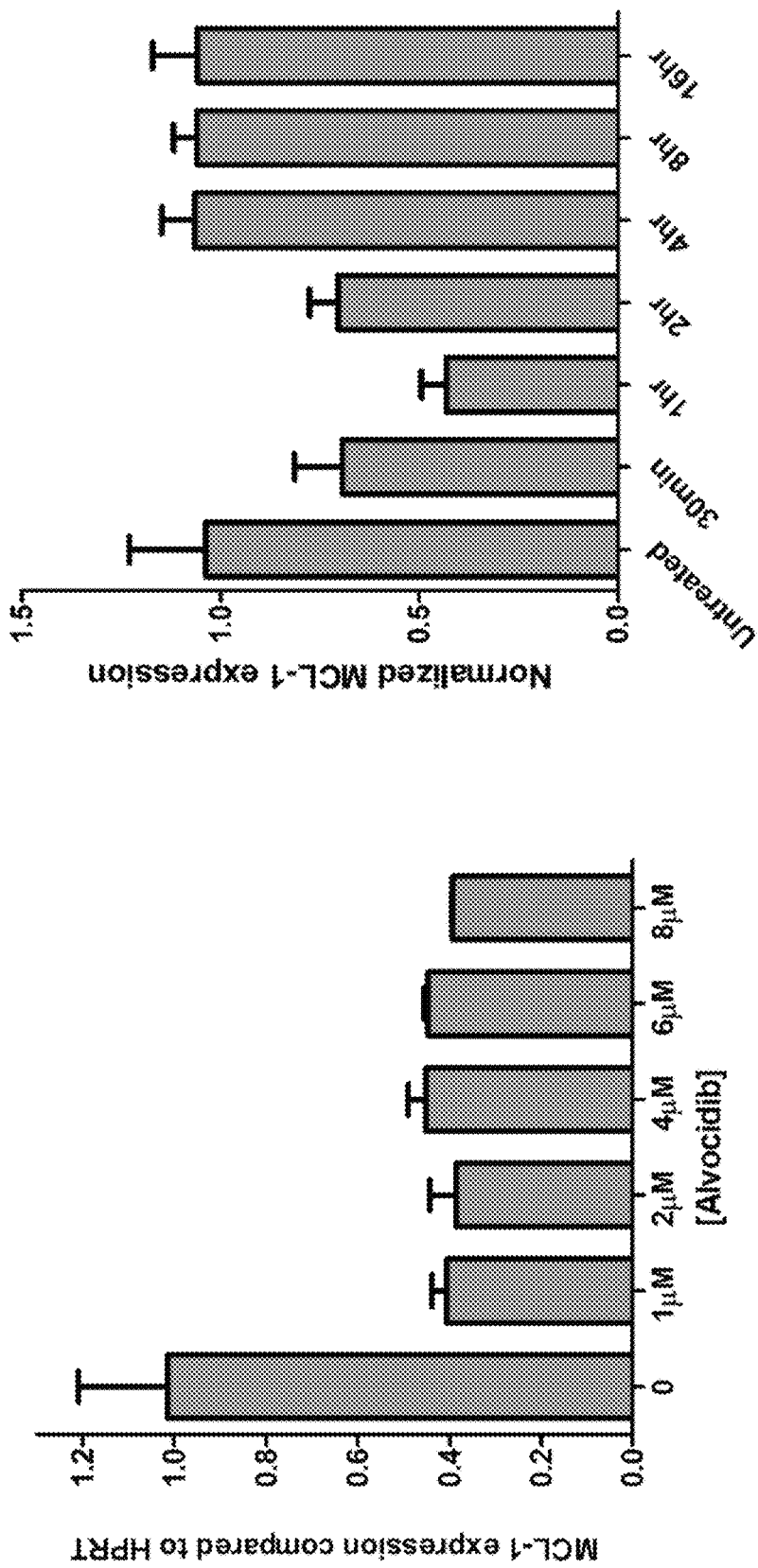
FIGS. 7A-B provides data showing alvocidib suppresses oncogenic mRNA in a dose and time dependent manner for MV-4-11 cells.

Alvocidib Lowers MCL-1 mRNA Expression in MV-411 Cells in a Time and Dose Dependent Manner An AML cell line, MV-4-11, expresses MCL-1. MCL-1 is a key anti-apoptotic protein in MV-4-11 cells. Alvocidib, a CDK9 inhibitor, lowers the expression of MCL-1 mRNA, which is already well documented in the literature. Alvocidib down-regulates MCL-1 mRNA in MV-4-11 cells in a dose dependent manner (FIG. 7A). The dose dependence is observed by monitoring the relative expression of MCL-1 mRNA compared to controls when cells are dosed with alvocidib at concentrations of 0-8 μM MV-4-11 cells were treated with alvocidib for 2 hrs in vitro. Following treatment, cells were harvested and prepared using a standard real time PCR (RT-PCR) assay for detection of MCL-1 mRNA to probe for changes relative to controls.

In addition, alvocidib also down-regulates MCL-1 mRNA in MV-4-11 in a time-dependent manner (FIG. 7B). The time dependence is observed by monitoring the relative expression of MCL-1 mRNA compared controls over time. The relative expression of MCL-1 mRNA was measured at 0.5-16 hour time points after dosing with 100 nM of alvocidib.

MV-4-11 cells were treated with 100 nM alvocidib in vitro for the times indicated in FIG. 7B. Following treatment, cells were harvested and prepared using standard RT-PCR assay for detection of MCL-1 mRNA expression. Alvocidib reduced MCL-1 mRNA expression as early as 30 minutes post-treatment. The relative expression of MCL-1 mRNA shows that alvocidib lowers the expression of MCL-1 mRNA in MV-4-11 cells.

Example 4

Figure 8:
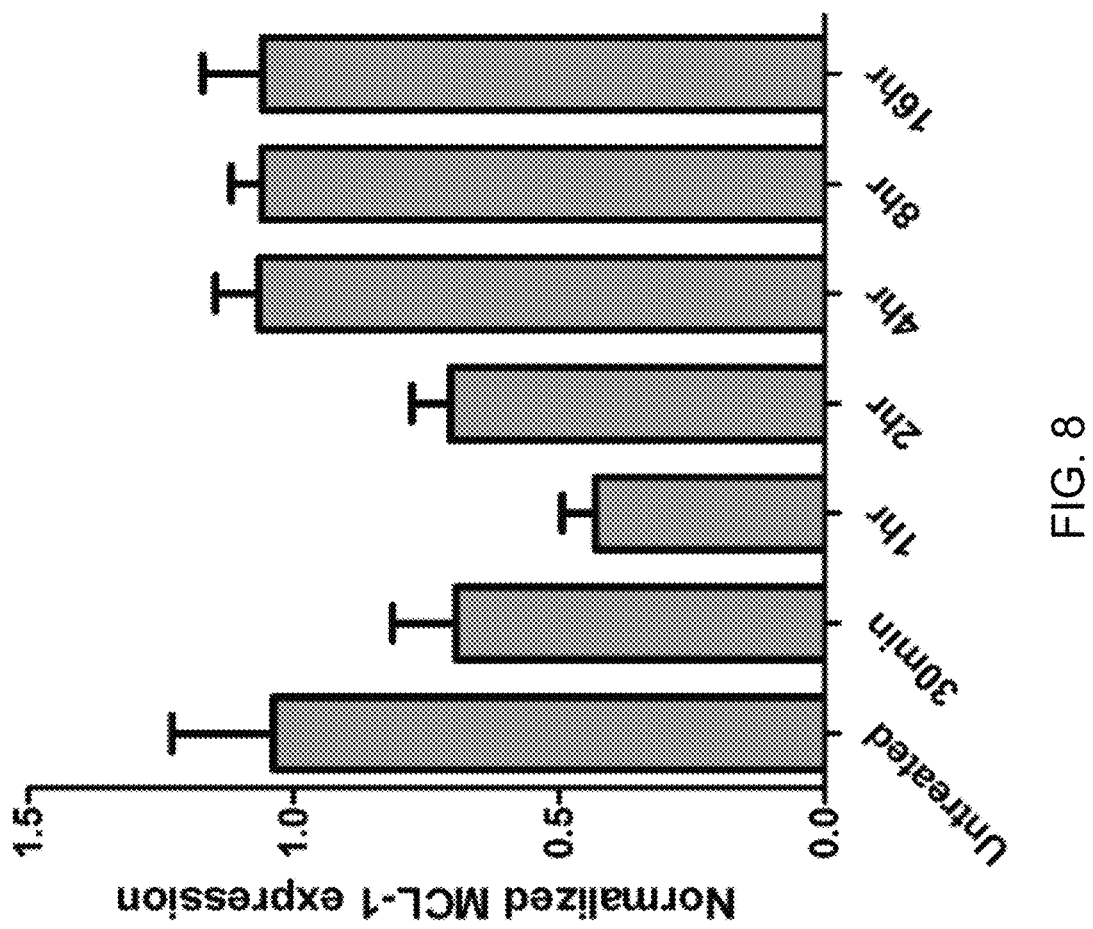
FIG. 8 is data showing alvocidib suppresses oncogenic mRNA in a dose dependent manner for A549 cells.

Alvocidib Lowers MCL-1 mRNA Expression in A549 Cells in a Dose Dependent Manner and Oncogenic Protein Expression in a Time Dependent Manner The A549 cell line is a human adenocarcinoma cell line, which expresses MCL-1. Alvocidib down-regulates MCL-1 mRNA in A549 cells in a dose dependent manner (FIG. 8). The dose dependence is observed by monitoring the relative expression of MCL-1 mRNA compared to controls when cells are dosed with alvocidib at concentrations of 0-8 μM. A549 cells were treated with alvocidib for 2 hrs in vitro. Following treatment, cells were harvested and prepared using a standard RT-PCR assay for detection of MCL-1 mRNA to probe for changes relative to controls.

Figure 9A:
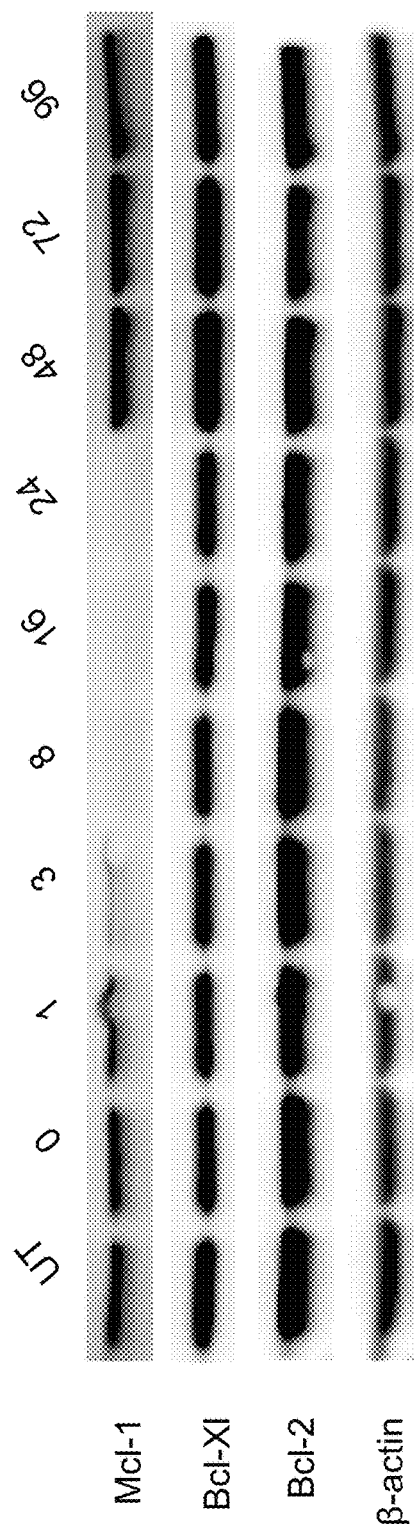
FIGS. 9A-B are gels showing alvocidib suppresses expression of MCL-1 in a time dependent manner with a wash step (FIG. 9A), and without a wash step (FIG. 9B).
Figure 9B:
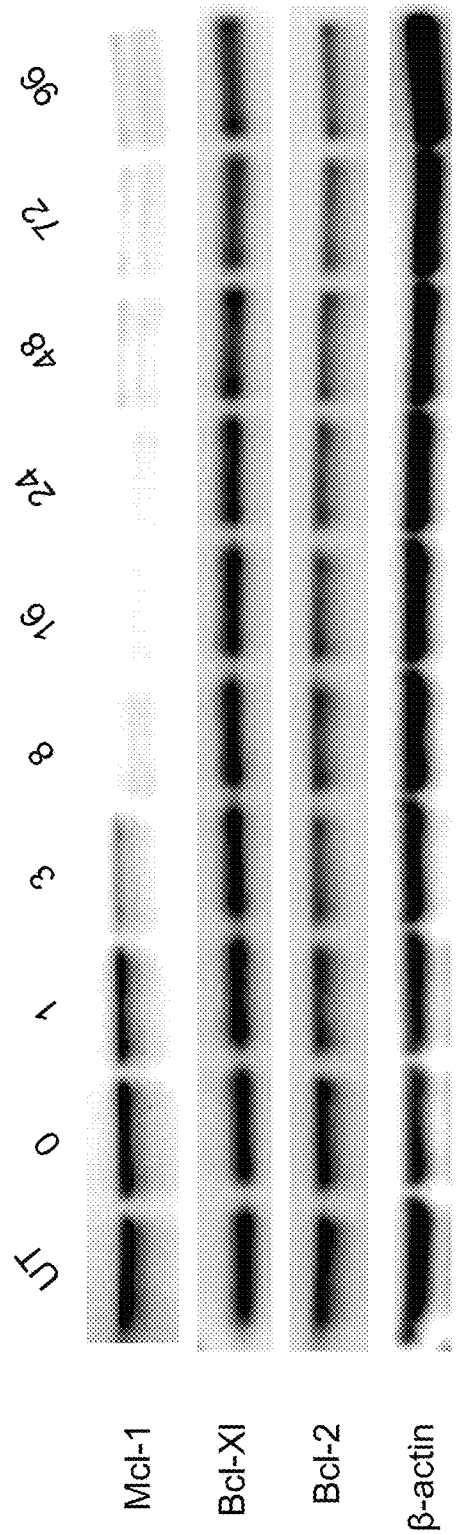

In addition, alvocidib also down-regulates MCL-1 in A549 in a time-dependent manner (FIG. 9A-B). The time dependence is observed by monitoring the relative expression of MCL-1, Bcl-xL, and Bcl-2 compared β-actin over time. The relative expression of MCL-1, Bcl-xL, and Bcl-2 was measured at 0-96 hour time points after dosing with 350 nM of alvocidib. In one group, after 24 hours of treatment, media was removed and replaced with fresh media containing 350 nM alvocidib (i.e., a wash step; see FIG. 9A).

A549 cells were treated with 350 nM alvocidib in vitro for the times indicated in FIG. 9A-B. Following treatment (and wash step as applicable), cells were harvested and prepared using standard immunoblotting techniques for detection of MCL-1, Bcl-xL, and Bcl-2 expression. The relative expression of MCL-1, Bcl-xL, and Bcl-2 compared to β-actin shows that alvocidib lowers the expression of oncogenic protein in A549 cells.

Example 5

Figure 10A:
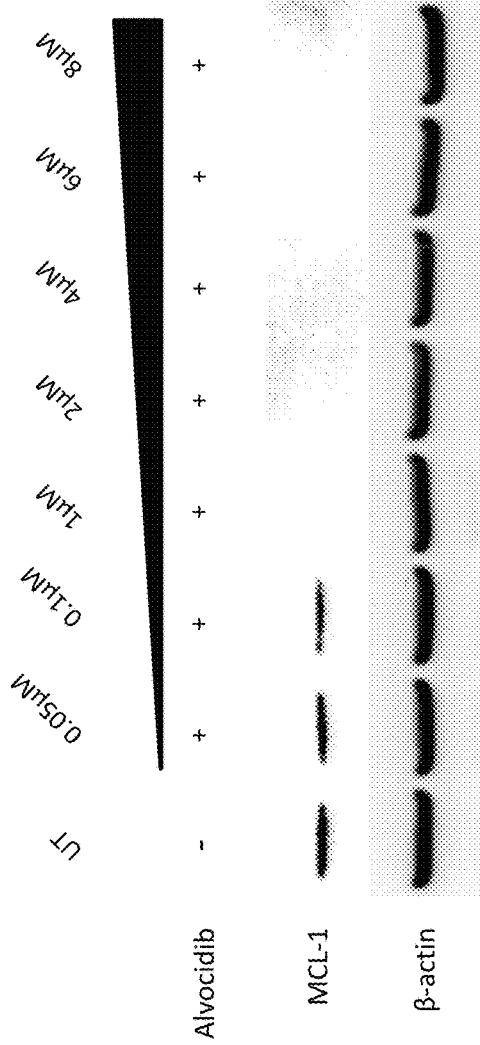
FIGS. 10A-B are additional gels showing alvocidib suppresses key oncogenic proteins in a dose and time dependent manner for MV-4-11 cells.

Alvocidib Lowers Oncogenic Protein Expression in MV-4-11 Cells in a Time and Dose Dependent Manner Alvocidib down-regulates MCL-1 in MV-4-11 cells in a dose dependent manner (FIG. 10A). The dose dependence is observed by monitoring the relative expression of MCL-1 compared to β-actin when cells are dosed with alvocidib at concentrations of 0-8 μM. MV4-11 cells were treated with alvocidib for 2 hrs in vitro. Following treatment, cells were harvested and prepared using standard immunoblotting techniques for detection of MCL-1 to probe for changes relative to β-actin.

Figure 10B:
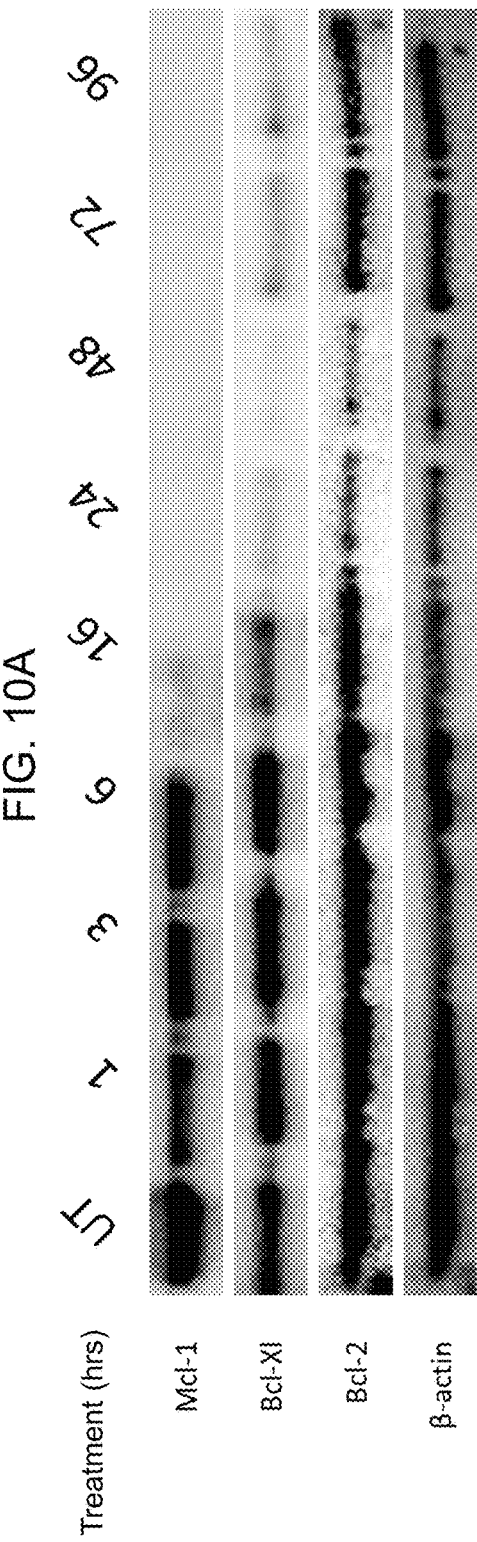

In addition, alvocidib also down-regulates MCL-1 in MV-4-11 in a time-dependent manner (FIG. 10B). The time dependence is observed by monitoring the relative expression of MCL-1, Bcl-xL, and Bcl-2 compared β-actin over time. The relative expression of MCL-1, Bcl-xL, and Bcl-2 was measured at 1-96 hour time points after dosing with 80 nM of alvocidib.

MV4-11 cells were treated with 80 nM alvocidib in vitro for the times indicated in FIG. 10B. Following treatment, cells were harvested and prepared using standard immunoblotting techniques for detection of MCL-1, Bcl-xL, and Bcl-2 expression. The relative expression of MCL-1, Bcl-xL, and Bcl-2 compared to μ-actin shows that alvocidib lowers the expression of oncogenic protein in MV-4-11 cells.

Example 6

Alvocidib Lowers N-Myc Expression in SK-N-AS Cells in a Time Dependent Manner

Figure 11:
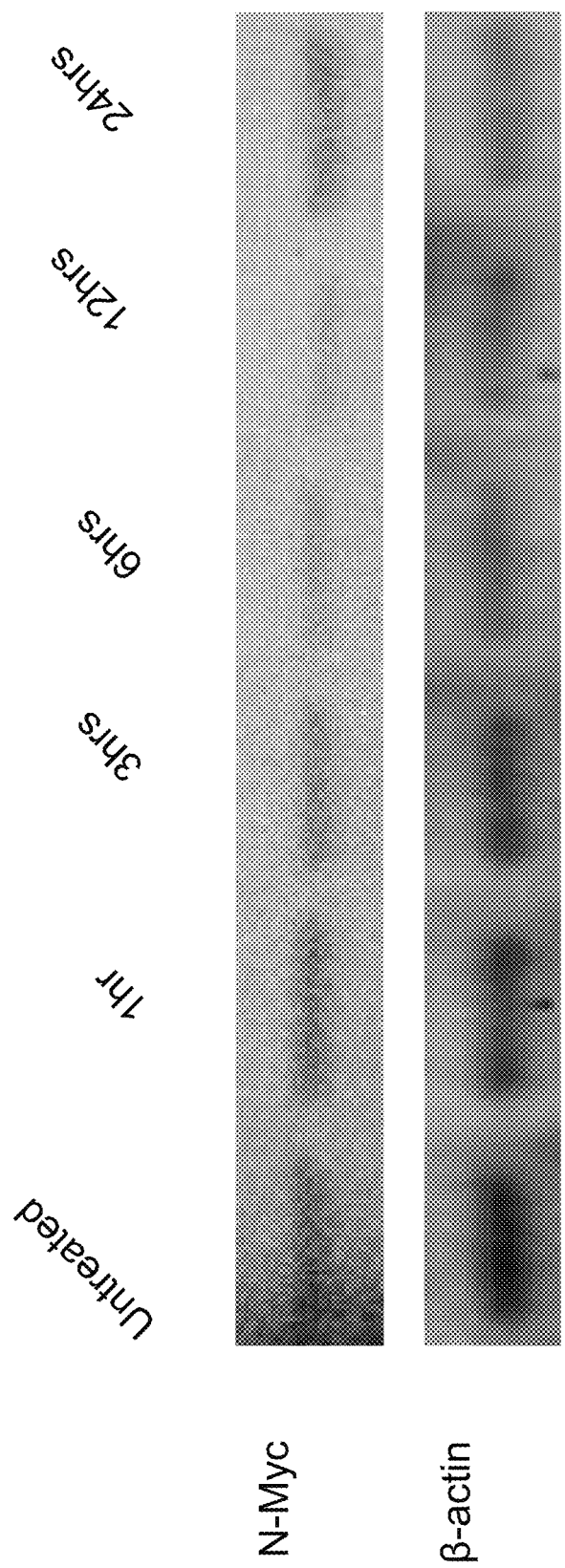
FIG. 11 illustrates alvocidib suppresses expression of N-Myc in a time dependent manner for SK-N-AS cells (solid tumor, neuroblastoma).

The SK-N-AS cell line is a human neuroblastoma cell line that expresses N-Myc, which is a key oncogenic protein. Alvocidib down-regulates N-Myc in SK-N-AS cells in a time-dependent manner (FIG. 11). The time dependence is observed by monitoring the relative expression of N-Myc compared β-actin over time. The relative expression of N-Myc was measured at 1-24 hour time points after dosing with 300 nM of alvocidib.

SK-N-AS cells were treated with 300 nM alvocidib in vitro for the times indicated in FIG. 11. Following treatment, cells were harvested and prepared using standard immunoblotting techniques for detection of N-Myc expression. The relative expression of N-Myc shows that alvocidib lowers the expression of N-Myc in SK-N-AS cells.

Example 7

Figure 12:
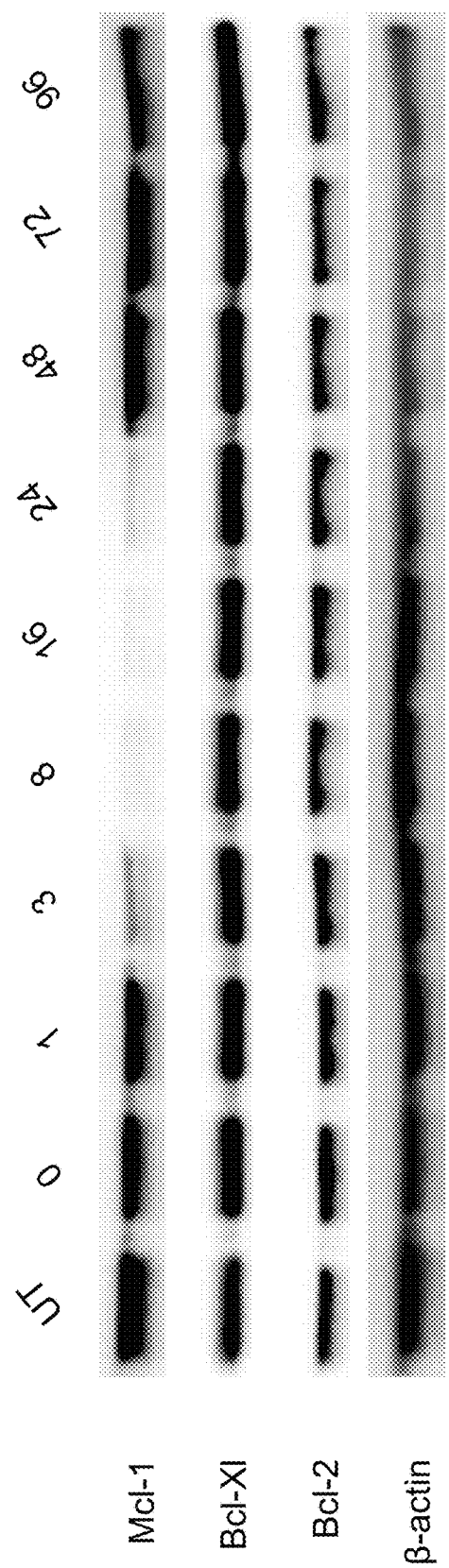
FIG. 12 shows alvocidib suppresses expression of oncogenic proteins in a time dependent manner when using a repeat-dosing regimen for A549 cells.

Alvocidib Lowers MCL-1 Expression in A549 Cells in a Time Dependent Manner Using a Repeat-Dosing Regimen Alvocidib down-regulates MCL-1 in A549 cells in a time-dependent manner (FIG. 12). The time dependence is observed by monitoring the relative expression of MCL-1, Bcl-xL, and Bcl-2 compared β-actin over time. The relative expression of MCL-1, Bcl-xL, and Bcl-2 was measured at 0-96 hour time points after dosing with 350 nM of alvocidib.

Cells were treated 3 times (three 24 hour periods, broken by two 24 hour breaks) with 350 nM alvocidib in vitro. Following treatment, cells were harvested and prepared using standard immunoblotting techniques for detection of MCL-1, Bcl-xL, and Bcl-2 expression. The relative expression of MCL-1, Bcl-xL, and Bcl-2 compared to β-actin shows that alvocidib lowers the expression of oncogenic protein in A549 cells.

Example 8

Alvocidib Lowers Oncogenic Protein Expression in Panc-1 Cells in a Time Dependent Manner The Panc-1 cell line is a human pancreatic carcinoma cell line that expresses MCL-1. Alvocidib down-regulates MCL-1 in Panc-1 cells in a time dependent manner. The time dependence is observed by monitoring the relative expression of MCL-1, Bcl-xL, and Bcl-2 compared β-actin over time. The relative expression of MCL-1, Bcl-xL, and Bcl-2 was measured at 0-96 hour time points after dosing with 730 nM of alvocidib. In one group, after 24 hours of treatment, media was removed and replaced with fresh media containing 730 nM alvocidib (i.e., a wash step; see FIG. 13A).

Panc-1 cells were treated with 730 nM alvocidib in vitro for the times indicated in FIG. 13A-B. Following treatment (and wash step as applicable), cells were harvested and prepared using standard immunoblotting techniques for detection of MCL-1, Bcl-xL, and Bcl-2 expression. The relative expression of MCL-1, Bcl-xL, and Bcl-2 compared to β-actin shows that alvocidib lowers the expression of oncogenic protein in Panc-1 cells.

Example 9

Figure 14:
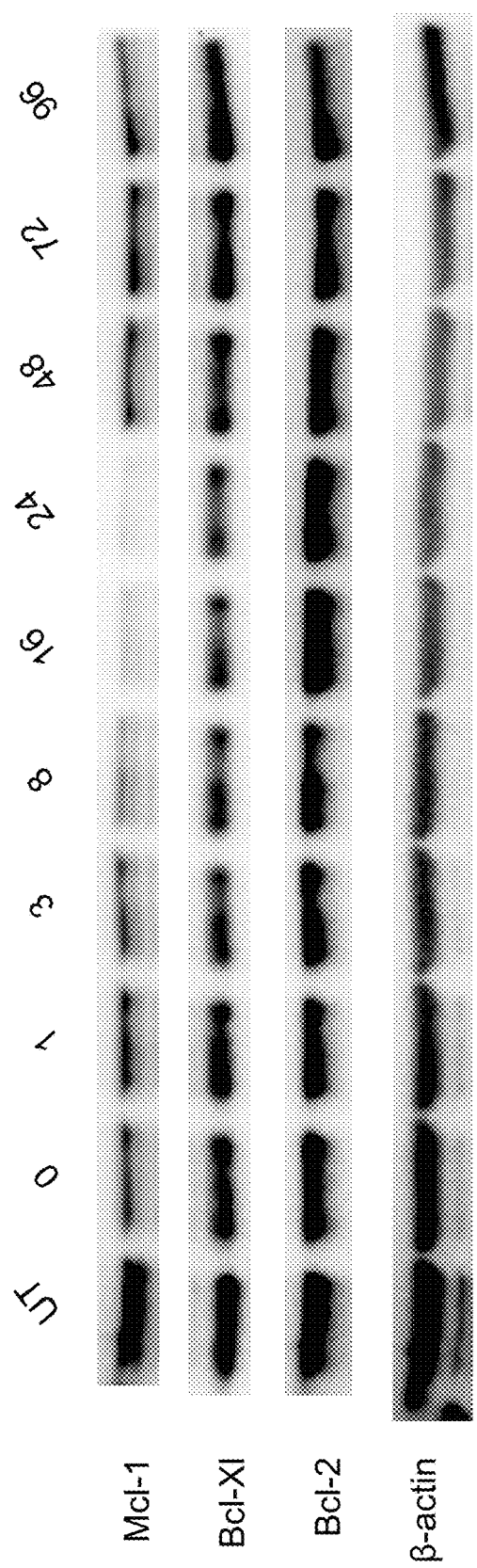
FIG. 14 show alvocidib suppresses expression of oncogenic proteins in a time dependent manner when using a repeat-dosing regimen for Panc-1 cells.

Alvocidib Lowers Oncogene Protein Expression in Panc-1 Cells in a Time Dependent Manner Using a Repeat-Dosing Regimen Alvocidib down-regulates MCL-1 in Panc-1 cells in a time-dependent manner (FIG. 14) when a repeat dosing regimen is used. The time dependence is observed by monitoring the relative expression of MCL-1, Bcl-xL, and Bcl-2 compared β-actin over time. The relative expression of MCL-1, Bcl-xL, and Bcl-2 was measured at 0-96 hour time points after dosing with 730 nM of alvocidib.

Cells were treated 3 times (three 24 hour periods, broken by two 24 hour breaks) with 730 nM alvocidib in vitro. Following treatment, cells were harvested and prepared using standard immunoblotting techniques for detection of MCL-1, Bcl-xL, and Bcl-2 expression. The relative expression of MCL-1, Bcl-xL, and Bcl-2 compared to β-actin shows that alvocidib lowers the expression of oncogenic proteins in Panc-1 cells.

Example 10

Alvocidib Lowers Oncogenic Protein Expression in Yugen8 Cells in a Time Dependent Manner The Yugen8 cell line is a skin carcinoma cell line that expresses MCL-1. Alvocidib down-regulates MCL-1 in Yugen8 cells in a time dependent manner. The time dependence is observed by monitoring the relative expression of MCL-1, Bcl-xL, and Bcl-2 compared β-actin over time. The relative expression of MCL-1, Bcl-xL, and Bcl-2 was measured at 0-96 hour time points after dosing with 280 nM of alvocidib. In one group, after 24 hours of treatment, media was removed and replaced with fresh media containing 280 nM alvocidib (i.e., a wash step; see FIG. 15A).

Yugen8 cells were treated with 280 nM alvocidib in vitro for the times indicated in FIG. 15A-B. Following treatment (and wash step as applicable), cells were harvested and prepared using standard immunoblotting techniques for detection of MCL-1, Bcl-xL, and Bcl-2 expression. The relative expression of MCL-1, Bcl-xL, and Bcl-2 compared to β-actin shows that alvocidib lowers the expression of oncogenic protein in Yugen8 cells.

Example 11

Figure 16:
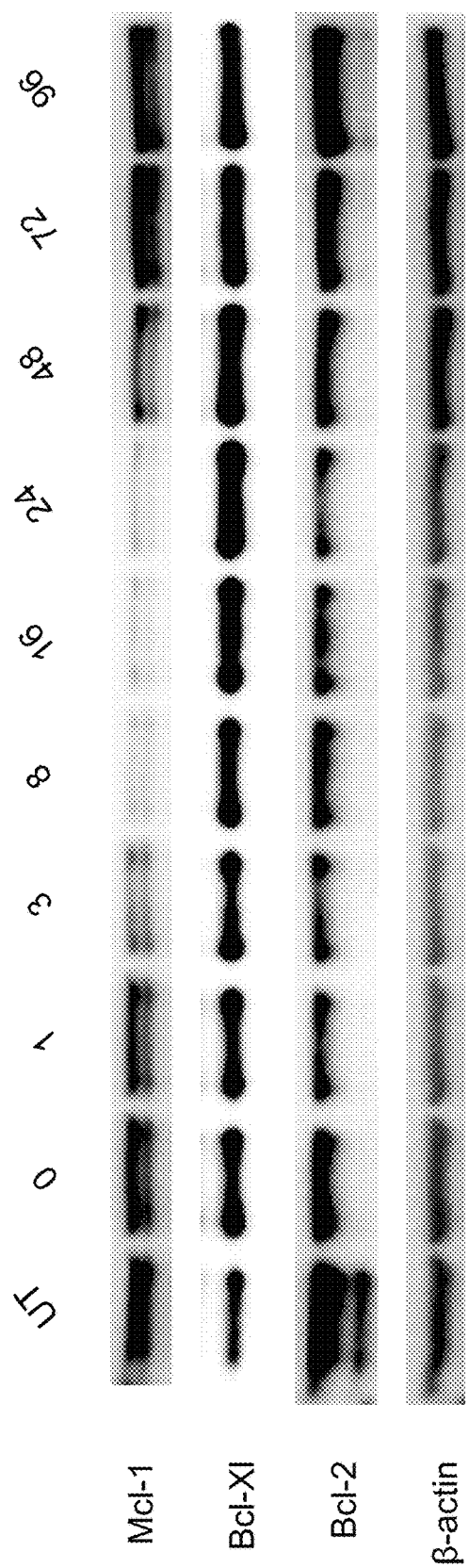
FIG. 16 shows alvocidib suppresses expression of oncogenic proteins in a time dependent manner when using a repeat-dosing regimen for Yugen8 cells.

Alvocidib Lowers Oncogenic Protein Expression in Yugen8 Cells in a Time Dependent Manner Using a Repeat Dosing Regimen Alvocidib down-regulates MCL-1 in Yugen8 in a time-dependent manner (FIG. 16) when a repeat dosing regimen is used. The time dependence is observed by monitoring the relative expression of MCL-1, Bcl-xL, and Bcl-2 compared β-actin over time. The relative expression of MCL-1, Bcl-xL, and Bcl-2 was measured at 0-96 hour time points after dosing with 280 nM of alvocidib.

Cells were treated 3 times (three 24 hour periods, broken by two 24 hour breaks) with 280 nM alvocidib in vitro. Following treatment, cells were harvested and prepared using standard immunoblotting techniques for detection of MCL-1, Bcl-xL, and Bcl-2 expression. The relative expression of MCL-1, Bcl-xL, and Bcl-2 compared to β-actin shows that alvocidib lowers the expression of oncogenic proteins in Yugen8 cells.

Example 12

Alvocidib Represses MCL-1 Expression in the ACM (or FLAM) Combination

Figure 17A:
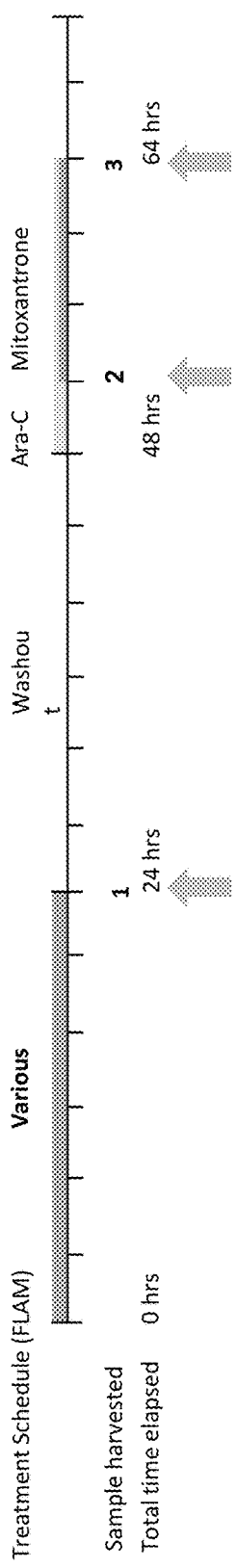
FIGS. 17A-B show alvocidib represses MCL-1 when used in an ACM (or FLAM) combination. The treatment schedule (FIG. 17A) as well as the results from the immunoblotting (FIG. 17B) are provided.

Alvocidib represses super enhancer complex regulated genes, including expression of MCL-1, over the course of the ACM (or FLAM) regimen, as modeled in vitro (FIG. 17A).

Figure 17B:
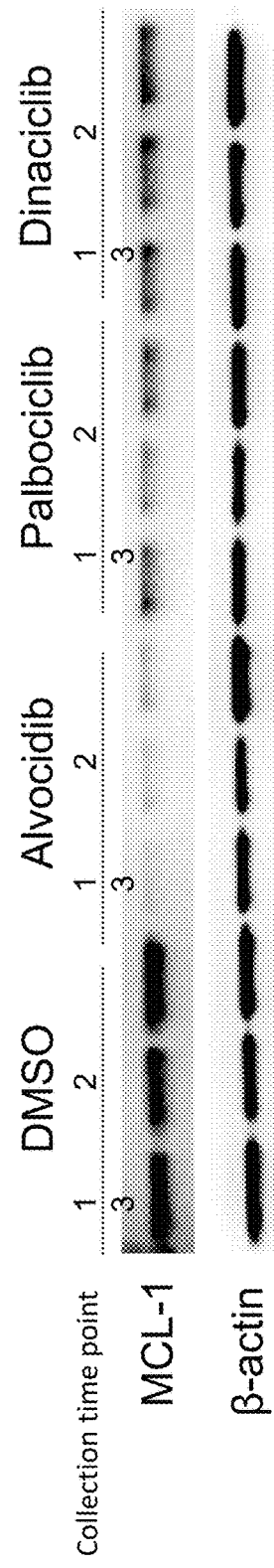

MV-4-11 cells were treated with 80 nM alvocidib, 1 μM palbociclib, or 50 nM dinaciclib in vitro. Each treatment was dosed at the respective 24 hour EC 50 as shown in FIG. 17A. Following the treatment, cells were harvested and prepared using standard immunoblotting techniques for detection of MCL-1. The relative expression of MCL-1 compared to β-actin shows how the different treatments lower the expression of MCL-1 in MV-4-11 cells (FIG. 17B).

Those skilled in the art will recognize, or be able to ascertain, using no more than routine experimentation, numerous equivalents to the specific embodiments described specifically herein. Such equivalents are intended to be encompassed in the scope of certain embodiments.

REFERENCES

1 Rezaei, A., et al. "Leukemia Markers Expression of Peripheral Blood Vs Bone Marrow Blasts Using Flow Cytometry." *Med Sci Monn.* 9.8 (2003): 359-362.2.

2 Almarzooqi, S., et al. "Comparison of Peripheral Blood versus Bone Marrow Blasts Immunophenotype in Pediatric Acute Leukemias." *Ibnosina J Med BS* 195-204.

3 Zeng, Z., et al. "Targeting the Leukemia Microenvironment by CXCR4 Inhibition Overcomes Resistance to Kinase Inhibitors and Chemotherapy in AML." *Blood* 113.24 (2009): 6215-6224.

4 Yang, X. "Bone Marrow Stroma-mediated Resistance to FLT3 Inhibitors in FLT3-ITD AML Is Mediated by Persistent Activation of Extracellular Regulated Kinase." *Br J Haematol* 164.1 (2014): 61-72.

All of the U.S. patents, U.S. patent application publications, U.S. patent applications, foreign patents, foreign patent applications and non-patent publications referred to in this specification or the attached Application Data Sheet are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating a mammal with acute myeloid leukemia (AML) whose disease is dependent on MCL-1 comprising administering alvocidib, cytarabine, and mitoxantrone to the mammal with bone marrow cells having MCL-1 priming of at least 40% determined by subjecting cells from the mammal's bone marrow to a BH3 mimetic that is selective for MCL-1 and determining the percentage change in the mitochondrial polarization which corresponds to the MCL-1 priming.

2. The method of claim 1 wherein the determination of MCL-1 priming includes permeabilizing the bone marrow cells.

3. The method of claim 1 wherein the AML is refractory.

4. The method of claim 1 wherein the AML is relapsed or refractory.

5. A method of treating a mammal with acute myeloid leukemia (AML) whose disease is dependent on MCL-1 comprising:
   acquiring a plurality of bone marrow cells from the mammal;
   determining an MCL-1 priming of the bone marrow cells determined by subjecting cells from the mammal's bone marrow to a BH3 mimetic that is selective for MCL-1 and determining the percentage change in the mitochondrial depolarization which corresponds to the MCL-I priming; and
   administering alvocidib, cytarabine, and mitoxantrone to the mammal if the bone marrow cells have the MCL-1 priming of at least 40%.

6. The method of claim 5 wherein the determination of MCL-1 priming includes permeabilizing the bone marrow cells.

7. The method of claim 5 wherein the AML is refractory.

8. The method of claim 5 wherein the AML is relapsed or refractory.

* * * * *